US012704519B2

(12) United States Patent
Pope et al.

(10) Patent No.: US 12,704,519 B2
(45) **Date of Patent: *Aug. 11, 2026**

(54) METHODS FOR DETECTING ASSAY INTERFERENTS AND INCREASING DYNAMIC RANGE

(71) Applicant: ABBOTT LABORATORIES, Abbott Park, IL (US)

(72) Inventors: Mark R. Pope, Abbott Park, IL (US); Stefan J. Hershberger, Abbott Park, IL (US); Qiaoqiao Ruan, Abbott Park, IL (US); Kerry M. Swift, Abbott Park, IL (US); Sergey Y. Tetin, Abbott Park, IL (US); Patrick Macdonald, Abbott Park, IL (US); Richard A. Haack, Abbott Park, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 1192 days.

This patent is subject to a terminal disclaimer.

(21) Appl. No.: 17/633,065

(22) PCT Filed: Aug. 6, 2020

(86) PCT No.: PCT/US2020/045297

§ 371 (c)(1),
(2) Date: Feb. 4, 2022

(87) PCT Pub. No.: WO2021/026403

PCT Pub. Date: Feb. 11, 2021

(65) Prior Publication Data

US 2022/0276256 A1 Sep. 1, 2022

Related U.S. Application Data

(60) Provisional application No. 62/883,919, filed on Aug. 7, 2019, provisional application No. 62/883,922, filed on Aug. 7, 2019.

(51) Int. Cl.

| | |
|---|---|
| ***G01N 33/58*** | (2006.01) |
| ***C09B 57/08*** | (2006.01) |
| ***C09K 11/07*** | (2006.01) |
| ***G01N 33/543*** | (2006.01) |

(52) U.S. Cl.
CPC ..... *G01N 33/582* (2013.01); *G01N 33/54306* (2013.01)

(58) Field of Classification Search
CPC ....................... G01N 33/54306; G01N 33/582
See application file for complete search history.

(56) References Cited

U.S. PATENT DOCUMENTS

| | | | |
|---|---|---|---|
| 4,510,251 | A | 4/1985 | Kirkemo et al. |
| 5,006,309 | A | 4/1991 | Khalil et al. |
| 5,063,081 | A | 11/1991 | Cozzette et al. |
| 5,089,424 | A | 2/1992 | Khalil et al. |
| 5,270,163 | A | 12/1993 | Gold et al. |
| 5,294,404 | A | 3/1994 | Grandone et al. |
| 5,468,646 | A | 11/1995 | Mattingly et al. |
| 5,475,096 | A | 12/1995 | Gold et al. |
| 5,567,588 | A | 10/1996 | Gold et al. |

(Continued)

FOREIGN PATENT DOCUMENTS

| | | |
|---|---|---|
| EP | 1403254 | 3/2004 |
| WO | WO 98/54574 | 12/1998 |

(Continued)

OTHER PUBLICATIONS

Cheng et al., "Comparison of three different assays for measuring thyroglobulin and thyroglobulin antibodies in patients with chronic lymphocytic thyroiditis," Clin. Biochem., 2017, vol. 50, issue 18, pp. 1183-1187.*

Adamczyk et al., Chemiluminescence quenching of pteroic acid-N-sulfonyl-acridinium-9-carboxamide conjugates by folate binding protein. Bioorg Med Chem Lett. May 3, 2004;14(9):2313-7.

Adamczyk et al., Chemiluminescent acridinium-9-carboxamide boronic acid probes: application to a homogeneous glycated hemoglobin assay. Bioorg Med Chem Lett. Mar. 1, 2006;16(5):1324-8.

Adamczyk et al., Immunoassay reagents for thyroid testing. 2. Binding properties and energetic parameters of a T4 monoclonal antibody and its Fab fragment with a library of thyroxine analog biosensors using surface plasmon resonance. Bioconjug Chem. Mar.-Apr. 1997;8(2):133-45.

(Continued)

*Primary Examiner* — Shafiqul Haq
(74) *Attorney, Agent, or Firm* — Lisa Mueller; Tristan A. Fuierer; Casimir Jones SC

(57) ABSTRACT

The disclosure provides kits and methods for detecting a substance that interferes with detection of an analyte in a sample and for expanding the dynamic range and reducing the hook effect of an immunoassay. The kits and methods employ two conjugates with two different detectable labels, at least one of which is a chemiluminescent compound of Formula (I).

(I)

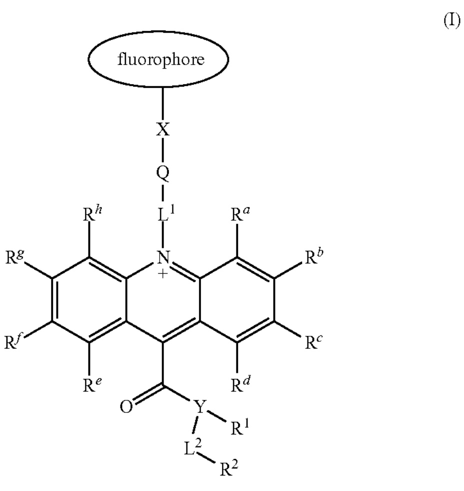

26 Claims, 12 Drawing Sheets

(56) References Cited

U.S. PATENT DOCUMENTS

| | | | |
|---|---|---|---|
| 5,595,877 | A | 1/1997 | Gold et al. |
| 5,620,850 | A | 4/1997 | Bamdad et al. |
| 5,637,459 | A | 6/1997 | Burke et al. |
| 5,683,867 | A | 11/1997 | Biesecker et al. |
| 5,705,337 | A | 1/1998 | Gold et al. |
| 6,156,800 | A | 12/2000 | Weichert et al. |
| 6,165,800 | A * | 12/2000 | Jiang .................... G01N 33/542 546/37 |
| 7,070,921 | B2 | 7/2006 | Huang et al. |
| 8,287,808 | B2 | 10/2012 | Krupenkin et al. |
| 8,445,199 | B2 | 5/2013 | Collier et al. |
| 9,157,910 | B2 | 10/2015 | Dowell et al. |
| 9,207,246 | B2 | 12/2015 | Collier et al. |
| 9,239,284 | B2 | 1/2016 | Livingston |
| 9,964,537 | B2 | 5/2018 | Collier et al. |
| 2003/0170881 | A1 | 9/2003 | Davis et al. |
| 2004/0018577 | A1 | 1/2004 | Emerson Campbell et al. |
| 2004/0038294 | A1 | 2/2004 | Evangelista et al. |
| 2005/0054078 | A1 | 3/2005 | Miller et al. |
| 2006/0121544 | A1 | 6/2006 | Boge et al. |
| 2006/0160164 | A1 | 7/2006 | Miller et al. |
| 2014/0273035 | A1 | 9/2014 | Dowell et al. |
| 2015/0330986 | A1 | 11/2015 | Grote |
| 2017/0153248 | A1 | 6/2017 | Goix et al. |
| 2018/0017552 | A1 | 1/2018 | Duffy et al. |
| 2022/0291223 | A1 * | 9/2022 | Hershberger ........... C09B 23/04 |

FOREIGN PATENT DOCUMENTS

| | | |
|---|---|---|
| WO | WO 2007/136386 | 11/2007 |
| WO | WO 2009/111431 | 9/2009 |
| WO | WO 2010/040227 | 4/2010 |
| WO | WO 2011/137533 | 11/2011 |
| WO | WO 2013/066441 | 5/2013 |
| WO | WO 2014/062551 | 4/2014 |
| WO | 2014/066704 | 5/2014 |
| WO | WO 2016/161400 | 10/2016 |
| WO | WO 2016/161402 | 10/2016 |

OTHER PUBLICATIONS

Adamczyk et al., Intrinsic factor-mediated modulation of cyanocobalamin-N-sulfonyl-acridinium-9-carboxamide chemiluminescence. Bioorg Med Chem Lett. Aug. 2, 2004;14(15):3917-21.

Adamczyk et al., Neopentyl 3-Triflyloxypropanesulfonate. A Reactive Sulfopropylation Reagent for the Preparation of Chemiluminescent Labels. J. Org. Chem. 1998, 63(16), 5636-5639.

Adamczyk et al., Regiodependent luminescence quenching of biotinylated N-sulfonyl-acridinium-9-carboxamides by avidin. Org Lett. Oct. 16, 2003;5(21):3779-82.

Bag et al., A BODIPY-luminol chemiluminescent resonance energy-transfer (CRET) cassette for imaging of cellular superoxide. Org Biomol Chem. Feb. 14, 2015;13(6):1763-7.

Bouvet et al., Polyreactivity is not an artefact. J Immunol Methods. Aug. 1, 2001;254(1-2):199-201.

Browne et al., Spectrally resolved chemiluminescent probes for sensitive multiplex molecular quantification. Anal Chem. Nov. 6, 2012;84(21):9222-9.

Cai et al., Introduction of functional groups into polymer films via deep-UV photolysis or electron-beam lithography: modification of polystyrene and poly(3-octylthiophene) by a functionalized perfluorophenyl azide. Chem. Mater. 1992, 4(4), 879-884.

Casesnoves et al., Influence of anti-insulin antibodies on insulin immunoassays in the autoimmune insulin syndrome. Ann Clin Biochem. Nov. 1998;35 ( Pt 6):768-74.

Demers et al., E. Thyroglobulin (Tg) Measurement. Thyroid, 2003; 13: 57-67.

Despres et al., Antibody interference in thyroid assays: a potential for clinical misinformation. Clin Chem. Mar. 1998;44(3):440-54.

Dexter. A Theory of Sensitized Luminescence in Solids. J. Chem. Phys. 1953, 21, 836-850.

Dodeigne et al., Chemiluminescence as diagnostic tool. A review. Talanta. Mar. 6, 2000;51(3):415-39.

Dong et al., Sulfur(VI) fluoride exchange (SuFEx): another good reaction for click chemistry. Angew Chem Int Ed Engl. Sep. 1, 2014;53(36):9430-48.

Fahie-Wilson et al., Hyperprolactinaemia due to macroprolactins: some progress but still a problem. Clin Endocrinol (Oxf). Jun. 2003;58(6):683-5.

Faulkner et al., Mechanisms of chemiluminescent electron-transfer reactions. I. Role of the triplet state in energy-deficient systems. J. Am. Chem. Soc. 1971, 93(9), 2097-2102.

Feldt-Rasmussen et al., Serum thyroglobulin (Tg) in presence of thyroglobulin autoantibodies (TgAb). Clinical and methodological relevance of the interaction between Tg and TgAb in vitro and in vivo. J Endocrinol Invest. Dec. 1985;8(6):571-6.

Fischer et al., Direct Transformation of Esters into Heterocyclic Fluorophores. Angew Chem Int Ed Engl. Feb. 23, 2018;57(9):2436-2440.

Glezer et al., Pitfalls in pituitary diagnosis: peculiarities of three cases. Clin Endocrinol (Oxf). Jul. 2002;57(1):135-9.

Gottlin et al., Isolation of novel EGFR-specific VHH domains. J Biomol Screen. Jan. 2009;14(1):77-85.

Haack et al., Chemoselective reaction of bifunctional carboxysulfonic acid systems: Preparation of useful intermediates for chemiluminescent, fluorescent and UV absorbing bifunctional linkers. Tetrahedron Letters, 2020, vol. 61, No. 40. 8 pages.

Haugen et al., 2015 American Thyroid Association Management Guidelines for Adult Patients with Thyroid Nodules and Differentiated Thyroid Cancer: The American Thyroid Association Guidelines Task Force on Thyroid Nodules and Differentiated Thyroid Cancer. Thyroid. Jan. 2016;26(1):1-133.

Haugland, The Handbook of Fluorescent Probes and Research Chemicals, Publisher, Molecular Probes, Inc., Eugene, Oreg. Jun. 1992. TOC only. 4 pages.

Heller. Electrical wiring of redox enzymes. Acc. Chem. Res. 1990. 23(5), 128-134.

Hiblot et al., Luciferases with Tunable Emission Wavelengths. Angew Chem Int Ed Engl. Nov. 13, 2017;56(46):14556-14560.

Hjiyiannakis et al., Thyroglobulin antibodies in differentiated thyroid cancer. Clin Oncol (R Coll Radiol). 1999;11(4):240-4.

Huang et al., Digital Microfluidic Dynamic Culture of Mammalian Embryos on an Electrowetting on Dielectric (EWOD) Chip. PLoS One. May 1, 2015;10(5):e0124196. 15 pages.

Huang et al., Gold nanoparticles based chemiluminescent resonance energy transfer for immunoassay of alpha fetoprotein cancer marker. Anal Chim Acta. Feb. 7, 2011;686(1-2):115-20.

International Preliminary Report on Patentability for PCT/US2020/045296. Mailed Feb. 17, 2022. 8 pages.

International Search Report and Written Opinion for PCT/US2020/045296. Mailed Dec. 3, 2020. 13 pages.

International Search Report and Written Opinion for PCT/US2020/045297. Mailed Oct. 15, 2020. 14 pages.

Kricka. Human anti-animal antibody interferences in immunological assays. Clin Chem. Jul. 1999;45(7):942-56.

Kuwahara et al., Autoantibody against testosterone in a woman with hypergonadotropic hypogonadism. J Clin Endocrinol Metab. Jan. 1998;83(1):14-6.

Levinson et al., Towards a better understanding of heterophile (and the like) antibody interference with modern immunoassays. Clin Chim Acta. Nov. 2002;325(1-2):1-15.

Lippi et al., Macroprolactin: searching for a needle in a haystack? Clin Chem Lab Med. Apr. 2016;54(4):519-22.

Liu et al., Proximity hybridization-regulated chemiluminescence resonance energy transfer for homogeneous immunoassay. Talanta. Jul. 1, 2016;154:455-60.

Marquette et al., Recent advances in multiplex immunoassays. Bioanalysis. May 2012;4(8):927-36.

Masters et al., Investigation of sex-hormone binding globulin interference in direct radioimmunoassays for testosterone and estradiol. Clin Chem. Jun. 1989;35(6):979-84.

Mattingly et al., Preparation of 5- and 6-(aminomethyl)fluorescein. Bioconjug Chem. Sep.-Oct. 1992;3(5):430-1.

(56) References Cited

OTHER PUBLICATIONS

Natrajan et al., A comparison of chemiluminescent acridinium dimethylphenyl ester labels with different conjugation sites. Org Biomol Chem. Mar. 7, 2015;13(9):2622-33.
Nealson et al., Bacterial bioluminescence: its control and ecological significance. Microbiol Rev. Dec. 1979;43(4):496-518.
Nishioka et al., New luminescent europium(III) chelates for DNA labeling. Inorg Chem. May 15, 2006;45(10):4088-96.
Ohashi et al., "Paradoxical" GH suppression by secretagogues in acromegaly? Horm Metab Res. Jul. 1993;25(7):393-4.
Oliner, A.A.(ed), Acoustic Surface Waves. Springer. 1978. TOC only. 8 pages.
Peng et al., EWOD (electrowetting on dielectric) digital microfluidics powered by finger actuation. Lab Chip. Mar. 21, 2014;14(6):1117-22.
Perros et al., Guidelines for the management of thyroid cancer. Clin Endocrinol (Oxf). Jul. 2014;81 Suppl 1:1-122.
Phillips et al., Energy transfer from chemiluminescent species in polymers. Nature. Sep. 9, 1967;215(5106):1163-5.
Preliminary Report on Patentability for PCT/US2020/045297. Mailed Feb. 17, 2022. 8 pages.
Rauhut. Chemiluminescence from concerted peroxide decomposition reactions. Acc. Chem. Res. 1969, 2(3), 80-87.
Ryall et al., Reappraisal of the causes of the "hook effect" in two-site immunoradiometric assays. Anal Biochem. Dec. 1982;127(2):308-15.
Sakata et al., Autoantibodies against thyroid hormones or iodothyronine. Implications in diagnosis, thyroid function, treatment, and pathogenesis. Ann Intern Med. Oct. 1985;103(4):579-89.
Sapin. Anti-insulin antibodies in insulin immunometric assays: a still possible pitfall. Eur J Clin Chem Clin Biochem. May 1997;35(5):365-7.
Schaadt et al., Assessment of the influence of thyroglobulin (Tg) autoantibodies and other interfering factors on the use of serum Tg as tumor marker in differentiated thyroid carcinoma. Thyroid. Jun. 1995;5(3):165-70.
Schneckenburger. Fluorescence Techniques in Biomedical Diagnostics: Instrumentation, Analysis and Unresolved Issues. Springer Ser Fluoresc. 2008, 6, 533-548.
Seliger et al., Stereo-specificity and firefly bioluminescence, a comparison of natural and synthetic luciferins. Proc Natl Acad Sci U S A. Aug. 1961;47(8):1129-34.
Shieh et al., Fluorogenic azidofluoresceins for biological imaging. J Am Chem Soc. Oct. 24, 2012;134(42):17428-31.
Sklenarova et al. Quantum dots as chemiluminescence enhancers tested by sequential injection technique: Comparison of flow and flow-batch conditions. J. Lumin. 2017, 184, 235-241.
Slaats et al., Interference of sex-hormone binding globulin in the "Coat-A-Count" testosterone no-extraction radioimmunoassay. Clin Chem. Feb. 1987;33(2 Pt 1):300-2.
Spindel et al., In vitro FRET sensing, diagnostics, and personalized medicine. Förster Resonance Energy Transfer—From Theory to Applications 2013, 271-322.
St-Jean et al., High prolactin levels may be missed by immunoradiometric assay in patients with macroprolactinomas. Clin Endocrinol (Oxf). Mar. 1996;44(3):305-9.
Sturgeon et al., Analysis of hCG: clinical applications and assay requirements. Ann Clin Biochem. Jul. 1998;35 ( Pt 4):460-91.
Suliman et al., Frequent misdiagnosis and mismanagement of hyperprolactinemic patients before the introduction of macroprolactin screening: application of a new strict laboratory definition of macroprolactinemia. Clin Chem. Sep. 2003;49(9):1504-9.
Symons. Interference with the Laboratory Assessment of Thyroid Funciton. Clin Biochem Rev., 1989; 10: 44-49.
Tate et al., Interferences in immunoassay. Clin Biochem Rev. May 2004;25(2):105-20.
Tseng et al., In vivo imaging of endogenous enzyme activities using luminescent 1,2-dioxetane compounds. J Biomed Sci. Jun. 24, 2015;22(1):45. 11 pages.
Turro et al., Modern Molecular Photochemistry of Organic Molecules. University Science Books, Mill Valley, California, 2010. TOC only. 25 pages.
Vaishya et al., Macroprolactin; a frequent cause of misdiagnosed hyperprolactinemia in clinical practice. J Reprod Infertil. Oct. 2010;11(3):161-7.
Vedejs et al., Reactive triflate alkylating agents. J. Org Chem., 1977, 42(19), 3109-3113.
Vining. Steroid Radioimmunoassay. Clin. Biochem. Rev., 1981; 2:39-49.
Wingert et al., Enhanced chemiluminescent resonance energy transfer in hollow calcium phosphate nanoreactors and the detection of hydrogen peroxide. Nanotechnology, 2007, 18, 295707-295713.
Yigitbasi. Multiplex immunoassay and bead based multiplex. Trends in Immunolabelled and Related Techniques, 2012, 351-360.
Zhao et al., A nonenzymatic chemiluminescent reaction enabling chemiluminescence resonance energy transfer to quantum dots. Chemistry. Jun. 1, 2010;16(21):6142-5.

* cited by examiner

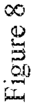
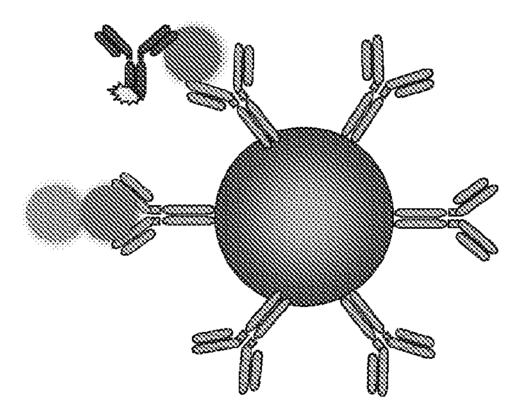
Scenario 2: Interferent binding to analyte, blocking analyte binding to conjugate Ab. The capture Ab should be selected to be able to bind to analyte or analyte-interferent complex
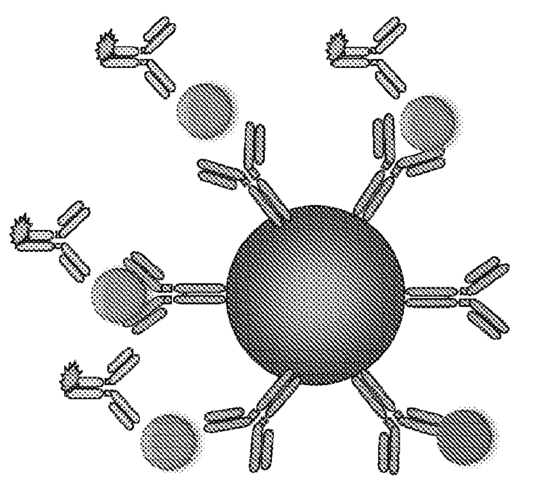
Scenario 1: Interferent binding to capture Ab, blocks analyte binding to capture Ab, anti-interferent conjugate can be used for flagging the interference
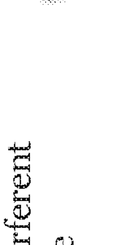
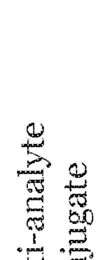
Anti-interferent conjugate
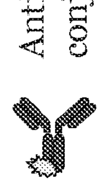

METHODS FOR DETECTING ASSAY INTERFERENTS AND INCREASING DYNAMIC RANGE

CROSS-REFERENCE TO RELATED APPLICATIONS

This application claims the benefit of U.S. Provisional Patent Application Nos. 62/883,922, filed Aug. 7, 2019, and 62/883,919, filed Aug. 7, 2019, the contents of which are incorporated by reference herein.

BACKGROUND

For the past several decades, immunoassays have been performed using fluorescence, chemiluminescence, or other means of generating a signal in response to an analyte. Immunoassays typically involve combining a sample suspected of containing an antigen with a reagent comprising a first antibody attached to a solid support, e.g., a microparticle, to form a reaction mixture. The antigen, if present in the sample, specifically binds to the first antibody. A conjugate, which comprises a second antibody having a detectable label attached thereto, is introduced to the reaction mixture and specifically binds to the antigen, which is specifically bound to the first antibody, which, as stated previously, is attached to the solid support. Such an assay is referred to as a sandwich immunoassay or an immunometric assay. The signal attributable to the detectable label is then measured after unbound conjugate is removed from the reaction mixture, typically by performing a wash step. The signal that is derived from the total volume of the reaction mixture is measured and then compared to a calibration curve to establish the concentration of antigen present in the sample.

Several different types of immunoassays suffer from the presence of interfering substances which lead to false or misleading results. Substances which may interfere with the reaction between analyte and reagent antibodies in an immunoassay include, for example, compounds with chemical differences but structural similarities that cross-react with the antibody, heterophile antibodies, human anti-animal antibodies, autoanalyte antibodies, rheumatoid factors, and other proteins. Lipaemia, cross-reactivity, and exogenous interferences due to pre-analytical variation or equipment reaction also can contribute to immunoassay interference. Interfering substances may lead to falsely elevated or falsely low analyte concentration in one or more assay systems depending on the site of the interference in the reaction. A wide range of analytes measured by immunoassay (e.g., hormones, biomarkers, drugs, cardiac troponin, and microbial serology) may be affected by immunoassay interference.

An immunoassay that includes a washing step to remove unbound sample analyte before introducing the conjugate antibody is generally referred to as a "two-step assay." An immunoassay that introduces the conjugate antibody and the analyte to antibody-coated microparticles together without intermediate washing steps is generally referred to as a "one-step" assay. Both one-step and two-step formats can exhibit limited assay dynamic range, thus some samples require re-testing with dilution. A "hook effect" or "prozone phenomenon" is a phenomenon of falsely low values observed in an immunoassay when an overwhelming amount of antigen is present in a "one-step assay" format. Hook effect is caused by insufficient capture antibody and detection antibody in an immunoassay, which limits the assay dynamic range.

There remains a need for systems, kits, and methods for detecting a substance that interferes with detection of an analyte in a sample, and for increasing the dynamic range of immunoassays while reducing hook effect.

BRIEF SUMMARY OF THE INVENTION

The disclosure provides a kit comprising: a) a first conjugate comprising a first detectable label attached to a first specific binding member that specifically binds an analyte, (b) a second conjugate comprising a second detectable label attached to a second specific binding member, wherein the second specific binding member specifically binds a substance which interferes with detection of the analyte in a sample, (c) a third specific binding member attached to a solid support, which either concurrently or competitively binds to the analyte and the substance which interferes with detection of the analyte, and optionally (d) a fourth specific binding member attached to the solid support, which specifically binds to the substance which interferes with detection of the analyte, wherein at least one of the first and second detectable labels comprises a compound of formula (I), or a salt thereof:

(I)

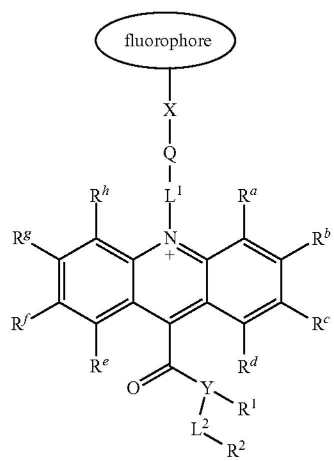

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ and $L^2$ are each independently selected from alkylene and heteroalkylene; $R^2$ is selected from —COOZ and —CN; Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl; and $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; wherein each alkyl, alkenyl, alkynyl, aryl, heteroaryl, cycloalkyl, heterocyclyl, arylalkyl, heteroarylalkyl, cycloalkylalkyl, heterocyclylalkyl, aryloxy, heteroalkyl, alkylene, and heteroalkylene is independently optionally substituted with 1, 2, 3, 4, or 5 substituents.

The disclosure also provides methods of detecting a substance that interferes with detection of an analyte in a sample. In one aspect, the method comprises (a) contacting a sample suspected of comprising an analyte and a substance that interferes with detection of the analyte with any one of the aforementioned kits under conditions that allow: (i) binding of the analyte to the third specific binding member, (ii) specific binding of the substance that interferes with detection of the analyte to the third specific binding member, or non-specific binding of the substance that interferes with detection of the analyte to the solid support surface, (iii) binding of the first conjugate to the analyte, (iv) binding of the second conjugate to the substance that interferes with detection of the analyte; and optionally (v) binding of a fourth specific binding member to the substance that interferes with detection of the analyte; (b) detecting the signal intensities of the first detectable label and the second detectable label; and (c) detecting the presence of the substance that interferes with detection of the analyte in the sample by quantifying and analyzing the signal intensities of the first detectable label and the second detectable label.

In another aspect, the method comprises: (a) contacting a sample suspected of comprising an analyte and a substance that interferes with detection of the analyte with any one of the aforementioned kits under conditions that allow: (i) binding of the analyte to the third specific binding member and binding of the analyte to the substance that interferes with detection of the analyte to form an analyte-interferent complex, (ii) binding of the first conjugate to the analyte, and (iv) binding of the second conjugate to the substance that interferes with detection of the analyte or the analyte-interferent complex; and optionally (v) binding of a fourth specific binding member to the substance that interferes with detection of the analyte; (b) detecting the signal intensities of the first detectable label and the second detectable label; and (c) detecting the presence of the substance that interferes with detection of the analyte in the sample by quantifying and analyzing the signal intensities of the first detectable label and the second detectable label.

In a further aspect, the method comprises: (a) contacting a sample suspected of comprising an analyte and a substance that interferes with detection of the analyte with any one of the aforementioned kits under conditions that allow: (i) binding of the analyte to the third specific binding member, (ii) binding of the first conjugate to the analyte and binding of the first conjugate to the substance that interferes with detection of the analyte, and (iv) binding of the second conjugate to the substance that interferes with detection of the analyte; and optionally (v) binding of a fourth specific binding member to the substance that interferes with detection of the analyte; (b) detecting the signal intensities of the first detectable label and the second detectable label; and (c) detecting the presence of the substance that interferes with detection of the analyte in the sample by quantifying and analyzing the signal intensities of the first detectable label and the second detectable label.

In another aspect, the method comprises: (a) contacting a sample suspected of comprising an analyte and a substance that interferes with detection of the analyte with any one of the aforementioned kits under conditions that allow: (i) binding of the analyte to the third specific binding member; (ii) specific or non-specific binding of the substance that interferes with detection of the analyte to the solid support surface, (iii) binding of the first conjugate to the analyte and specific or non-specific binding of the substance that interferes with detection of the analyte to the first conjugate, thereby increasing the amount of first conjugate available for detection, (iv) binding of the second conjugate to the substance that interferes with detection of the analyte; and (v) binding of a fourth specific binding member to the substance that interferes with detection of the analyte; (b) detecting the signal intensities of the first detectable label and the second detectable label; and (c) detecting the presence of the substance that interferes with detection of the analyte in the sample by quantifying and analyzing the signal intensities of the first detectable label and the second detectable label.

The disclosure also provides a kit comprising: (a) a first specific binding member comprising a biotin molecule and a first detectable label attached thereto, wherein the first specific binding member specifically binds an analyte; (b) a conjugate comprising a second detectable label attached to a second specific binding member that specifically binds to the analyte; (c) a solid support coated with streptavidin, wherein the streptavidin binds to the biotin molecule attached to the first specific binding member and a biotin molecule which interferes with detection of the analyte in a sample, wherein at least one of the first and second detectable labels comprises a compound of formula (I), or a salt thereof:

(I)

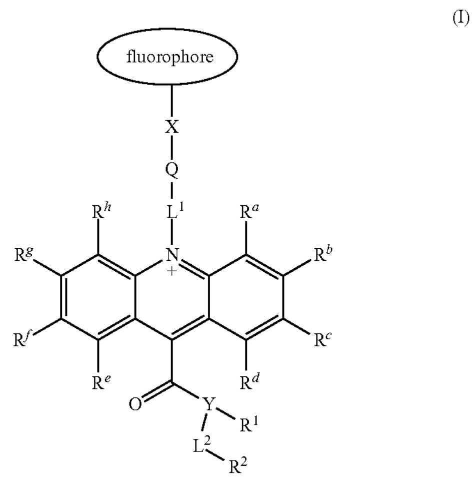

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ and $L^2$ are each independently selected from alkylene and heteroalkylene; $R^2$ is selected from —COOZ and —CN; Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl; $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; wherein each alkyl, alkenyl, alkynyl, aryl, heteroaryl, cycloalkyl, heterocyclyl, arylalkyl, heteroarylalkyl, cycloalkylalkyl, heterocyclylalkyl, aryloxy, heteroalkyl, alkylene, and heteroalkylene is independently optionally substituted with 1, 2, 3, 4, or 5 substituents. Also provided is a method for detecting a biotin molecule that interferes with detection of an analyte in a sample using the aforementioned kit. This method comprises (a) establishing a standard signal intensity (R value) of the first detectable label binding to the streptavidin-coated solid support in the absence of an interfering biotin molecule; (b) contacting a sample suspected of comprising both an analyte and a biotin molecule that interferes with detection of the analyte with the kit under conditions that allow: (i) binding of the analyte to the first specific binding member to form a first complex; (ii) binding of the conjugate to the analyte bound to the first specific binding member to form immunocomplexes; and (iii) binding of the streptavidin-coated solid support to the biotin molecule attached to the first specific binding member and the biotin molecule which interferes with detection of the analyte in a sample; (c) detecting the signal intensities of the first detectable label and the second detectable label; (d) correcting for the signal intensity of the second detectable label; and (e) detecting the presence of the biotin molecule that interferes with detection of the analyte in the sample.

Also provided is a kit comprising: (a) a first conjugate comprising a first detectable label attached to a first specific binding member that binds an analyte, (b) a second conjugate comprising a second detectable label attached to a second specific binding member, wherein the second specific binding member binds the same analyte as the first specific binding member and the binding affinity of the first specific binding member for the analyte is greater than that of the second specific binding member, and (c) a third specific binding member attached to a solid support, which can bind to the analyte concurrently with either the first or second specific binding member, wherein at least one of the first and second detectable labels comprises a compound of formula (I), or a salt thereof:

(I)

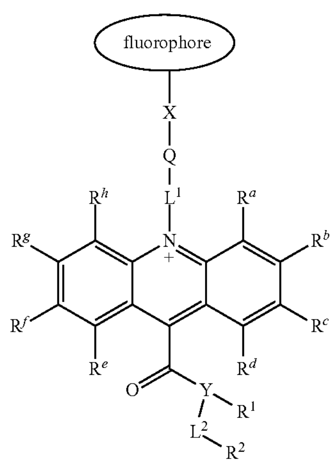

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ and $L^2$ are each independently selected from alkylene and heteroalkylene; $R^2$ is selected from —COOZ and —CN; Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl; $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; wherein each alkyl, alkenyl, alkynyl, aryl, heteroaryl, cycloalkyl, heterocyclyl, arylalkyl, heteroarylalkyl, cycloalkylalkyl, heterocyclylalkyl, aryloxy, heteroalkyl, alkylene, and heteroalkylene is independently optionally substituted with 1, 2, 3, 4, or 5 substituents.

The disclosure also provides a method of expanding the dynamic range of an immunoassay, which method comprises: (a) contacting a test sample suspected of comprising an analyte with the aforementioned kit, wherein the analyte binds to the third specific binding member; (b) removing analyte not bound to the third specific binding member by washing; (c) binding the first conjugate to the analyte and the second conjugate to the analyte, wherein the first and second conjugates do not concurrently bind to the analyte; (d) removing first and second conjugates not bound to the analyte by washing; (e) measuring the signal intensities of the first detectable label and the second detectable label; and (f) determining the concentration of the analyte by comparing the signal intensities of the first detectable label and the second detectable label based on a flag value, whereby the dynamic range of the immunoassay is expanded.

The disclosure provides a kit comprising: (a) a first conjugate comprising a first specific binding member that binds an analyte and a first detectable label; (b) a second conjugate comprising a second specific binding member and a second detectable label, wherein (i) the first specific binding member and second specific binding member are the same or are different, and (ii) the first and second detectable labels are different; (c) a third specific binding member attached to a solid support, which can bind to the analyte concurrently with either the first or second specific binding member, wherein at least one of the first and second detectable labels comprises a compound of formula (I), or a salt thereof:

(I)

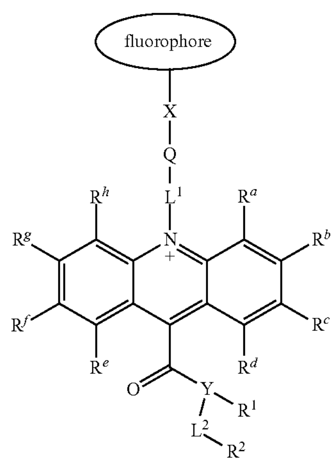

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ and $L^2$ are each independently selected from alkylene and heteroalkylene; $R^2$ is selected from —COOZ and —CN; Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl; $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; wherein each alkyl, alkenyl, alkynyl, aryl, heteroaryl, cycloalkyl, heterocyclyl, arylalkyl, heteroarylalkyl, cycloalkylalkyl, heterocyclylalkyl, aryloxy, heteroalkyl, alkylene, and heteroalkylene is independently optionally substituted with 1, 2, 3, 4, or 5 substituents.

The disclosure further provides a method of reducing hook effect and expanding the dynamic range of an immunoassay, which method comprises: (a) contacting a test sample suspected of comprising an analyte with the aforementioned kit, wherein the analyte binds to the third specific binding member and the first conjugate binds to the analyte; (b) removing any unbound analyte and unbound first conjugate by washing; (c) binding the second conjugate to the analyte, wherein the first and second conjugates do not concurrently bind to the analyte, (d) removing any unbound second conjugate by washing; (e) measuring the signal intensities of the first detectable label and the second detectable label; and (f) determining the concentration of the analyte based on a flag value, whereby hook effect of the immunoassay is reduced and dynamic range is expanded.

Also provided is a kit and/or method as described above which further comprises a photo multiplier tube (PMT) with two-channel detection, wherein the first channel is set to low gain/reduced amplification, and the second channel is set to the standard high gain, which results in an increased assay dynamic range that is orders of magnitude larger as compared to the one PMT channel.

BRIEF DESCRIPTION OF THE DRAWINGS

FIG. 8 is a schematic illustration of two different scenarios of analyte detection interference.

DETAILED DESCRIPTION OF THE INVENTION

Figure 1A:
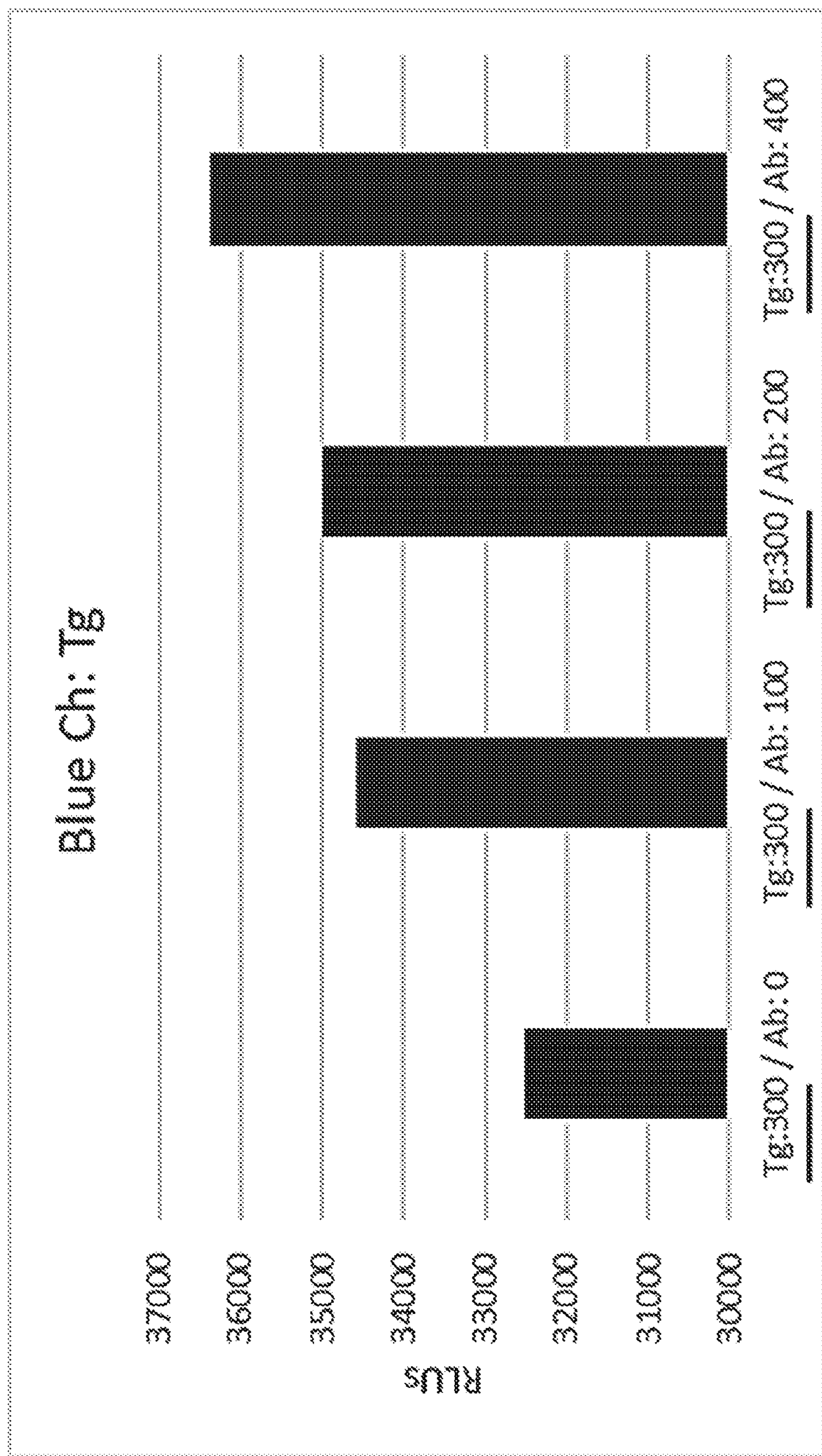
FIG. 1A is a graph showing the concentration of thyroglobulin (Tg) measured in the Tg/anti-Tg combination assay described in Example 68.

The present disclosure is predicated on the discovery that substances that interfere with immunoassay results can be detected by simultaneously employing a first specific binding member that binds an analyte and a second specific binding member that binds a substance which interferes with detection of the analyte in a sample. Binding of the analyte and the interfering substance to the first and second specific binding members, respectively, may be visualized using multiple conjugates that emit different signals. To this end, the present disclosure employs conjugates comprising chemiluminescent compounds containing an acridinium moiety and a fluorophore that are linked via a rigid diamine linker. Upon chemiluminescent triggering of the acridinium moiety, light output can be shifted to the emission wavelength of the attached fluorophore.

The present disclosure also is predicated on the discovery that the dynamic range of an assay, such as a two-step immunoassay, can be extended by simultaneously employing a high affinity antibody and a low affinity antibody within an assay. Analyte binding to the high and low affinity antibodies may be visualized using multiple conjugates that emit different signals. Two separate calibration curves can then be generated. To this end, the present disclosure employs conjugates comprising chemiluminescent compounds containing an acridinium moiety and a fluorophore that are linked via a rigid diamine linker. Upon chemiluminescent triggering of the acridinium moiety, light output can be shifted to the emission wavelength of the attached fluorophore. Use of multiple conjugates in a single assay employing different fluorophores may allow for detection of two or more analytes from one sample in a single test, which may be particularly useful for in vitro diagnostics. Furthermore, in one-step assay format, the "hook effect" can be resolved with introducing a second antibody conjugate comprising a detectable label different from the first conjugate (e.g., a different color label) to indicate the onset of the hook effect.

Definitions

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Sorrell, Organic Chemistry, 2nd edition, University Science Books, Sausalito, 2006; Smith, March's Advanced Organic Chemistry: Reactions, Mechanism, and Structure, 7th Edition, John Wiley & Sons, Inc., New York, 2013; Larock, Comprehensive Organic Transformations, 3rd Edition, John Wiley & Sons, Inc., New York, 2018; Carruthers, Some Modern Methods of Organic Synthesis, 3rd Edition, Cambridge University Press, Cambridge, 1987; the entire contents of each of which are incorporated herein by reference.

The term "alkyl," as used herein, means a straight or branched saturated hydrocarbon chain containing from 1 to 16 carbon atoms ($C_1$-$C_{16}$ alkyl), for example 1 to 14 carbon atoms ($C_1$-$C_{14}$ alkyl), 1 to 12 carbon atoms ($C_1$-$C_{12}$ alkyl), 1 to 10 carbon atoms ($C_1$-$C_{10}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl.

The term "alkenyl," as used herein, refers to a straight or branched hydrocarbon chain containing from 2 to 16 carbon atoms and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, refers to a straight or branched hydrocarbon chain containing from 2 to 16 carbon atoms and containing at least one carbon-carbon triple bond. Representative examples of alkynyl include, but are not limited to, ethynyl, propynyl, and butynyl.

The term "alkylene," as used herein, refers to a divalent group derived from a straight or branched chain hydrocarbon of 1 to 10 carbon atoms ($C_1$-$C_{10}$ alkylene), for example, of 1 to 6 carbon atoms ($C_1$-$C_6$ alkylene). Representative examples of alkylene include, but are not limited to, $—CH_2—$, $—CH_2CH_2—$, $—CH(CH_3)—$, $—CH_2CH_2CH_2—$, $—CH_2CH(CH_3)—$, $—CH_2CH_2CH_2CH_2—$, $—CH_2CH(CH_3) CH_2—$, $—CH_2CH_2CH(CH_3)—$, $—CH_2CH_2CH_2CH_2CH_2—$, $—CH_2CH(CH_3) CH_2CH_2—$, $—CH(CH_3) CH_2CH_2CH_2—$, $—CH_2CH_2CH_2CH_2CH_2CH_2—$, $—CH_2CH_2CH(CH_3) CH_2CH_2—$, $—CH_2CH(CH_3) CH_2CH_2CH_2—$, and $—CH(CH_3) CH_2CH_2CH_2CH_2—$.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "aryl," as used herein, refers to a phenyl group, or a bicyclic or tricyclic aromatic fused ring system. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl and phenanthreneyl.

The term "aryloxy," as used herein, means an aryl group, as defined herein, appended to the parent molecular moiety through an oxygen atom.

The term "arylalkyl," as used herein, refers to an aryl group, as defined herein, appended to the parent molecular moiety through an alkyl group, as defined herein. Representative examples of arylalkyl include, but are not limited to, phenylmethyl (i.e. benzyl) and phenylethyl.

The term "cycloalkyl," as used herein, refers to a saturated carbocyclic ring system containing three to ten carbon atoms and zero heteroatoms. The cycloalkyl may be monocyclic, bicyclic, bridged, fused, or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[1.1.1]pentanyl, bicyclo[2.2.1]heptanyl, bicyclo[3.2.1]octanyl, and bicyclo[5.2.0]nonanyl.

The term "cycloalkenyl," as used herein, means a non-aromatic monocyclic or multicyclic carbocyclic ring system containing at least one carbon-carbon double bond and preferably having from 5-10 carbon atoms per ring. Exemplary monocyclic cycloalkenyl rings include, but are not limited to, cyclopentenyl, cyclohexenyl, cycloheptenyl, and bicyclo[2.2.1]heptenyl.

As used herein, the term "cycloalkylalkyl" refers to a cycloalkyl group, as defined herein, appended to the parent molecular moiety through an alkylene group, as defined herein. Representative examples of cycloalkylalkyl include, but are not limited to, cyclohexylmethyl.

The term "diamine linker," as used herein, refers to a linker moiety having an amine functional group (—NH— or —NR—) at each end. The diamine linker may be linear, branched, or cyclic.

The term "halogen" or "halo," as used herein, means F, Cl, Br, or I.

The term "haloalkyl," as used herein, means an alkyl group, as defined herein, in which one or more hydrogen atoms are replaced by a halogen. For example, one, two, three, four, five, six, seven or eight hydrogen atoms can be replaced by a halogen, or all hydrogen atoms can be replaced by a halogen. Representative examples of haloalkyl include, but are not limited to, fluoromethyl, difluoromethyl, trifluoromethyl, chloromethyl, dichloromethyl, trichloromethyl, 2-fluoroethyl, 2,2-difluoroethyl, 2,2,2-trifluoroethyl, perfluoroethyl, 2-fluoro-2-methylpropyl, and 3,3,3-trifluoropropyl.

The term "haloalkoxy," as used herein, means at least one haloalkyl group, as defined herein, is appended to the parent molecular moiety through an oxygen atom. Representative examples of haloalkoxy include, but are not limited to, trifluoromethoxy.

The term "heteroalkyl," as used herein, refers to an alkyl group, as defined herein, in which at least one carbon atom has been replaced with a heteroatom such as N, O, P, or S. Representative examples of heteroalkyls include, but are not limited to, alkyl ethers, secondary and tertiary alkyl amines, amides, and alkyl sulfides.

The term "heteroalkylene," as used herein, refers to an alkylene group, as defined herein, in which at least one carbon atom has been replaced with a heteroatom such as N, O, P, or S. Representative examples of heteroalkylene groups include polyethylene oxide and polypropylene oxide chains, polyethyleneimine groups, and the like.

The term "heteroaryl," as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O, and S (e.g. 1, 2, 3, or 4 heteroatoms independently selected from O, S, and N). The five-membered aromatic monocyclic rings have two double bonds and the six membered six membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein or a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings.

The term "heteroarylalkyl," as used herein, refers to a heteroaryl group, as defined herein, appended to the parent molecular moiety through an alkylene group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl) propyl, thien-2-ylmethyl, and thien-3-ylmethyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.13,7]decane), and oxa-adamantane (2-oxatricyclo[3.3.1.13,7]decane). The monocyclic, bicyclic, and tricyclic heterocycles are connected to the parent molecular moiety through any carbon atom or any nitrogen atom contained within the rings.

As used herein, the term "heterocyclylalkyl" refers to a heterocyclyl group, as defined herein, appended to the parent molecular moiety through an alkylene group, as defined herein. Representative examples of heterocyclylalkyl include, but are not limited to, piperidin-4-ylmethyl, piperazin-1-ylmethyl, 3-methyl-1-pyrrolidin-1-ylbutyl, (1R)-3-methyl-1-pyrrolidin-1-ylbutyl, (1S)-3-methyl-1-pyrrolidin-1-ylbutyl, and 3-morpholinopropyl.

The term "hydroxy," as used herein, means an —OH group.

The term "hydroxyalkyl," as used herein, refers to an alkyl group, as defined herein, substituted with at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

In some instances, the number of carbon atoms in a group (e.g., alkyl, alkoxy, or cycloalkyl) is indicated by the prefix "Cx-Cy-", wherein x is the minimum and y is the maximum number of carbon atoms in the group. Thus, for example, "$C_1$-$C_3$-alkyl" refers to an alkyl group containing from 1 to 3 carbon atoms.

The term "substituent" refers to a group substituted on an atom of the indicated group.

When a group or moiety can be substituted, the term "substituted" indicates that one or more (e.g., 1, 2, 3, 4, 5, or 6; in some embodiments 1, 2, or 3; and in other embodiments 1 or 2) hydrogens on the group indicated in the expression using "substituted" can be replaced with a selection of recited indicated groups or with a suitable group known to those of skill in the art (e.g., one or more of the groups recited below). Substituent groups include, but are not limited to, halogen, =O, =S, cyano, nitro, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, arylalkyloxy, amino, alkylamino, dialkylamino, acylamino, aminoalkyl, arylamino, sulfonylamino, sulfinylamino, sulfonyl, alkylsulfonyl, arylsulfonyl, aminosulfonyl, sulfinyl, carboxy (—COOH), ketone, amide, carbamate, phosphoryl, selenyl, and acyl.

Kits

The disclosure provides a kit comprising: (a) a first conjugate comprising a first detectable label attached to a first specific binding member that specifically binds an analyte, (b) a second conjugate comprising a second detectable label attached to a second specific binding member, wherein the second specific binding member specifically binds a substance which interferes with detection of the analyte in a sample, (c) a third specific binding member attached to a solid support, which either concurrently or competitively binds to the analyte and the substance which interferes with detection of the analyte, and optionally (d) a fourth specific binding member attached to the solid support, which specifically binds to the substance which interferes with detection of the analyte.

Also provided is a kit comprising: (a) a first specific binding member comprising a biotin molecule and a first detectable label attached thereto, wherein the first specific binding member specifically binds an analyte; (b) a conjugate comprising a second detectable label attached to a second specific binding member that specifically binds to the analyte; and (c) a solid support coated with streptavidin, wherein the streptavidin binds to the biotin molecule attached to the first specific binding member and a biotin molecule which interferes with detection of the analyte in a sample.

The disclosure further provides a kit comprising: (a) a first conjugate comprising a first detectable label attached to a first specific binding member that binds an analyte, (b) a second conjugate comprising a second detectable label attached to a second specific binding member, wherein the second specific binding member binds the same analyte as the first specific binding member and the binding affinity of the first specific binding member for the analyte is greater than that of the second specific binding member, and (c) a third specific binding member attached to a solid support, which can bind to the analyte concurrently with either the first or second specific binding member.

Also provided is a kit comprising (a) a first conjugate comprising a first specific binding member that binds an analyte and a first detectable label; (b) a second conjugate comprising a second specific binding member and a second detectable label, wherein (i) the first specific binding member and second specific binding member are the same or are different, and (ii) the first and second detectable labels are different; and (c) a third specific binding member attached to a solid support, which can bind to the analyte concurrently with either the first or second specific binding member.

It will be appreciated that the components described below with respect to kits are also useful in the methods described herein.

In certain embodiments, the kit can comprise instructions for assaying a test sample for an analyte by an assay described herein, e.g., a microparticle assay or an assay for use in a point-of-care device. The instructions can be in paper form or computer-readable form, such as a disk, CD, DVD, or the like. Alternatively or additionally, the kit can comprise a calibrator or control, e.g., purified, and optionally lyophilized, analyte (or a fragment thereof), and/or at least one container (e.g., tube, microtiter plates or strips, which can be already coated with one or more analyte-binding molecules) for conducting the assay, and/or a buffer, such as an assay buffer or a wash buffer, either one of which can be provided as a concentrated solution, a trigger solution for the detectable label (e.g., a chemiluminescent label), or a stop solution. Ideally, the kit comprises all components, i.e., reagents, standards, buffers, diluents, etc., which are necessary to perform the assay. The instructions also can include instructions for generating a standard curve or a reference standard for purposes of quantifying an analyte.

Conjugates

In some embodiments, the kits and methods described herein comprise a first conjugate comprising a first detectable label attached to a first specific binding member that specifically binds an analyte, and a second conjugate comprising a second detectable label attached to a second specific binding member. In some embodiments, the second specific binding member specifically binds a substance which interferes with detection of the analyte in a sample. The kits and methods described herein also comprise a third specific binding member attached to a solid support, which can concurrently bind to the analyte, and, in some embodiments, to the substance which interferes with detection of the analyte. In some embodiments, the kits and methods described herein may optionally comprise a fourth specific binding member attached to the solid support, which specifically binds to the substance which interferes with detection of the analyte. In embodiments where the kit is used to detect a biotin molecule that interferes with detection of an analyte in a sample, the first specific binding member comprises a biotin molecule and a first detectable label attached thereto, wherein the first specific binding member specifically binds an analyte, and the conjugate comprises a second detectable label attached to a second specific binding member that specifically binds to the analyte.

The terms "specific binding partner," "specific binding member," and "binding member" are used interchangeably herein and refer to one of two or more different molecules that specifically recognize the other molecule compared to substantially less recognition of other molecules. By "specifically bind" or "binding specificity," it is meant that the binding member binds the analyte molecule with specificity sufficient to differentiate between the analyte molecule and other components or contaminants of the sample. As will be appreciated by those in the art, an appropriate specific binding member will be determined by the analyte to be analyzed. In one embodiment, the solid support desirably comprises a plurality (e.g., 2 or more, 50 or more, 100 or more, 1,000 or more, or 5,000 or more) of specific binding members immobilized on the surface thereof which bind to an analyte of interest. Following a sufficient incubation time between the solid support and the sample, as discussed herein, one or more analytes of interest present in the sample desirably are captured on the surface of the solid support via the specific binding members immobilized on the surface of the solid support. The term "immobilized," as used herein, refers to a stable association of a binding member with a surface of a solid support.

Binding members for a wide variety of target molecules are known or can be readily found or developed using known techniques. For example, when the target analyte is a protein, the binding members may include proteins, particularly antibodies or fragments thereof (e.g., antigen-binding fragments (Fabs), Fab' fragments, $F(ab')_2$ fragments), recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (VHH and methods of making them are described in Gottlin et al., *Journal of Biomolecular Screening,* 14:77-85 (2009)), recombinant VHH single-domain antibodies, disulfide-linked Fvs ("sdFv"), anti-idiotypic ("anti-Id") antibodies, and functionally active epitope-binding fragments of any of the above, full-length polyclonal or monoclonal antibodies, antibody-like fragments, etc., other proteins, such as receptor proteins, Protein A, or Protein C. In embodiments where the analyte is a small molecule, such as a steroid, bilin, retinoid, or lipid, the first and/or the second binding member may be a scaffold protein (e.g., a lipocalin) or a receptor. In some cases, a binding member for protein analytes may be a peptide. For example, when the target analyte is an enzyme, suitable binding members may include enzyme substrates and/or enzyme inhibitors which may be a peptide, a small molecule, and the like. In some cases, when the target analyte is a phosphorylated species, a binding member may comprise a phosphate-binding agent. For example, the phosphate-binding agent may comprise metal-ion affinity media (see, e.g., U.S. Pat. No. 7,070,921 and U.S. Patent Application No. 2006/0121544). In other embodiments, the binding member may be a vitamin, a nutrient, a nutrient metabolite, a pharmaceutical (e.g., an antibiotic), or a drug of abuse.

In certain cases, a specific binding member may be an aptamer, such as those described in U.S. Pat. Nos. 5,270,163; 5,475,096; 5,567,588; 5,595,877; 5,637,459; 5,683,867; and 5,705,337. The term "aptamer" as used herein refers to a nucleic acid or peptide molecule that can bind to pre-selected targets including small molecules, proteins, and peptides among others with high affinity and specificity. Nucleic acid aptamers (e.g., single-stranded DNA molecules or single-stranded RNA molecules) may be developed for capturing virtually any target molecule. Aptamers bind target molecules in a highly specific, conformation-dependent manner, typically with very high affinity, although aptamers with lower binding affinity can be selected. Aptamers may distinguish between target analyte molecules based on very small structural differences such as the presence or absence of a methyl or hydroxyl group and certain aptamers can distinguish between D- and L-enantiomers and diastereomers. Aptamers may bind small molecular targets, including drugs, metal ions, and organic dyes, peptides, biotin, and proteins. Aptamers can retain functional activity after biotinylation, fluorescein labeling, and when attached to glass surfaces and microspheres.

Nucleic acid aptamers are oligonucleotides that may be single stranded oligodeoxynucleotides, oligoribonucleotides, or modified oligodeoxynucleotides or oligoribonucleotides, A "modified" oligodeoxynucleotide or oligoribonucleotide refers to nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl; 2-O-alkyl; 2-O-allyl; 2'-S-alkyl; 2'-S-allyl; 2'-fluoro-; 2'-halo or 2-azido-ribose, carbocyclic sugar analogues, anomeric sugars; epimeric sugars such as arabinose, xyloses or lyxoses, pyranose sugars, furanose sugars, and sedoheptulose.

Peptide aptamers may be designed to interfere with protein interactions. Peptide aptamers may be based on a protein scaffold onto which a variable peptide loop is attached, thereby constraining the conformation of the aptamer. In some cases, the scaffold portion of the peptide aptamer is derived from bacterial thioredoxin A (TrxA).

When the analyte is a carbohydrate, suitable binding members include, for example, antibodies, lectins, and selectins. As will be appreciated by those of ordinary skill in the art, any molecule that can specifically associate with an analyte of interest may potentially be used as a binding member.

In certain embodiments, suitable analyte/binding member complexes can include, but are not limited to, antibodies/antigens, antigens/antibodies, receptors/ligands, ligands/receptors, proteins/nucleic acid, enzymes/substrates and/or inhibitors, carbohydrates (including glycoproteins and glycolipids)/lectins and/or selectins, proteins/proteins, proteins/small molecules, etc.

In a particular embodiment, a specific binding member may be attached to a solid support via a linkage, which may comprise any moiety, functionalization, or modification of the support and/or binding member that facilitates the attachment of the binding member to the support. The linkage between the binding member and the support may include one or more chemical or physical (e.g., non-specific attachment via van der Waals forces, hydrogen bonding, electrostatic interactions, hydrophobic/hydrophilic interactions; etc.) bonds and/or chemical spacers providing such bond(s). Certain embodiments utilize binding members that are proteins or polypeptides, and any number of techniques may be used to attach a polypeptide to a wide variety of solid supports (see, e.g., U.S. Pat. No. 5,620,850; and Heller, *Acc. Chem. Res.,* 23:128 (1990)).

In some embodiments, the binding affinity between analyte molecules and binding members should be sufficient to remain bound under the conditions of the assay, including wash steps to remove molecules or particles that are non-specifically bound. In some cases, for example in the detection of certain biomolecules, the binding constant of the analyte molecule to its complementary binding member may be between at least about $10^4$ and about $10^6$ $M^{-1}$, at least about $10^5$ and about $10^9$ $M^{-1}$, at least about $10^7$ and about $10^9$ $M^{-1}$, greater than about $10^9$ $M^{-1}$, or greater.

In certain embodiments, the first conjugate comprises a first specific binding member that specifically binds an analyte and a first detectable label, while the second conjugate comprises a second specific binding member and a second detectable label. In some embodiments, the second specific binding member specifically binds a substance which interferes with detection of the analyte in a sample, as described further below. In such embodiments, the second specific binding member may preferentially bind to the substance that interferes with detection of the analyte in the presence of the analyte. A specific binding member "preferentially binds" to a binding partner (e.g., analyte or substance that interferes with analyte detection) when it shows preference for binding to a particular binding partner over others.

In other embodiments, the second specific binding member binds the same analyte as the first specific binding member, albeit with a different affinity. In this regard, the binding affinity of the first specific binding member for the analyte is greater than that of the second specific binding member. In some embodiments, difference in binding affinity of the first specific binding member and the second specific binding member for the analyte ranges from about 3-fold to about 5-fold, from about 5-fold to about 100-fold, from about 5-fold to about 10-fold, from about 5-fold to about 25-fold, from about 25-fold to about 50-fold, or from about 50-fold to about 100-fold. Ideally, the binding affinity of the first specific binding member for the analyte is about 3-fold, about 5-fold, about 10-fold, about 25-fold, about 50-fold, or about 100-fold greater than that of the second specific binding member.

The first and second specific binding members may be directly or indirectly attached to the first and second detectable labels, respectively. In some embodiments, the first and second specific binding members are the same, but comprise different detectable labels. In other embodiments, the first and second detectable labels are different. In either case, the first and second detectable labels ideally are different. In some embodiments, the third specific binding member may also comprise a detectable label, as described herein. The terms "detectable label," and "label," as used herein, refer to a moiety that can produce a signal that is detectable by visual or instrumental means. The detectable label may be, for example, a signal-producing substance, such as a chromagen, a fluorescent compound, an enzyme, a chemiluminescent compound, a radioactive compound, and the like. In one embodiment, at least one of the first and second detectable labels comprises a compound of formula (I), or a salt thereof:

(I)

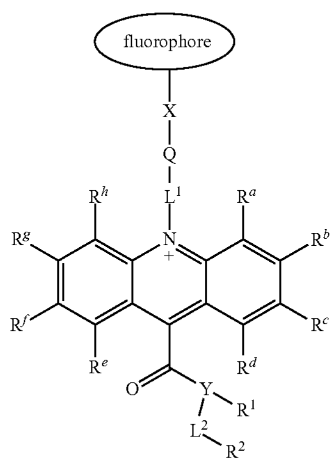

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ and $L^2$ are each independently selected from alkylene and heteroalkylene; $R^2$ is selected from —COOZ and —CN; Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl; and $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; wherein each alkyl, alkenyl, alkynyl, aryl, heteroaryl, cycloalkyl, heterocyclyl, arylalkyl, heteroarylalkyl, cycloalkylalkyl, heterocyclylalkyl, aryloxy, heteroalkyl, alkylene, and heteroalkylene is independently optionally substituted with 1, 2, 3, 4, or 5 substituents.

The group X is —NH— or a diamine linker. In some embodiments, X is —NH—. In some embodiments, X is a diamine linker. In some embodiments, the diamine linker may have formula —NR'-L'—NR"—, wherein R' and R" are each independently selected from hydrogen and methyl, and L' is selected from alkylene, heteroalkylene, cycloalkylene, and cycloalkenylene. In some embodiments, the diamine linker may by a cyclic diamine linker (e.g., a monocyclic or bicyclic diamine linker). In some embodiments, the diamine linker may be a rigid diamine linker. Exemplary rigid diamine linkers include the following:

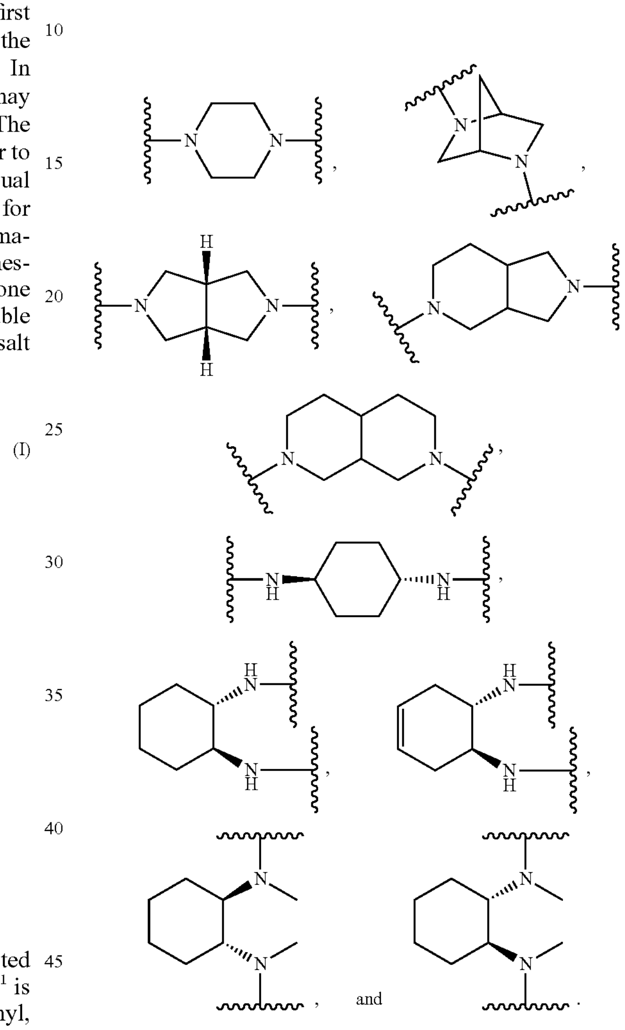

In some embodiments, X is selected from:

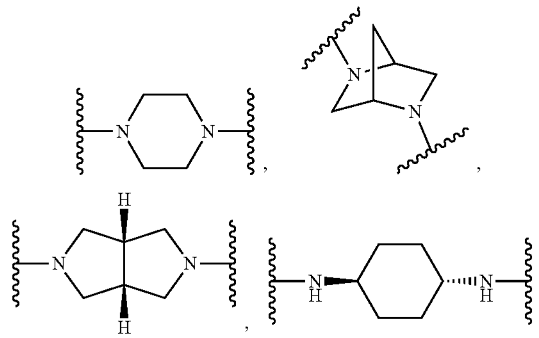

-continued

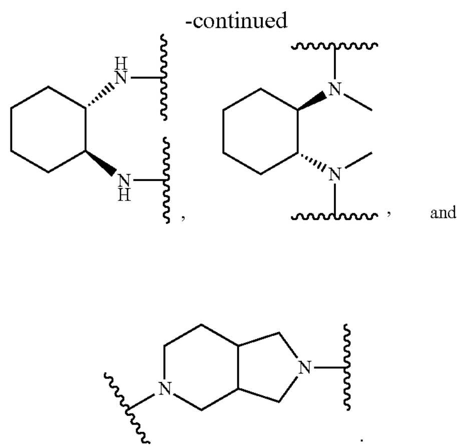

and

In some embodiments, X is:

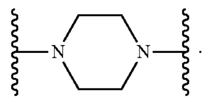

The group Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; and when Y is oxygen or sulfur, $R^1$ is absent.

In some embodiments, Y is nitrogen and $R^1$ is —$SO_2$-A. In some embodiments, A is aryl. In some embodiments, A is phenyl. In some embodiments, A is unsubstituted or substituted with 1, 2, 3, 4, or 5 substituents selected from $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, and amino. In some embodiments, A is phenyl that is substituted with 1 substituent selected from $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, and amino. In some embodiments, A is phenyl that is substituted with 1 substituent selected from $C_1$-$C_4$ alkyl. In some embodiments, A is phenyl that is substituted with 1 methyl group. In some embodiments, A is p-tolyl.

$R^2$ is selected from —COOZ and —CN, and Z is selected from hydrogen, alkyl, alkenyl, alkynyl, aryl, heteroaryl, cycloalkyl, heterocyclyl, arylalkyl, heteroarylalkyl, cycloalkylalkyl, heterocyclylalkyl, aryloxy, and heteroalkyl. In some embodiments, $R^2$ is —COOZ. In some embodiments, Z is selected from hydrogen and $C_1$-$C_4$ alkyl. In some embodiments, Z is hydrogen.

In some embodiments, Q is —CO—. In some embodiments, Q is —$SO_2$—.

$L^1$ and $L^2$ are each independently selected from alkylene and heteroalkylene. In some embodiments, $L^1$ and $L^2$ are each independently $C_1$-$C_4$-alkylene. In some embodiments, L' is —$CH_2CH_2CH_2$—. In some embodiments, $L^2$ is —$CH_2CH_2CH_2$—.

In some embodiments, each $R^a$, $R^b$, $R^c$, $R^d$, $R^e$, $R^f$, $R^g$, and $R^l$ is hydrogen.

In some embodiments, the compound is a compound of formula (Ia):

(Ia)

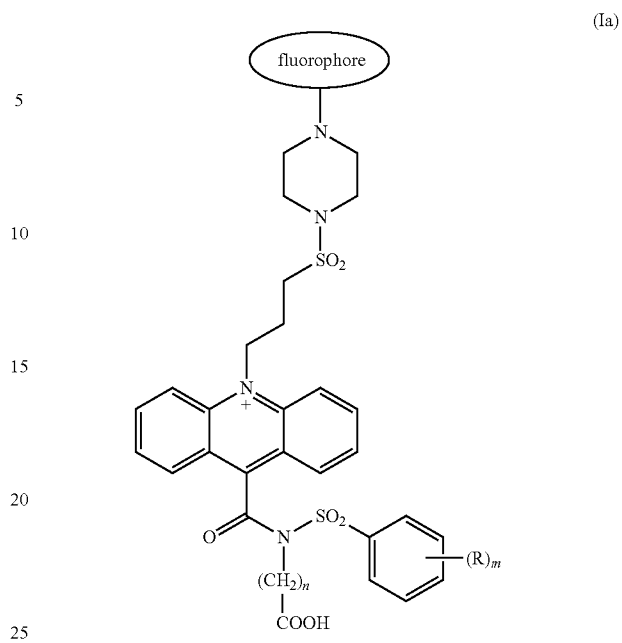

or a salt thereof, wherein: each R is independently selected from the group consisting of $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; m is 0, 1, 2, 3, 4, or 5; and n is 1, 2, 3, 4, 5, or 6.

In some embodiments, m is 1 or 2. In some embodiments, m is 1. In some embodiments, m is 1 and R is $C_1$-$C_4$ alkyl. In some embodiments, m is 1 and R is methyl. In some embodiments, n is 3.

In some embodiments, the compound is a compound of formula (Ib), or a salt thereof:

(Ib)

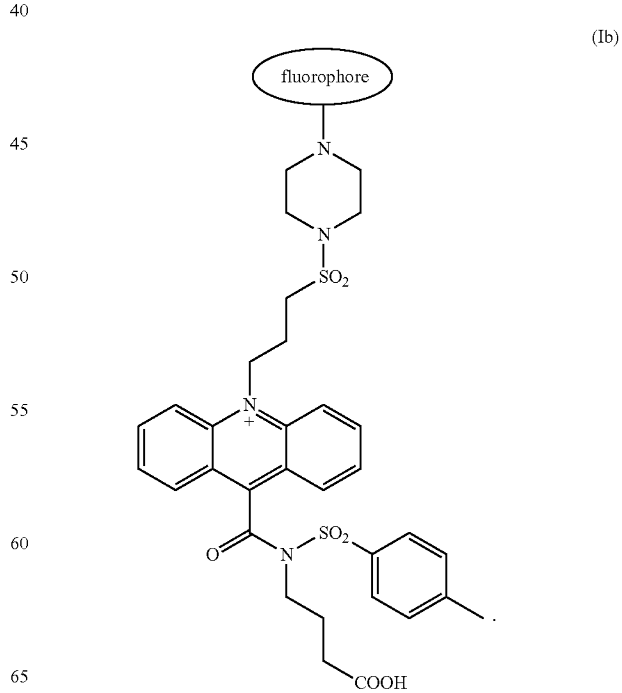

Any reference made herein to a compound of formula (I) should also be interpreted as reference to a compound of formula (Ia) or formula (Ib), whether expressly stated or not.

In some embodiments, in any of the compounds of formula (I), formula (Ia), or formula (Ib), the fluorophore is selected from a fluorescein, a rhodamine, a boron-dipyrromethene, a cyanine, an oxazine, a thiazine, a coumarin, a naphthalimide, a rhodol, a naphthalene, a squaraine, a porphyrin, a flavin, and a lanthanide-based dye.

Suitable fluorophores include, but are not limited to, QUASAR® dyes available from Biosearch Technologies, Novato, Calif.), fluorescein and fluorescein dyes (e.g., fluorescein isothiocyanate or FITC, naphthofluorescein, 4',5'-dichloro-2',7'-dimethoxy-fluorescein, 6-carboxyfluoresceins (e.g., FAM™), VIC®, NED™, carbocyanine, merocyanine, styryl dyes, oxonol dyes, phycoerythrin, erythrosin, eosin, rhodamine dyes (e.g., carboxytetramethylrhodamine or TAMRA™, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), OREGON GREEN® Dyes (e.g., OREGON GREEN 488, OREGON GREEN 500, OREGON GREEN 514), TEXAS RED®, TEXAS RED-X, SPECTRUM RED™, SPECTRUM GREEN™, cyanine dyes (e.g., CY-3™, CY-5™, CY-3.5™, CY-5.5™), ALEXA FLUOR® dyes (e.g., ALEXA FLUOR 350, ALEXA FLUOR 488, ALEXA FLUOR 532, ALEXA FLUOR 546, ALEXA FLUOR 568, ALEXA FLUOR 594, ALEXA FLUOR 633, ALEXA FLUOR 660 and ALEXA FLUOR 680), BODIPY® dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDYE® (e.g., IRD40, IRD 700, IRD 800), and the like. Examples of other suitable fluorescent dyes that can be used and methods for linking or incorporating fluorescent dyes to oligonucleotides, such as probes, can be found in RP Haugland, "The Handbook of Fluorescent Probes and Research Chemicals", Publisher, Molecular Probes, Inc., Eugene, Oreg. (June 1992)). Fluorescent dyes as well as labeling kits are commercially available from, for example, Amersham Biosciences, Inc. (Piscataway, N.J.), Molecular Probes Inc. (Eugene, Oreg.), and New England Biolabs Inc. (Beverly, Mass.).

As those skilled in the art appreciate, a fluorophore can be attached to a molecule via reaction of two reactive moieties, one on the fluorophore and one on the remainder of the molecule. For example, many commercially available fluorophores are available with a reactive functional group such as a carboxylic acid, an isocyanate, an isothiocyanate, a maleimide, or an ester such as a succinimidyl, pentafluorophenyl or tetrafluorophenyl ester. The fluorophore can be chosen to include a reactive group that will react with a functional group on the remainder of the molecule. For example, a fluorophore isothiocyanate or a fluorophore succinimidyl ester can react with an amine group. It will be understood that the term "fluorophore" as used when describing the molecules disclosed herein includes both the fluorescent moiety itself and also any linking atoms that serve to connect the fluorescent moiety to the remainder of the molecule.

In some embodiments, the fluorophore is selected from:

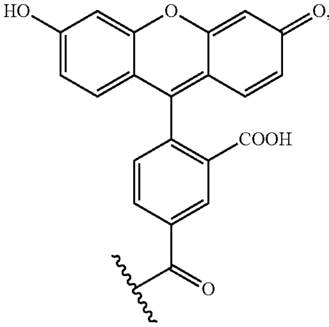

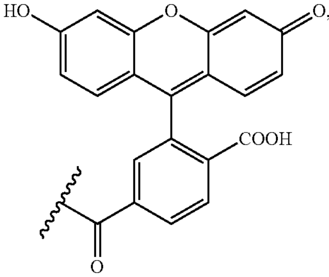

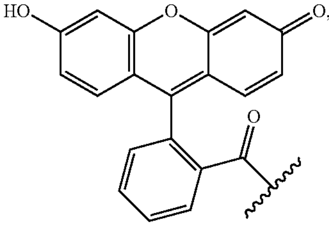

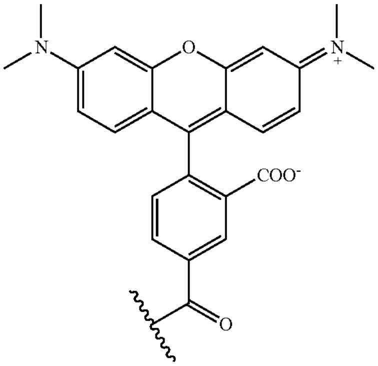

,

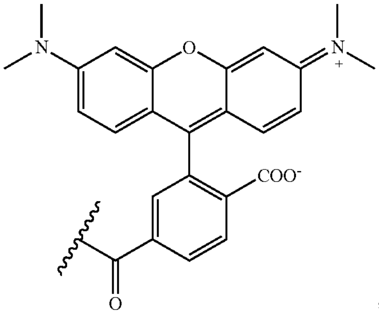

,

-continued
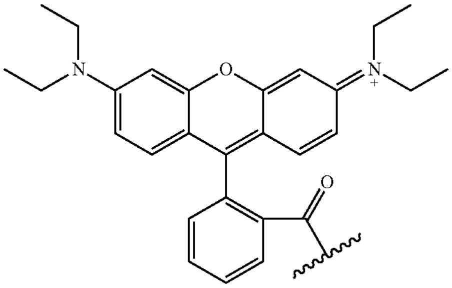
,
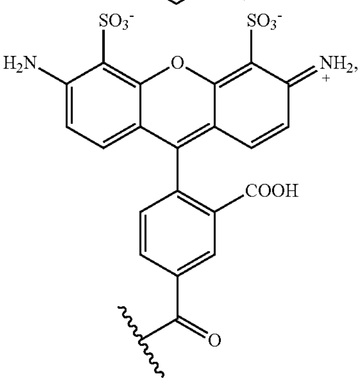
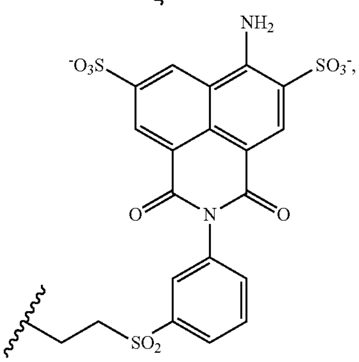
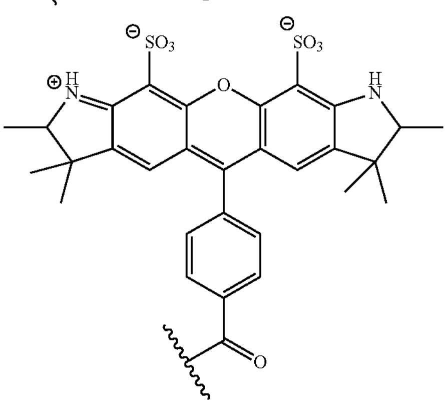
,
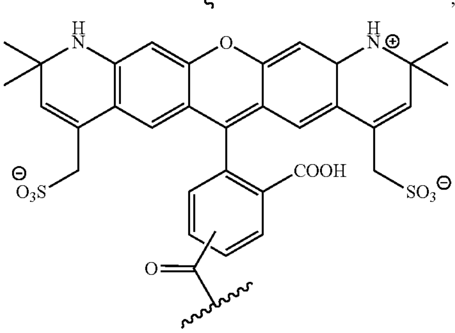
,
-continued
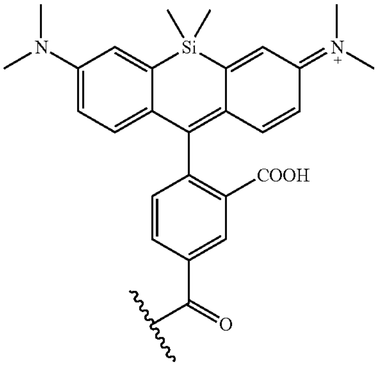
,
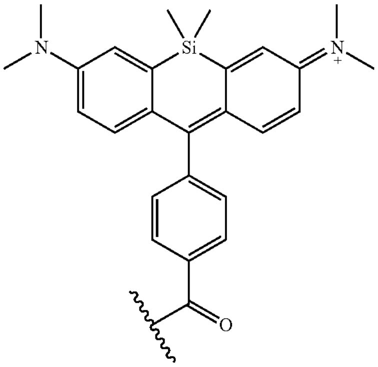
,
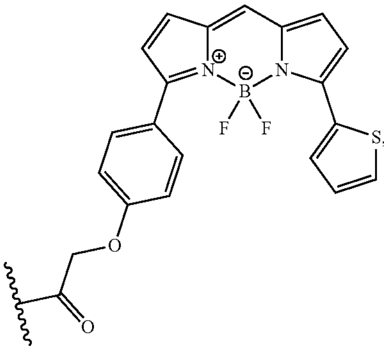
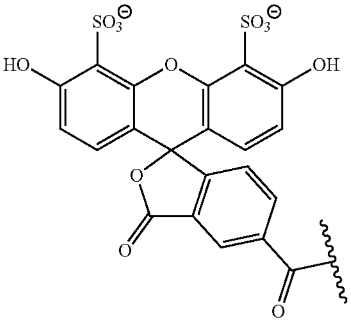
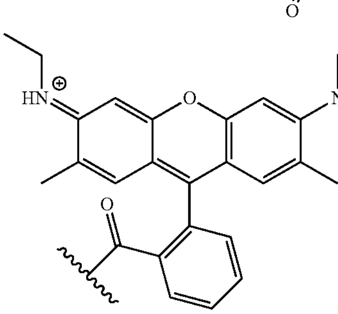
, -continued

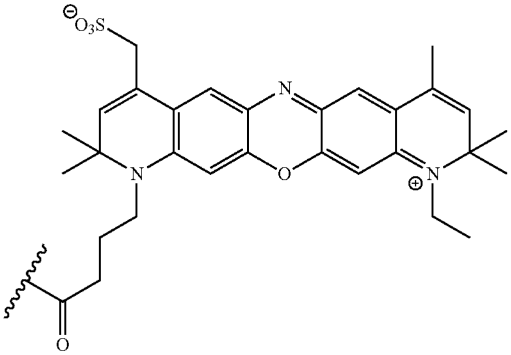

,

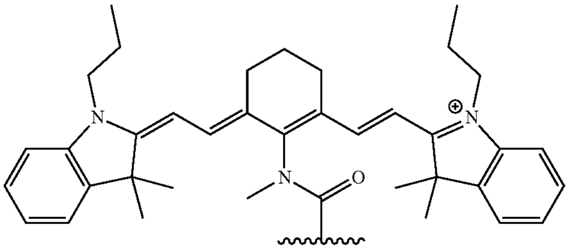

,

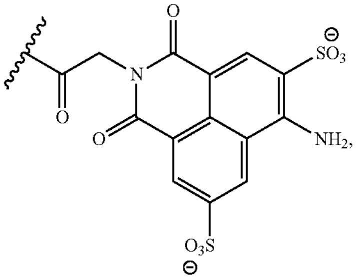

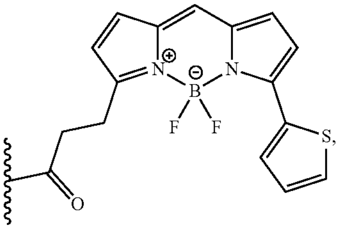

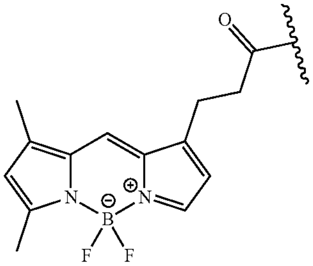

,

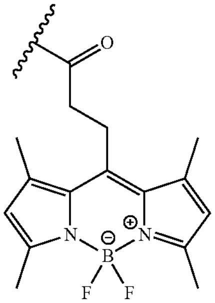

, and

-continued

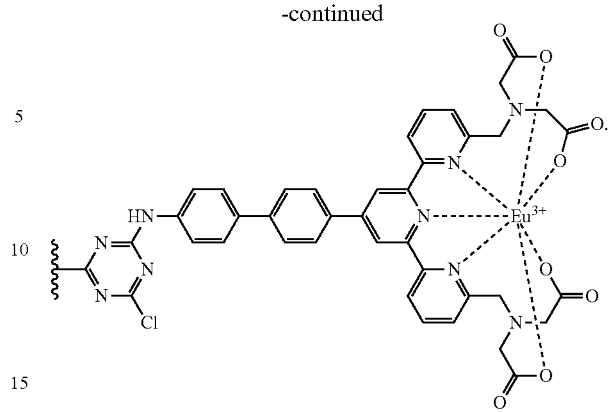

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45:13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", $5^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain advantages resulting from greater metabolic stability, for example increased in vivo half-life, and may therefore be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying examples using appropriate isotopically-labeled reagent in place of non-isotopically-labeled reagent.

A compound disclosed herein may be in the form of a salt. The salts may be prepared during the final isolation and purification of the compounds or separately, for example by reacting a basic group of the compound (e.g., an amino group) with a suitable acid or by reacting an acidic group of the compound (e.g., a carboxylic acid group) with a suitable base.

Acid salts may be prepared during the final isolation and purification of the compounds or separately by reacting a suitable group of the compound, such as an amino group, with a suitable acid. For example, a compound may be dissolved in a suitable solvent, such as but not limited to methanol and water, and treated with at least one equivalent of an acid, such hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

Compounds of formula (I) may be synthesized by a variety of methods, including those illustrated in Scheme 1, starting from the compound carboxypropylsulfopropyl-acridinium (CPSP-acridinium, 9-[N-tosyl-N-(3-carboxypropyl)]-10-(3-sulfopropyl) acridinium carboxamide), described by Adamczyk et al., *J. Org. Chem.* 1998, 63(16), 5636-5639.

Scheme 1.

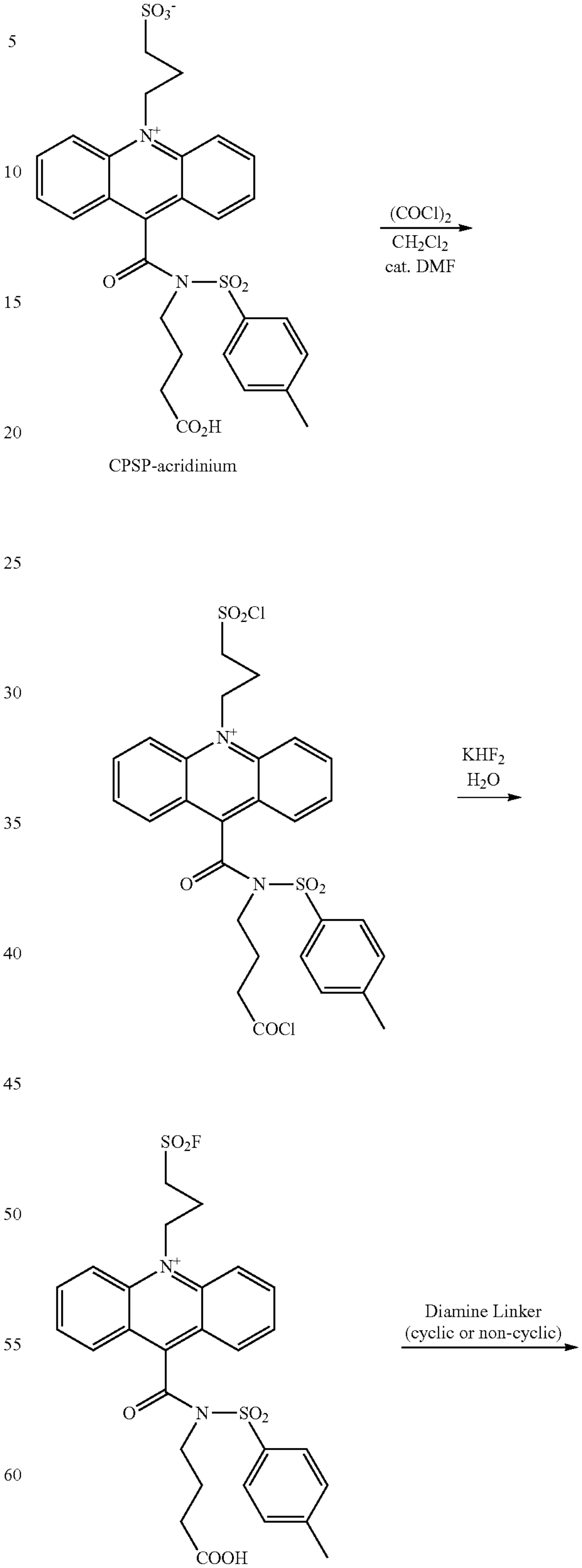

-continued

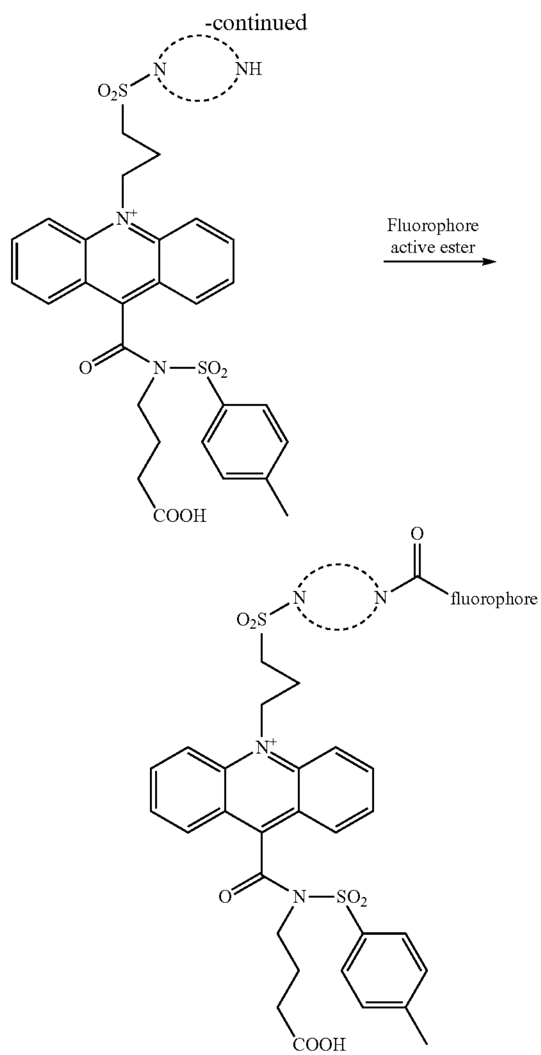

One skilled in the art will appreciate that Scheme 1 illustrate a synthesis of certain compounds with particular substituent groups (e.g., $R^1$, $R^2$, $L^1$, $L^2$, X, and Y groups), but that compounds with other groups at the corresponding positions can be prepared in similar ways.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the disclosure can be accomplished by methods analogous to those described in the synthetic schemes described herein and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

Thus, it will be apparent to one of ordinary skill in the art that the first and second conjugates described herein are of Formula (II):

(II)

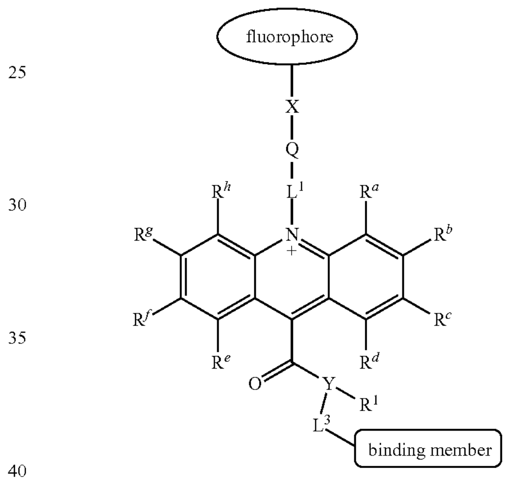

wherein: X is —NH— or a diamine linker; Y is selected from nitrogen, oxygen, and sulfur; when Y is nitrogen, $R^1$ is —$SO_2$-A, wherein A is selected from alkyl, alkenyl, alkynyl, aryl, heteroaryl, cycloalkyl, heterocyclyl, arylalkyl, heteroarylalkyl, cycloalkylalkyl, and heterocyclylalkyl; when Y is oxygen or sulfur, $R^1$ is absent; Q is —$SO_2$— or —CO—; $L^1$ is selected from alkylene and heteroalkylene; $L^3$ is a linker; $R^a$, $R^b$, $R^c$, $R^d$, $R^e$, $R^f$, $R^g$, and $R^h$ are each independently selected from hydrogen, $C_1$-$C_4$ alkyl, $C_1$-$C_4$ alkoxy, $C_1$-$C_4$ haloalkyl, $C_1$-$C_4$ haloalkoxy, halo, hydroxy, cyano, nitro, amino, carboxy, sulfonyl, phosphoryl, and selenyl; and the binding member is a molecule capable of binding to a target analyte; wherein each alkyl, alkenyl, alkynyl, aryl, heteroaryl, cycloalkyl, heterocyclyl, arylalkyl, heteroarylalkyl, cycloalkylalkyl, heterocyclylalkyl, alkylene, and heteroalkylene is independently optionally substituted with 1, 2, 3, 4, or 5 substituents.

The groups X, Y, $R^1$, A, $L^1$, $R^a$, $R^b$, $R^c$, $R^d$, $R^e$, $R^f$, $R^g$, Rh, and the fluorophore are the same as those described above for formula (I). Any group or combination of groups described above for compounds of formula (I) may also be included in a compound of formula (II).

In compounds of formula (II), $L^3$ is a linker. A wide variety of linkers can be used in the compounds of formula (II). In some embodiments, the linker may be a covalent bond. In some embodiments, the linker may be an alkylene linker, such as a $C_1$-$C_{40}$ alkylene linker, e.g., a $C_1$-$C_{30}$, $C_1$-$C_{20}$, $C_1$-$C_{12}$, $C_1$-$C_{10}$, $C_1$-$C_8$, $C_1$-$C_6$, or a $C_1$-$C_4$ alkylene linker. For example, the linker may be a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, or $C_{40}$ alkylene linker.

In some embodiments, the linker may be a heteroalkylene linker, such as a polyethylene glycol linker. Such a linker may have a formula $—(CH_2CH_2O)_{n1}—CH_2CH_2—$, where n1 is an integer from 1 to 20. For example, in some embodiments, n1 is an integer from 1 to 20, 1 to 18, 1 to 16, 1 to 14, 1 to 12, 1 to 10, 1 to 9, 1 to 8, 1 to 7, 1 to 6, 1 to 5, or 1 to 4. In some embodiments, n1 is 1, 2, 3, 4, 5, 6, 7, 8, 9, 10, 11, 12, 13, 14, 15, 16, 17, 18, 19, or 20.

In some embodiments, the linker may include a moiety E, wherein E is the product of a reaction between two reactive groups. For example, the group E may be an amide, an ester, a carbamate, a triazole, a sulfonamide, a phosphoramide, a phosphate, or a sulfate.

Analyte of Interest

The terms "analyte," "target analyte," and "analyte of interest," are used interchangeably herein and refer to the molecule, compound, or substance being measured in a particular assay. As will be appreciated by those in the art, any analyte that can be specifically bound by a binding member (e.g., a first specific binding member, a second specific binding member, a third specific binding member, and/or a fourth specific binding member) may be detected, and optionally quantified, using the kits and methods of the present disclosure.

In some embodiments, the analyte may be a biomolecule. Non-limiting examples of biomolecules include macromolecules such as proteins, lipids, and carbohydrates. In certain instances, analytes include hormones, antibodies, growth factors, cytokines, enzymes, receptors (e.g., neural, hormonal, nutrient, and cell surface receptors) or their ligands, cancer markers (e.g., PSA, TNF-alpha), markers of myocardial infarction (e.g., troponin, creatine kinase, and the like), toxins, drugs (e.g., drugs of addiction), metabolic agents (e.g., vitamins), and the like. Non-limiting embodiments of protein analytes include peptides, polypeptides, protein fragments, protein complexes, fusion proteins, recombinant proteins, phosphoproteins, glycoproteins, or lipoproteins.

In certain embodiments, the analyte may be a post-translationally modified protein (e.g., phosphorylated, methylated, glycosylated protein) and a corresponding binding member (described below) may be an antibody specific to a post-translational modification. A modified protein may be bound to a first binding member immobilized on a solid support where the first binding member binds to the modified protein but not the unmodified protein.

In some embodiments, the analyte may be a cell, such as, for example, a circulating tumor cell, pathogenic bacteria cell, or a fungal cell. In other embodiments, the analyte may be a virus (e.g., retrovirus, herpesvirus, adenovirus, lentivirus, Filovirus (Ebola), hepatitis virus (e.g., A, B, C, D, and E), or human papilloma virus (HPV)).

A non-limiting list of analytes that may be analyzed in accordance with the present disclosure include thyroglobulin, prolactin, Aβ42 amyloid beta-protein, fetuin-A, tau, secretogranin II, prion protein, alpha-synuclein, tau protein, neurofilament light chain, parkin, PTEN induced putative kinase 1, DJ-1, leucine-rich repeat kinase 2, mutated ATP13A2, Apo H, ceruloplasmin, peroxisome proliferator-activated receptor gamma coactivator-1 alpha (PGC-1a), transthyretin, vitamin D-binding protein, proapoptotic kinase R (PKR) and its phosphorylated PKR (pPKR), CXCL13, IL-12p40, CXCL13, IL-8, Dkk-3 (semen), p14 endocan fragment, serum, ACE2, autoantibody to CD25, hTERT, CAI25 (MUC 16), VEGF, sIL-2, osteopontin, human epididymis protein 4 (HE4), alpha-fetoprotein (AFP), albumin, albuminuria, microalbuminuria, neutrophil gelatinase-associated lipocalin (NGAL), interleukin 18 (IL-18), kidney injury molecule-1 (KIM-1), liver fatty acid binding protein (L-FABP), LMP1, BARF1, IL-8, carcinoembryonic antigen (CEA), BRAF, CCNI, EGRF, FGF19, FRS2, GREB1, LZTS1, alpha-amylase, carcinoembryonic antigen (CEA), CA125, interleukin-8 (IL-8), thioredoxin, beta-2 microglobulin, tumor necrosis factor-alpha receptors, CA15-3, follicle-stimulating hormone (FSH), leutinizing hormone (LH), T-cell lymphoma invasion and metastasis 1 (TIAM1), N-cadherin, EC39, amphiregulin, dUTPase, secretory gelsolin (pGSN), PSA (prostate specific antigen), thymosin β15, insulin, plasma C-peptide, glycosylated hemoglobin (HBA1c), C-Reactive Protein (CRP), interleukin-6 (IL-6), ARHGDIB (Rho GDP-dissociation inhibitor 2), CFL1 (cofilin-1), PFN1 (profilin-1), GSTP1 (glutathione S-transferase P), S100A11 (protein S100-A11), PRDX6 (peroxiredoxin-6), HSPE1 (10 kDa heat shock protein, mitochondrial), LYZ (lysozyme C precursor), GPI (glucose-6-phosphate isomerase), HIST2H2AA (histone H2A type 2-A), GAPDH (glyceraldehyde-3-phosphate dehydrogenase), HSPG2 (basement membrane-specific heparan sulfate proteoglycan core protein precursor), LGALS3BP (galectin-3-binding protein precursor), CTSD (cathepsin D precursor), APOE (apolipoprotein E precursor), IQGAP1 (Ras GTPase-activating-like protein IQGAP1), CP (Ceruloplasmin precursor), and IGLC2 (IGLC1 protein), PCDGF/GP88, EGFR, HER2, MUC4, IGF-IR, p27(kip1), Akt, HER3, HER4, PTEN, PIK3CA, SHIP, Grb2, Gab2, PDK-1 (3-phosphoinositide dependent protein kinase-1), TSC1, TSC2, mTOR, MIG-6 (ERBB receptor feedback inhibitor 1), S6K, src, KRAS, MEK mitogen-activated protein kinase 1, cMYC, TOPO II topoisomerase (DNA) II alpha 170 kDa, FRAP1, NRG1, ESR1, ESR2, PGR, CDKN1B, MAP2K1, NEDD4-1, FOXO3A, PPP1R1B, PXN, ELA2, CTNNB1, AR, EPHB2, KLF6; ANXA7, NKX3-1, PITX2, MKI67, PHLPP, adiponectin (ADIPOQ), fibrinogen alpha chain (FGA), leptin (LEP), advanced glycosylation end product-specific receptor (AGER or RAGE), alpha-2-HS-glycoprotein (AHSG), angiogenin (ANG), CD14 molecule (CD14), ferritin (FTH1), insulin-like growth factor binding protein 1 (IGFBP1), interleukin 2 receptor, alpha (IL2RA), vascular cell adhesion molecule 1 (VCAM1) and Von Willebrand factor (VWF), myeloperoxidase (MPO), IL1α, TNFα, perinuclear anti-neutrophil cytoplasmic antibody (p-ANCA), lactoferrin, calprotectin, Wilm's tumor-1 protein, aquaporin-1, MLL3, AMBP, VDAC1, *E. coli* enterotoxins (heat-labile exotoxin, heat-stable enterotoxin), influenza HA antigen, tetanus toxin, diphtheria toxin, botulinum toxins, Shiga toxin, Shiga-like toxin I, Shiga-like toxin II, *Clostridium difficile* toxins A and B, glial fibrillary acidic protein (GFAP), ubiquitin carboxy-terminal hydrolase L1 (UCH-L1), S100B, neurofilament light polypeptide (NF-L), Tau, pTau, Amyloid Beta 40 and 42, neuron-specific enolase (NSE), brain naturietic peptide (BNP), N-terminal (NT)-pro hormone BNP (NT-proBNP), CA19-9, placental growth factor (PIGF), sFlt-1, opioids, tacrolimus, protein induced by vitamin K absence-II (PIVKA-II), etc.

Other examples of analytes include drugs of abuse (e.g., cocaine), protein biomarkers (including, but not limited to, nucleolin, nuclear factor-kB essential modulator (NEMO), CD-30, protein tyrosine kinase 7 (PTK7), vascular endothelial growth factor (VEGF), MUC1 glycoform, immunoglobulin u Heavy Chains (IGHM), Immunoglobulin E, $\alpha v\beta 3$ integrin, $\alpha$-thrombin, HIV gp120, NF-$\kappa$B, E2F transcription factor, HER3, Plasminogen activator inhibitor, Tenascin C, CXCL12/SDF-1, prostate specific membrane antigen (PSMA), gastric cancer cells, and HGC-27); cells (including, but not limited to, non-small cell lung cancer (NSCLC), colorectal cancer cells, (DLD-1), H23 lung adenocarcinoma cells, Ramos cells, T-cell acute lymphoblastic leukemia (T-ALL) cells, CCRF-CEM, acute myeloid leukemia (AML) cells (HL60), small-cell lung cancer (SCLC) cells, NCIH69, human glioblastoma cells, U118-MG, PC-3 cells, HER-2-overexpressing human breast cancer cells, SK-BR-3, and pancreatic cancer cells (Mia-PaCa-2)); and infectious agents (including, but not limited to, *Mycobacterium tuberculosis, Staphylococcus aureus, Shigella dysenteriae, Escherichia coli* O157: H7, *Campylobacter jejuni, Listeria monocytogenes, Pseudomonas aeruginosa, Salmonella* O8, *Salmonella enteritidis*).

Interfering Substance(s)

As discussed above, in some embodiments the disclosed kits and methods are useful for detecting a substance which interferes with detection of the analyte in a sample. In such embodiments, the second specific binding member specifically binds a substance which interferes with detection of the analyte in a sample. Substances which interfere with analyte detection in an immunoassay, and the interpretation of results thereof (also referred to herein as "interfering substances," "cross-reactants," or "interferences"), are known in the art. Generally, interfering substances or cross-reactants can be categorized as substances that alter the measurable analyte concentration in the sample or substances that alter antibody binding (Tate, J. and G. Ward, *Clin. Biochem. Rev.,* 25 (2): 105-120 (2004)). Interferences or cross-reactants that alter measurable analyte concentration include, but are not limited to, hormone binding proteins, pre-analytical factors (e.g., anticoagulants, sample storage), and autoanalyte antibodies. Hormone binding globulins can alter the measurable analyte concentration in a sample either by their removal from or blocking of the analyte. For example, steroids can bind to sex hormone binding globulin or cortisol, causing decreased free analyte concentration (Slaats et al., *Clin Chem.,* 33:300-302 (1987); Masters, A. M. and Hahnel R, *Clin Chem.,* 35:979-84 (1989); and Vining, R. F., *Clin. Biochem. Rev.,* 2:39-49 (1981)). Pre-analytical factors that interfere with immunoassays include, but are not limited to, binding of cations present in serum (e.g., $Mg^{2+}$ or $Ca^{2+}$) to drugs or proteins which change antigen conformation and the measurable analyte concentration. Sample type also can affect analyte concentration, with differences in results for samples collected in lithium heparin, EDTA, and sodium fluoride/potassium oxalate or tubes without anticoagulant. Moreover, inappropriate sample type and specimen processing or storage can change the properties of a sample over time and affect results. Autoantibodies may cause interference in both non-immunoassay and immunoassay methods for several analytes, such as, for example, macro-enzymes (creatine kinase, amylase), thyroid hormones (Symons R. G., *Clin Biochem Rev.,* 10:44-49 (1989); Despres, N. and Grant, A. M., *Clin. Chem.,* 44(3): 440-54 (1998); and Sakata et al., *Ann. Intern. Med.,* 103(4): 579-89 (1985)), thyroglobulin (Despres and Grant, supra), insulin (Sapin, R., *Eur J Clin Chem Clin Biochem.,* 35(5): 365-7 (1997)); and Casesnoves et al., *Ann Clin Biochem.,* 35 (Pt 6): 768-74 (1998)), prolactin (Glezer et al., *Clin Endocrinol* (Oxf)., 57(1): 135-9 (2002)), and testosterone (Kuwahara et al., *J Clin Endocrinol Metab.,* 83(1): 14-6 (1998)).

Interferences or cross-reactants that alter antibody binding include, but are not limited to, heterophile antibodies, human anti-animal antibodies, and high-dose hook effect. Heterophile antibodies include natural antibodies and autoantibodies that are polyreactive against heterogeneous, poorly defined antigens of different chemical composition and generally show low affinity and weak binding (Levinson S. S., Miller J. J., *Clin. Chim Acta.,* 325(1-2): 1-15 (2002); and Bouvet et al., *J Immunol Methods,* 254(1-2): 199-201 (2001)). Heterophile antibodies may affect antigen binding to antibody in immunoassays by binding to the antigen and affecting analyte concentration, or by mimicking the binding of antigen due to its mirror-image structure. Human anti-animal antibodies (HAAA), including human anti-mouse antibodies (HAMA), are high affinity, specific polyclonal antibodies produced against a specific animal immunogen whole IgG or IgM immunoglobulin (Kricka L. J., *Clin Chem.,* 45:942-56 (1999)). HAAA show strong binding with antigen of a single chemical composition and are produced in high titers, such that they compete with the test antigen by cross-reacting with reagent antibodies of the same species to produce a false signal. In immunometric assay (IMA) systems where the analyte concentration range is large (e.g., ferritin, growth hormone, hCG, prolactin, and thyroglobulin), antigen-antibody reactions can go into antigen excess and can result in false-negative results (Ryall et al., *Anal Biochem.,* 127:308-315 (1982); Ohashi et al., *Horm Metab Res.,* 25:393-4 (1993); Sturgeon et al., *Ann Clin Biochem.,* 35:460-91 (1998); St-Jean et al., *Clin Endocrinol.,* 44:305-9 (1996); and Demers, L. M. and Spencer, C. A., *Thyroid,* 13:57-67 (2003)), potentially leading to misdiagnosis. In particular, for two-site immunoassays in which both the capture and detection antibody are added simultaneously, free analyte and analyte bound to labelled antibody compete for the limited number of antibody-binding sites, and in the presence of higher analyte concentration will decrease rather than increase label bound to the solid phase (referred to in the art as "high-dose hook effect").

The disclosed kits and methods may be used, for example, in thyroglobulin (Tg) immunoassays. Thyroglobulin (Tg) is a 660 kDa homodimeric glycoprotein. It is the most highly expressed protein in the thyroid gland and is present in both normal and malignant thyroid follicular cells. Tg serves as a protein scaffold for the synthesis of thyroxine and triiodothyronine as well as a storage protein for both thyroxine, triiodothyronine, and iodine. It has been identified as a tumor marker for post-operative management of patients with differentiated thyroid cancer. Rising levels of Tg post thyroidectomy and radioiodine ablation is highly suggestive of recurrent carcinoma. Interference in Tg immunoassays typically involves endogenous Tg antibody autoantibodies (TgAb), which are present in up to 30% of differentiated thyroid cancer patients (Hjiyiannakis et al., *Clin Oncol.,* 11:240-4 (1999)).

In other embodiments, the disclosed methods and kits may be used to detect interferents or cross-reactants in immunoassays for prolactin. Prolactin immunoassays are used in the art to aid in the diagnosis of male and female infertility and pituitary dysfunction, monitoring of male and female gonadal disorders, and management of amenorrhea and galactorrhea. The presence of anti-prolactin autoantibodies in the form of macroprolactin (macro-PRL) can cause hyperprolactinaemia without pituitary disease and may lead to unnecessary medical or surgical procedures (Glezer et al.,

*Clin Endocrinol.,* 57:135-9 (2002)). Macro-PRL (also referred to as "big-big prolactin") is primarily a macromolecular complex of prolactin (PRL) and an IgG antibody directed against specific epitope(s) on the PRL molecule (Fahie-Wilson, M. N., Ahlquist, J. A., *Clin. Endocrinol.,* 58, 683-5 (2003)). "Big-prolactin" is a dimeric form of prolactin. Both macroprolactin and big-prolactin are generally regarded as biologically inactive because of their decreased bioavailability. Therefore, the detection of big-prolactin and macroprolactin in an immunoassay represents a false positive result (Lippi, G. and Plebani, M., *Clin. Chem. Lab. Med.,* 54(4): 519-522 (2016); Suliman et al., *Clinical Chemistry,* 49(9): 1504-1509 (2003); and Vaishya et al., *J. Reprod. Infertil.,* 11(3): 161-167 (2010)). Currently, prolactin signal is measured via immunoassay and clinicians must interpret if a high result truly represents hyperprolactinemia (based on patient history, gestational stage, and other factors) or is a result of macroprolactin/big-prolactin interference. If macroprolactin/big-prolactin interference is suspected, the patient sample is manually treated with poly-ethylene glycol (PEG) to precipitate the larger species, followed by centrifugation (offline pre-treatment). Once the PEG treatment is complete, the supernatant of the treated sample is retested. The second prolactin result is then compared to the first, and a ratio between the first and second result is used to determine if macroprolactin/big prolactin interference is present. Thus, the disclosed kits and methods provide a more reliable and rapid assessment of the presence of macroprolactin/big-prolactin interferents.

In some embodiments, the interfering substance may be a biotin molecule. For example, in a "capture on the fly" immunoassay format, the capture antibody typically is labeled with biotin and the detection antibody typically is labeled with a reporter group (e.g., acridinium). After reacting with analyte, the immunocomplex is pulled down using streptavidin-coated microparticles. If the subject already has a high level of biotin present in their bloodstream, the amount of immunocomplex captured by the microparticles may be compromised, as the free biotin also binds to the streptavidin-coated microparticles and blocks binding by the immunocomplex. As such, false negatives and/or a reduced signal may result.

The solid support is contacted with a sample under conditions whereby an analyte of interest, if present in the sample, binds to the third specific binding member immobilized on the surface of the solid support, and to the first conjugate (e.g., a conjugate of Formula (II) disclosed herein), or, in some embodiments, to the first and second conjugates. In some embodiments, a substance that interferes with detection of the analyte, if present in the sample, binds to the third specific binding member immobilized on the surface of the solid support, and to the second conjugate (e.g., a conjugate of Formula (II) disclosed herein). The third specific binding member can concurrently bind to the analyte and the substance that interferes with detection of the analyte; however, a single specific third specific binding member may bind either the analyte or the interfering substance. In other words, the analyte and interfering substance cannot bind to the same single specific binding member. It will be appreciated that, of the plurality of third specific binding members that are immobilized on the solid support, some third specific binding members will bind to the analyte, and some will bind to the interfering substance.

In other embodiments, the substance that interferes with the detection of the analyte, if present in the sample, may bind the analyte directly, thereby preventing the first conjugate from accessing and binding the analyte. In such cases, the analyte is bound to the third specific binding member and the substance that interferes with detection of the analyte, the first conjugate binds to the analyte, and the second conjugate binds to the substance that interferes with detection of the analyte. In yet another configuration, the analyte may bind to the third specific binding member, the substance that interferes with detection of the analyte binds to the fourth specific binding member, the first conjugate binds to the analyte, and the second conjugate binds to the substance that interferes with detection of the analyte. In other embodiments, the interfering substance may prevent an analyte from binding to the third specific binding member (e.g., a capture antibody) immobilized on the solid support. Alternatively, the interfering substance may either bind to the analyte or the first conjugate, thereby preventing the first conjugate from binding to the captured analyte. In other embodiments, the interfering substance may bind to the analyte and disrupt a competitive assay format, such that the detected signal increases (e.g., first conjugate binds to the particle rather than to analyte), which would indicate an artificial increase in analyte concentration. Analyte interference scenarios are schematically illustrated in FIG. 8.

Solid Support

In certain embodiments, the disclosed kit comprises a third specific binding member and, optionally, a fourth specific binding member attached to, or immobilized on, a solid support. The terms "solid phase" and "solid support" are used interchangeably herein and refer to any material that can be used to attach and/or attract and immobilize one or more specific binding members. For example, a specific binding member can be the conjugate of Formula (II) disclosed herein. Any solid support known in the art can be used in the kits and methods described herein, including but not limited to, solid supports made out of polymeric materials in the form of planar substrates or beads. Examples of suitable solid supports include electrodes, test tubes, beads, microparticles, nanoparticles, wells of micro- or multi-well plates, gels, colloids, biological cells, sheets, and chips. In some embodiments, the solid support comprises two or more spatially separated electrodes. In certain embodiments, the solid support may be a particle, e.g., a microparticle. The terms "bead" and "particle" are used herein interchangeably and refer to a substantially spherical solid support. The terms "microparticle" and "microbead" are used interchangeably herein and refer to a microbead or microparticle that is allowed to occupy or settle in an array of wells, such as, for example, in an array of wells in a detection module. The microparticle or microbead may contain at least one specific binding member that binds to an analyte of interest, which specific binding member may or may not comprise a detectable label.

In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and 700 nm, or between about 500 nm and 700 nm. For example, the microparticle may be about 4-6 microns, about 2-3 microns, or about 0.5-1.5 microns. Particles less than about 500 nm may be referred to as "nanoparticles." Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

In certain embodiments, the solid support may be a magnetic bead or a magnetic particle. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include $NiFe_2O_4$, $CoFe_2O_4$, $Fe_3O_4$ (or $FeO \cdot Fe_2O_3$). Beads can have a solid core portion that is magnetic and is surrounded by one or more non-magnetic layers. Alternatively, the magnetic portion can be a layer around a non-magnetic core. The solid support on which a binding member is immobilized may be stored in dry or liquid form. The magnetic beads may be subjected to a magnetic field prior to or after contacting with the sample with a magnetic bead on which a binding member is immobilized.

The solid support may be contacted with a sample suspected of containing an analyte using any suitable method known in the art. The term "contacting," as used herein, refers to any type of combining action which brings a specific binding member immobilized thereon into sufficiently close proximity with an analyte of interest in a sample such that a binding interaction will occur if the analyte of interest specific for the binding member is present in the sample. Contacting may be achieved in a variety of different ways, including combining the sample with microparticles or exposing target analytes to microparticles comprising binding members by introducing the microparticles in close proximity to the analytes. The contacting may be repeated as many times as necessary.

In one embodiment, contact between the solid support and the sample volume is maintained (i.e., incubated) for a sufficient period of time to allow for the binding interaction between the specific binding members and analyte or interferent to occur. In this regard, for example, the sample volume may be incubated on a solid support for at least 30 seconds and at most 10 minutes. For example, the sample may be incubated with the solid support for about 1, 2, 3, 4, 5, 6, 7, 8, or 9 minutes. In another embodiment, the sample may be incubated with the microparticles for about 2 minutes. In addition, the incubating may be in a binding buffer that facilitates the specific binding interaction, such as, for example, albumin (e.g., BSA), non-ionic detergents (Tween-20, Triton X-100), and/or protease inhibitors (e.g., PMSF). The binding affinity and/or specificity of a specific binding member may be manipulated or altered in the assay by varying the binding buffer. In some embodiments, the binding affinity and/or specificity may be increased or decreased by varying the binding buffer. Other conditions for the binding interaction, such as, for example, temperature and salt concentration, may also be determined empirically or may be based on manufacturer's instructions. For example, the contacting may be carried out at room temperature (21° C.-28° C., e.g., 23° C.-25° C.), 37° C., or 4° C.

In certain embodiments, a solid support may also comprise a protective, blocking, or passivating layer that can eliminate or minimize non-specific attachment of non-capture components (e.g., analyte molecules, binding members) to the binding surface during the assay which may lead to false positive signals during detection or to loss of signal. Examples of materials that may be utilized in certain embodiments to form passivating layers include, but are not limited, to polymers (e.g., polyethylene glycol) that repel the non-specific binding of proteins; naturally occurring proteins (e.g., serum albumin and casein); surfactants (e.g., zwitterionic surfactants, sulfobetaines); naturally occurring long-chain lipids; polymer brushes, and nucleic acids, such as salmon sperm DNA.

Samples

The terms "sample," "test sample," and "biological sample" are used interchangeably herein and refer to a fluid sample containing or suspected of containing an analyte of interest. In some cases, the sample may comprise a liquid, fluent particulate solid, or fluid suspension of solid particles. In certain embodiments, the sample may be a liquid sample or a liquid extract of a solid sample. In some cases, the sample may be processed prior to the analysis described herein. For example, the sample may be separated or purified from its source prior to analysis; however, in certain embodiments, an unprocessed sample containing the analyte may be assayed directly. The sample may be derived from any suitable source. For example, the sample source may be synthetic (e.g., produced in a laboratory), the environment (e.g., air, soil, fluid samples, e.g., water supplies, etc.), an animal (e.g., a mammal), a plant, or any combination thereof. In a particular example, the sample is a human bodily substance (e.g., bodily fluid, blood, serum, plasma, urine, saliva, sweat, sputum, semen, mucus, lacrimal fluid, lymph fluid, amniotic fluid, interstitial fluid, lung lavage, cerebrospinal fluid, feces, tissue, or organ). Tissues may include, but are not limited, to skeletal muscle tissue, liver tissue, lung tissue, kidney tissue, myocardial tissue, brain tissue, bone marrow, cervix tissue, skin, etc. In certain cases, the source of the sample may be an organ or tissue, such as a biopsy sample, which may be solubilized by tissue disintegration/cell lysis.

In some cases, the fluid sample may be diluted prior to use in an assay. For example, in embodiments where the source of an analyte molecule is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use.

In some cases, as mentioned above, the sample may undergo pre-analytical processing. Pre-analytical processing may offer additional functionality such as nonspecific protein removal and/or effective yet cheaply implementable mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the sample is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

Method of Detecting an Interfering Substance

The disclosure provides a method of detecting a substance that interferes with detection of an analyte in a sample. In one aspect, the method comprises (a) contacting a sample suspected of comprising an analyte and a substance that interferes with detection of the analyte with any one of the aforementioned kits under conditions that allow: (i) binding of the analyte to the third specific binding member, (ii) specific binding of the substance that interferes with detection of the analyte to the third specific binding member, or non-specific binding of the substance that interferes with detection of the analyte to the solid support surface, (iii) binding of the first conjugate to the analyte, (iv) binding of the second conjugate to the substance that interferes with detection of the analyte; and optionally (v) binding of a fourth specific binding member to the substance that interferes with detection of the analyte; (b) detecting the signal intensities of the first detectable label and the second detectable label; and (c) detecting the presence of the substance that interferes with detection of the analyte in the sample by quantifying and analyzing the signal intensities of the first detectable label and the second detectable label.

In another aspect, the method comprises: (a) contacting a sample suspected of comprising an analyte and a substance that interferes with detection of the analyte with any one of the aforementioned kits under conditions that allow: (i) binding of the analyte to the third specific binding member and binding of the analyte to the substance that interferes with detection of the analyte to form an analyte-interferent complex, (ii) binding of the first conjugate to the analyte, and (iv) binding of the second conjugate to the substance that interferes with detection of the analyte or the analyte-interferent complex; and optionally (v) binding of a fourth specific binding member to the substance that interferes with detection of the analyte; (b) detecting the signal intensities of the first detectable label and the second detectable label; and (c) detecting the presence of the substance that interferes with detection of the analyte in the sample by quantifying and analyzing the signal intensities of the first detectable label and the second detectable label.

In a further aspect, the method comprises: (a) contacting a sample suspected of comprising an analyte and a substance that interferes with detection of the analyte with any one of the aforementioned kits under conditions that allow: (i) binding of the analyte to the third specific binding member, (ii) binding of the first conjugate to the analyte and binding of the first conjugate to the substance that interferes with detection of the analyte, and (iv) binding of the second conjugate to the substance that interferes with detection of the analyte; and optionally (v) binding of a fourth specific binding member to the substance that interferes with detection of the analyte; (b) detecting the signal intensities of the first detectable label and the second detectable label; and (c) detecting the presence of the substance that interferes with detection of the analyte in the sample by quantifying and analyzing the signal intensities of the first detectable label and the second detectable label.

In another aspect, the method comprises: (a) contacting a sample suspected of comprising an analyte and a substance that interferes with detection of the analyte with any one of the aforementioned kits under conditions that allow: (i) specific or non-specific binding of the analyte to the third specific binding member; (ii) specific or non-specific binding of the substance that interferes with detection of the analyte to the solid support surface, (iii) binding of the first conjugate to the analyte and specific or non-specific binding of the substance that interferes with detection of the analyte to the first conjugate, thereby increasing the amount of first conjugate available for detection, (iv) binding of the second conjugate to the substance that interferes with detection of the analyte; and (v) binding of a fourth specific binding member to the substance that interferes with detection of the analyte; (b) detecting the signal intensities of the first detectable label and the second detectable label; and (c) detecting the presence of the substance that interferes with detection of the analyte in the sample by quantifying and analyzing the signal intensities of the first detectable label and the second detectable label.

In embodiments where the interfering substance is a biotin molecule, as discussed above, the method of detecting the interfering biotin molecule comprises: (a) establishing a standard signal intensity (R value) of the first detectable label binding to the streptavidin-coated solid support in the absence of an interfering biotin molecule; (b) contacting a sample suspected of comprising both an analyte and a biotin molecule that interferes with detection of the analyte with the above-described kit under conditions that allow: (i) binding of the analyte to the first specific binding member to form a first complex; (ii) binding of the conjugate to the analyte bound to the first specific binding member to form immunocomplexes; and (iii) binding of the streptavidin-coated solid support to the biotin molecule attached to the first specific binding member and the biotin molecule which interferes with detection of the analyte in a sample; (c) detecting the signal intensities of the first detectable label and the second detectable label; (d) correcting for the signal intensity of the second detectable label; and (e) detecting the presence of the biotin molecule that interferes with detection of the analyte in the sample.

Descriptions of the specific binding members, conjugates, interfering substances, kits, analytes, and components thereof set forth above in connection with the disclosed kit also are applicable to the methods of detecting a substance that interferes with detection of an analyte in a sample.

In some embodiments, the first conjugate and the second conjugate (e.g., first and second conjugates of Formula (II) disclosed herein) may be contacted with the test sample in the same reaction mixture. In other embodiments, however, the first conjugate and the second conjugate may be contacted with the test sample in different reaction mixtures. In certain embodiments, the first and second binding members are used as detection antibodies as part of the first and second conjugates. In this regard, the first and second conjugates comprise different detectable labels with distinguishable spectroscopic properties (e.g., chemiluminescent emission signals of different wavelengths). Signals generated from the first and second specific binding members can be measured separately based on their spectroscopic properties. In certain embodiments, comparing the signal intensities of the first detectable label and the second detectable label comprises determining a ratio of the signal intensity of the first detectable label and the signal intensity of the second detectable label.

When the interfering substance is biotin, the method first comprises establishing a standard signal intensity (referred to as the "R value") of the first detectable label binding to the streptavidin-coated solid support in the absence of an interfering biotin molecule. It will be appreciated that an R value equal to the signal from the first detectable label detected in a sample, then the sample does not contain a biotin interferent. Following detection of the signal intensities of the first detectable label and the second detectable label, the amount of interfering biotin is determined by correcting for the signal intensity of the second detectable label. Such signal correction may be accomplished by, for example, multiplying the signal intensity of the second detectable label by the ratio R value and signal intensity of the first detectable label.

Method of Expanding Dynamic Range and Reducing Hook Effect

The disclosure also provides a method of expanding the dynamic range of an immunoassay, which method comprises: (a) contacting a test sample suspected of comprising an analyte with the above-described kit, wherein the analyte binds to the third specific binding member; (b) removing analyte not bound to the third specific binding member by washing; (c) binding the first conjugate to the analyte and the second conjugate to the analyte, wherein the first and second conjugates do not concurrently bind to the analyte; (d) removing first and second conjugates not bound to the analyte by washing; (e) measuring the signal intensities of the first detectable label and the second detectable label; and (f) determining the concentration of the analyte by comparing the signal intensities of the first detectable label and the second detectable label based on a flag value, whereby the dynamic range of the immunoassay is expanded.

The disclosure also provides a method of reducing hook effect and expanding the dynamic range of an immunoassay, which method comprises: (a) contacting a test sample suspected of comprising an analyte with the aforementioned kit, wherein the analyte binds to the third specific binding member and the first conjugate binds to the analyte; (b) removing any unbound analyte and unbound first conjugate by washing; (c) binding the second conjugate to the analyte, wherein the first and second conjugates do not concurrently bind to the analyte, (d) removing any unbound second conjugate by washing; (e) measuring the signal intensities of the first detectable label and the second detectable label; and (f) determining the concentration of the analyte based on a flag value, whereby hook effect of the immunoassay is reduced and dynamic range is expanded.

Descriptions of the specific binding members, conjugates, kits, analytes, and components thereof set forth above in connection with the disclosed kit also are applicable to the method of expanding the dynamic range of an immunoassay and reducing hook effect.

Generally, the assays and methods of expanding dynamic range described herein entail employing three specific binding members in a sandwich assay to eliminate “hook effect” in a one-step assay, or to expand linear assay dynamic range in two-step assay. Two of the three specific binding members are used for detection, but their relative binding affinities for the analyte may be different, e.g., as further described herein, and the first and second specific binding members bind to the third specific binding member via the analyte independently. In some embodiments, the first conjugate and the second conjugate (e.g., first and second conjugates of Formula (II) disclosed herein) may be contacted with the test sample in the same reaction mixture. In other embodiments, however, the first conjugate and the second conjugate may be contacted with the test sample in different reaction mixtures. In either case, the first conjugate and the second conjugate ideally are present in predetermined molar amounts that differ by less than about 100-fold. In some embodiments, the first analyte-binding molecule and the second analyte-binding molecule are present in predetermined molar amounts that differ by less than about 100-fold (e.g., from about 10-fold to about 100-fold, from about 10-fold to about 50-fold, from about 60-fold to about 100-fold, about 25-fold, about 50-fold, or about 75-fold). In some embodiments, the dynamic range of the assay comprises three or more orders of magnitude (e.g., 4, 5, 6, 7, 8, 9, 10 or more orders of magnitude).

For a one-step assay, in certain embodiments the first and second binding members are used as detection antibodies as part of the first and second conjugates. In this regard, the first and second conjugates comprises different detectable labels with distinguishable spectroscopic properties (e.g., chemiluminescent emission signals of different wavelengths). Signals generated from the first and second analyte-binding molecules can be measured separately based on their spectroscopic properties. The signal obtained from the first and second analyte-binding molecules can also be used as an indicator to choose the correct section of a calibration curve for concentration determination. In this regard, measuring the signal intensities of the first detectable label and the second detectable label may comprise performing a calibration assay over a predetermined range of analyte concentrations, and the method further comprises establishing a flag value. A flag value is the inflection point which separates the ascending section and descending section of the calibration curves from the first conjugate where the concavity changes from minus to plus.

For a one-step assay, when the signal intensity of the second detectable label in the test sample exceeds or equals the flag value, then the descending section of the calibration curve from the signal intensity of the first detectable label is used to determine analyte concentration. Alternatively, when the signal intensity of the second detectable label in the test sample is less than the flag value, then the ascending section of the calibration curve from the signal intensity of the first detectable label is used to determine analyte concentration. For a two-step assay, when the signal intensity of the second detectable label is less than the flag value, then the calibration curve from the signal intensity of the first detectable label is used to determine analyte concentration. Alternatively, when the signal intensity of the second detectable label is higher than the flag value, then the calibration curve from the signal intensity of the second detectable label is used to determine analyte concentration.

Analyte Analysis

The amount of analyte of interest present in the sample can be determined (e.g., quantified) using any suitable method known in the art. As discussed above, signals generated from the first and second detectable labels can be quantified and analyzed separately based on their spectroscopic properties. In other embodiments, signals generated from the first and second detectable labels can be quantified and analyzed by comparing the signal intensities of the first detectable label and the second detectable label (e.g., by determining a ratio of the signal intensity of the first detectable label and the signal intensity of the second detectable label).

As discussed herein, at least one of the first and second conjugates are detectably labeled with a compound comprising an acridinium moiety and a fluorophore that are linked via a rigid diamine linker. Thus, upon chemiluminescent triggering of the acridinium moiety, light output can be shifted to the emission wavelength of the attached fluorophore. The use of acridinium compounds as detectable labels in a homogeneous chemiluminescent assay is described in, e.g., Adamczyk et al, *Bioorg. Med. Chem. Lett.,* 16:1324-1328 (2006); Adamczyk et al, *Bioorg. Med. Chem. Lett.,* 4:2313-2317 (2004); Adamczyk et al, *Biorg. Med. Chem. Lett.,* 14:3917-3921 (2004); and Adamczyk et al, *Org. Lett.,* 5:3779-3782 (2003)). In one embodiment, chemiluminescent triggering of the acridinium moiety involves adding hydrogen peroxide to the biological sample prior to the detecting step. Hydrogen peroxide can be provided or supplied to the biological sample before, simultaneously with, or after the addition of specific binding member that comprises the above-described conjugate. The source of the hydrogen peroxide can be one or more buffers or other solutions that are known to contain hydrogen peroxide. In this regard, a solution of hydrogen peroxide can simply be added the biological sample.

The fluorescent or chemiluminescent signal from each specific binding member may be visualized and differentiated using any suitable device known in the art, including but not limited to, photo multiplier tubes (PMTs), photodiode arrays, or charge coupled device cameras. In some embodiments, these devices may be fitted with filters capable of differentiating per wavelength. For example, photo multiplier tubes with two-channel detection may be employed for multiplexing assays using different color chemiluminescent magnetic microparticle immunoassay (CMIA) conjugates. Such two-channel systems may also extend the dynamic range of single-color CMIA detection. By setting one of the PMTs to low gain/reduced amplification, or by inserting a neutral density filter that blocks, for example, about 99% of the light, and leaving the second PMT at the standard high gain, single-photon detection sensitivity may cover a combined dynamic range that is orders of magnitude larger as compared to only one PMT.

In some embodiments, the concentration of an analyte in a sample that may be substantially accurately determined is less than about 5000 fM (femtomolar), less than about 3000 fM, less than about 2000 fM, less than about 1000 fM, less than about 500 fM, less than about 300 fM, less than about 200 fM, less than about 100 fM, less than about 50 fM, less than about 25 fM, less than about 10 fM, less than about 5 fM, less than about 2 fM, less than about 1 fM, less than about 500 aM (attomolar), less than about 100 aM, less than about 10 aM, less than about 5 aM, less than about 1 aM, less than about 0.1 aM, less than about 500 zM (zeptomolar), less than about 100 zM, less than about 10 zM, less than about 5 zM, less than about 1 zM, less than about 0.1 zM, or less. For example, the concentration of analyte in the sample that may be substantially accurately determined is between about 5000 fM and about 0.1 fM, between about 3000 fM and about 0.1 fM, between about 1000 fM and about 0.1 fM, between about 1000 fM and about 0.1 zM, between about 100 fM and about 1 zM, between about 100 aM and about 0.1 zM, or a range defined by any of two of the foregoing values.

In some embodiments, the lower limit of detection (e.g., the lowest concentration of an analyte which may be determined in solution) is about 100 fM, about 50 fM, about 25 fM, about 10 fM, about 5 fM, about 2 fM, about 1 fM, about 500 aM (attomolar), about 100 aM, about 50 aM, about 10 aM, about 5 aM, about 1 aM, about 0.1 aM, about 500 zM (zeptomolar), about 100 zM, about 50 zM, about 10 zM, about 5 zM, about 1 zM, about 0.1 zM, or less.

The upper limit of detection (e.g., the upper concentration of an analyte which may be determined in solution) may be at least about 100 fM, at least about 1000 fM, at least about 10 pM (picomolar), at least about 100 μM, at least about 100 μM, at least about 10 nM (nanomolar), at least about 100 nM, at least about 1000 nM, at least about 10 μM, at least about 100 μM, at least about 1000 μM, at least about 10 mM, at least about 100 mM, at least about 1000 mM, or greater.

In some cases, the presence and/or concentration of the analyte in a sample may be detected rapidly, usually in less than about 1 hour, e.g., 45 minutes, 30 minutes, 15 minutes, 10 minutes, 5 minutes, 1 minute, or 30 seconds.

Adaptation of Kits and Methods for Particular Instruments

The concepts, kits, and methods as described herein can be implemented on any system or instrument, including any manual, automated or semi-automated systems. Ideally, the methods are performed using an automated or semi-automated system. Exemplary adaptations and systems for carrying out the disclosed methods are described below.

The kit (or components thereof), as well as the method of detecting a substance that interferes with detection of an analyte in a sample, as described herein, can be adapted for use in a variety of automated and semi-automated systems (including those wherein the solid support comprises an electrode or a microparticle). Illustrative automated and semi-automated systems are described in, e.g., U.S. Pat. Nos. 5,089,424 and 5,006,309, and are commercially marketed by, for example, Abbott Laboratories (Abbott Park, Ill.) as ARCHITECT®. The kits (or components thereof) and methods described herein may also be adapted for use in a variety of assay formats, such as, for example, one-step, delayed one-step, two-step, competitive, direct, and indirect formats (and combinations thereof). In direct formats (e.g., direct ELISA), an analyte (e.g., an antigen) is immobilized on a solid support (e.g., a multi-well pate). The analyte is then detected by an antibody directly conjugated to a detectable label (e.g., an enzyme). Indirect formats (e.g., and indirect ELISA) involve adsorbing an analyte (e.g., an antigen) to a solid support and detecting the analyte using a two-step process. First, an unlabeled primary antibody binds to the specific analyte. Second, a detectable label (e.g., an enzyme) conjugated to a secondary antibody that is directed against the host species of the primary antibody is applied.

Some of the differences between an automated or semi-automated system as compared to a non-automated system (e.g., ELISA) include the substrate to which a capture specific binding member (e.g., the third specific binding member described herein) is attached (which can impact sandwich formation and analyte reactivity), and the length and timing of the capture, detection, and/or any optional wash steps. Whereas a non-automated format such as an ELISA may require a relatively longer incubation time with sample and capture reagent (e.g., about two hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection specific binding member (e.g., the first and second detectable labels of the first and second conjugates described herein, respectively) for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories that may be used in connection with the disclosed methods include, but are not limited to, AXSYM®, IMX® (see, e.g., U.S. Pat. No. 5,294,404), PRISM®, EIA (bead), and QUANTUM™ II, as well as other platforms. Additionally, the assays, kits, and kit components described herein can be employed in other formats, for example, on electrochemical or other hand-held or point-of-care assay systems. The present disclosure is, for example, applicable to the commercial Abbott Point of Care (I-STAT®, Abbott Laboratories) electrochemical assay system that performs sandwich assays. Immunosensors and their methods of manufacture and operation in single-use test devices are described in, for example, U.S. Pat. No. 5,063,081, and U.S. Patent Application Publication Nos. 2003/0170881, 2004/0018577, 2005/0054078, and 2006/0160164.

In particular, with regard to the adaptation of an assay to the I-STAT® system, the following configuration may be useful. A microfabricated silicon chip is manufactured with a pair of gold amperometric working electrodes and a silver-silver chloride reference electrode. On one of the working electrodes, polystyrene beads (0.2 mm diameter) with immobilized high affinity capture analyte-binding molecule(s) are adhered to a polymer coating of patterned polyvinyl alcohol over the electrode. The immobilized lower affinity capture analyte-binding molecule(s) are adhered to the second electrode. This chip is assembled into an I-STAT® cartridge with a fluidics format suitable for assay. On a portion of the wall of the sample-holding chamber of the cartridge there is a layer comprising the detection analyte-binding molecule(s) labeled with alkaline phosphatase (or other label). Within the fluid pouch of the cartridge is an aqueous reagent that includes p-aminophenol phosphate.

In operation, a sample containing an analyte is added to the holding chamber of the test cartridge and the cartridge is inserted into the I-STAT® reader. After the detection specific binding member (e.g., the first or second specific binding member of the first or second conjugate, respectively) has dissolved into the sample, a pump element within the cartridge forces the sample into a conduit containing the chip. Here it is oscillated to promote formation of the sandwich between the capture specific binding member (e.g., the third specific binding member described herein), analyte, and the labeled detection specific binding member. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte in the sample by means of an embedded algorithm and factory-determined calibration curve.

The methods and kits described herein may comprise other reagents and involve additional steps for carrying out a particular assay. For example, various buffers may be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino) ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Pat. Nos. 8,445,199, 9,207,246, and 9,964,537, improved signal generation may be obtained, e.g., in an I-STAT® cartridge format, using a nucleic acid sequence linked to a detectable label or detection specific binding member as a signal amplifier.

In one embodiment, the methods described herein may be performed using a microfluidics device; such as a digital microfluidic (DMF) device. Any suitable microfluidics device known in the art can be used to perform the methods described herein, such as those described in, for example, International Patent Application Publication Nos. WO 2007/136386, WO 2009/111431, WO 2010/040227, WO 2011/137533, WO 2013/066441, WO 2014/062551, and WO 2014/066704, and U.S. Pat. No. 8,287,808. In certain cases, the device may be a lab-on-chip device, where analyte analysis may be carried out in a droplet of the sample containing or suspected of containing an analyte.

Many of the devices described above allow for the detection of a single molecule of an analyte of interest. Other devices and systems known in the art that allow for single molecule detection of one or more analytes of interest also can be used in the methods described herein. Such devices and systems include, for example, Quanterix SIMOA™ (Lexington, MA) technology, Singulex's single molecule counting (SMC™) technology (Alameda, CA, see for example, U.S. Pat. No. 9,239,284), and devices described in, for example, U.S. Patent Application Publication Nos. 2017/0153248 and 2018/0017552.

Generally, the present kits and methods can be employed for any purpose, e.g., for diagnosing, prognosticating, or assessing the efficacy of therapeutic/prophylactic treatment of a patient, among other uses.

The following examples further illustrate the invention but, of course, should not be construed as in any way limiting its scope.

Example 1

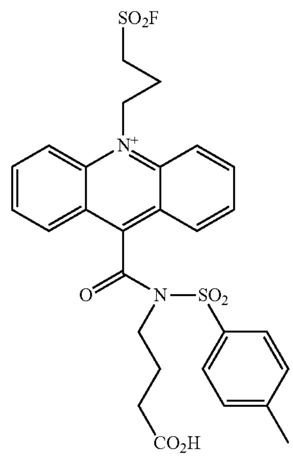 [SMILES: Cc1ccc(S(=O)(=O)N(CCCC(=O)O)C(=O)c2c3ccccc3[n+](CCCS(=O)(=O)F)c3ccccc23)cc1]

1.0 g (1.7 mmoles) of CPSP-acridinium (*J. Org. Chem.* 1998, 63, 5636-5639) was treated with 2 mL of $[COCl]_2$ (23 mmoles) in 25 mL of methylene chloride (DCM) followed by the addition of 5 μL of dimethylformamide. The slurry was stirred for 2 hours at room temperature and a yellow solution was obtained. After this time, the volatile components were removed from the reaction in vacuo on a rotary evaporator to give the di-acid chloride as a yellow gummy foam. The residue was re-dissolved in DCM (25 mL). A saturated aqueous solution of potassium bifluoride was prepared (15 mL) and added to the DCM solution. The two-phase system was stirred vigorously for 2 hours. After this time, the upper aqueous phase of the reaction was removed with a pipette and the lower DCM layer was evaporated in vacuo on a rotary evaporator. The resulting yellow solid was suspended in water (~25 mL) and filtered through a Buchner funnel. The solid was washed with small portions of cold water ~(65 mL). Yield 1.08 g of a yellow solid. MS (M+): calculated for $C_{28}H_{28}FN_2O_7S_2+$: Exact Mass: 587.13; Molecular Weight: 587.66. UPLC/MS measured 587.39.

Example 2

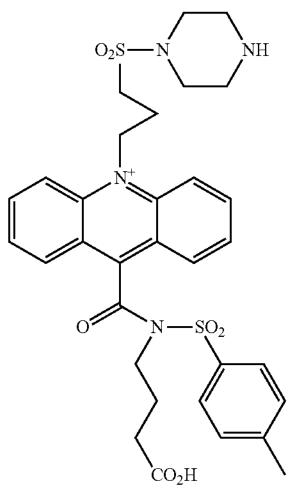 [SMILES: Cc1ccc(S(=O)(=O)N(CCCC(=O)O)C(=O)c2c3ccccc3[n+](CCCS(=O)(=O)N3CCNCC3)c3ccccc23)cc1]

A 25 mL round bottom flask equipped with a magnetic stir bar and nitrogen inlet was charged with 0.1 g (0.17 mmol) of the product from Example 1, DCM (10 mL) and then 0.14 g (1.7 mmol) of piperazine was added to the yellow slurry in one portion which resulted in a clear solution. The reaction was stirred for 5.5 days at room temperature. After this time, a milky white slurry was obtained. The reaction was evaporated to dryness in vacuo and the solids were dissolved in water (5 mL), methanol (5 mL) and 1 N HCl (2 mL). The resulting solution was purified by reverse phase HPLC using a YMC ODS AQ 50×250 mm I.D. steel column with a Waters Separations 2000 system monitored at 254 nm. Recorder chart speed 5 mm/min. A manual step gradient method (flow rate 70 mL/min) was used ACN/$H_2O$/$H_2O$-0.5 TFA. Fractions containing the product were combined and the volatile components were removed in vacuo on a rotary evaporator at 30° C. followed by high vacuum for 18 hours at room temperature. Yield 0.163 g of a yellow glass (titled compound as TFA salt). MS (M+): calculated for $C_{32}H_{37}N_4O_7S_2$+: Exact Mass: 653.21; Molecular Weight: 653.79. UPLC/MS measured 653.33.

Example 3

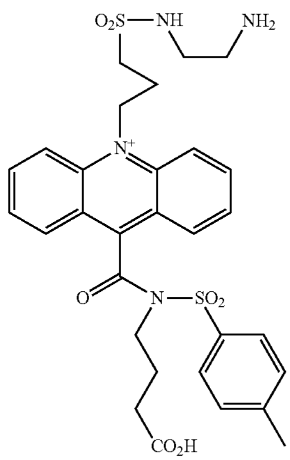 [SMILES: Cc1ccc(S(=O)(=O)N(CCCC(=O)O)C(=O)c2c3ccccc3[n+](CCCS(=O)(=O)NCCN)c3ccccc23)cc1]

The titled compound was prepared using the same procedure outlined for the preparation of Example 2 utilizing 0.1 g (0.17 mmol) of the product from Example 1, DCM (5 mL) and 0.057 mL (0.85 mmol) of ethylene diamine (EDA). Yield 0.027 g of a yellow film (titled compound as TFA salt). MS (M+): calculated for $C_{30}H_{35}N_4O_7S_2$+; Exact Mass: 627.1942; Molecular Weight: 627.7510. UPLC/MS measured 627.43.

Example 4

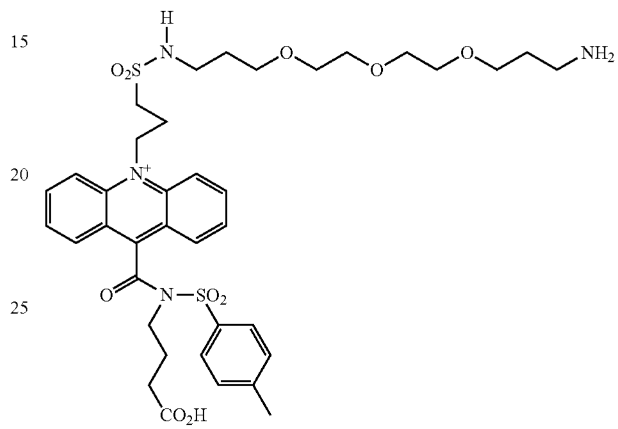

The titled compound was prepared using the same procedure outlined for the preparation of Example 2 utilizing 0.026 g (0.044 mmol) of the product from Example 1, DCM (5 mL) and 0.1 mL (0.45 mmol) of 4,7,10-trioxa-1,13-tridecanediamine. Yield 0.018 g of a yellow film (titled compound as TFA salt). MS (M+): calculated for $C_{38}H_{51}N_4O_{10}S_2$+: Exact Mass: 787.3041; Molecular Weight: 787.9618. UPLC/MS measured 787.53.

Example 5

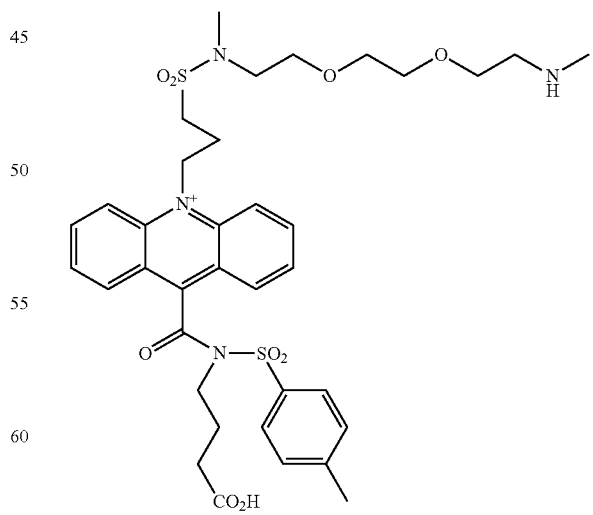

The titled compound was prepared using the same procedure outlined for the preparation of Example 2 utilizing 0.03 g (0.051 mmol) of the product from Example 1, DCM (1 mL) and 0.1 g (0.57 mmol) of 1,8-bis(methylamino)-3,6-dioxaoctane. Yield 0.016 g of a yellow film (titled compound as TFA salt). MS (M+): calculated for $C_{36}H_{47}N_4O_9S_2$+: Exact Mass: 743.2779; Molecular Weight: 743.9092. UPLC/MS measured 743.39.

Example 6

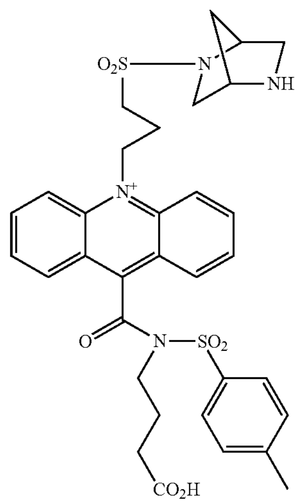 [SMILES: Cc1ccc(S(=O)(=O)N(CCCC(=O)O)C(=O)c2c3ccccc3[n+](CCCS(=O)(=O)N3CC4CC3CN4)c3ccccc23)cc1]

A 5 mL round bottom flask equipped with a magnetic stir bar and nitrogen inlet was charged with 0.015 g (0.026 mmol) of the product from Example 1, DMF (1 mL), N,N-diisopropylethylamine (DIEA) (0.34 mL, 2 mmol) and then (1S,4S)-(+)-2,5-diazabicyclo[2.2.1]heptane dihydrobromide (0.14 g, 0.52 mmol) was added in one portion. The reaction was stirred for 2 days at room temperature. The entire solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5 TFA.

Fractions containing the product were combined and the volatile components were removed in vacuo on a rotary evaporator at 30° C. followed by high vacuum for 18 hours at room temperature. Yield 0.0084 g of a yellow film (titled compound as TFA salt). MS (M+): calculated for $C_{33}H_{37}N_4O_7S_2$+: Exact Mass: 665.2098; Molecular Weight: 665.7989. UPLC/MS measured 665.20.

Example 7

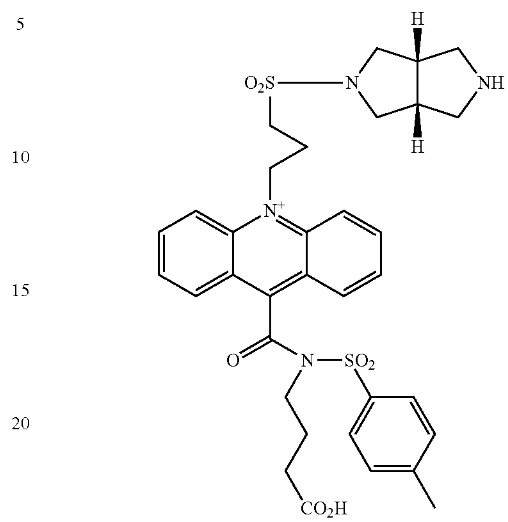

A 5 mL round bottom flask equipped with a magnetic stir bar and nitrogen inlet was charged with 0.015 g (0.026 mmol) of the product from Example 1, DCM (0.5 mL), DIEA (0.17 mL, 1 mmol) and then (cis-racemic0-tert-butyl hexahydropyrrolo[3,4-c]pyrrole-2(1H)-carboxylate (0.055 g, 0.26 mmol) was added to the yellow slurry in one portion. The reaction was stirred for 18 hours at room temperature. The reaction was evaporated to dryness using a stream of nitrogen and then dissolved in a small amount of MeOH. The entire solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5 formic acid. Fractions containing the product were combined and the volatile components were removed in vacuo on a rotary evaporator at 30° C. followed by high vacuum for 18 hours at room temperature. Yield 0.0205 g of a yellow film (Boc protected amine intermediate). MS (M+): calculated for $C_{39}H_{47}N_4O_9S_2$+: Exact Mass: 779.2779; Molecular Weight: 779.9413. UPLC/MS measured 779.16.

A 4 mL vial equipped with a magnetic stir bar was charged with the Boc-protected amine intermediate and DCM (0.5 mL). Trifluoroacetic acid (TFA) (0.5 mL) was added and the mixture was stirred for 1 hour at RT. The reaction was evaporated to dryness using a stream of nitrogen overnight. The crude product was dissolved in a small amount of MeOH. The entire solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5 TFA. Fractions containing the product were combined and the volatile components were removed in vacuo on a rotary evaporator at 30° C. followed by high vacuum for 18 hours at room temperature. Yield 0.0175 g of a yellow film (titled compound as TFA salt). MS (M+): calculated for $C_{34}H_{39}N_4O_7S_2$+: Exact Mass: 679.2255; Molecular Weight: 679.8255. UPLC/MS measured 679.24.

Example 8

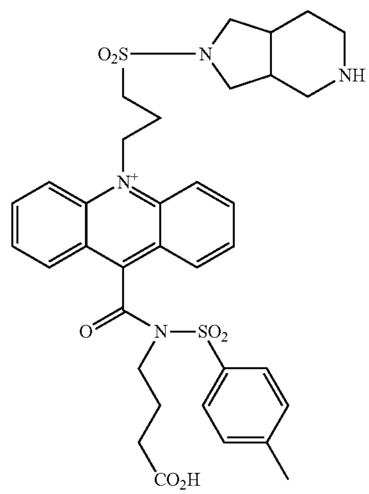 [SMILES: Cc1ccc(S(=O)(=O)N(CCCC(=O)O)C(=O)c2c3ccccc3[n+](CCCS(=O)(=O)N3CC4CCNCC4C3)c3ccccc23)cc1]

The titled compound was prepared using the same procedure outlined for the preparation of Example 7 utilizing 0.015 g (0.026 mmol) of the product from Example 1, 5-Boc-octahydro-pyrrolo[3,4-c]pyridine (0.01 g, 0.044 mmol), DCM (0.5 mL for the amine coupling and 0.5 mL for the de-protection step), DIEA (for amine coupling, 0.17 mL, 1 mmol), and TFA (for Boc deprotection, 0.5 mL). Yield 0.0074 g of a yellow film (Boc protected amine intermediate). MS (M+): calculated for $C_{40}H_{49}N_4O_9S_2$+: Exact Mass: 793.2935; Molecular Weight: 793.9679. UPLC/MS measured 793.20.

Yield 0.0077 g of a yellow film (titled compound as TFA salt). MS (M+): calculated for $C_{35}H_{41}N_4O_7S_2$+: Exact Mass: 693.2411; Molecular Weight: 693.8521. UPLC/MS measured 693.20.

Example 9

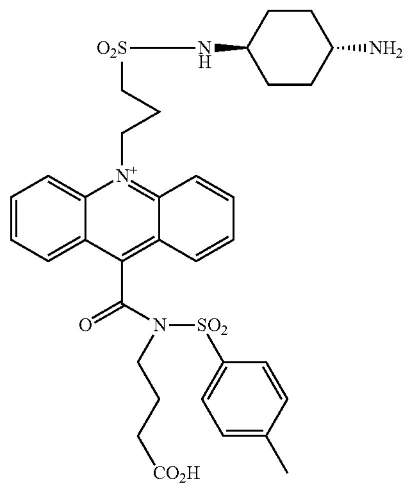 [SMILES: Cc1ccc(S(=O)(=O)N(CCCC(=O)O)C(=O)c2c3ccccc3[n+](CCCS(=O)(=O)N[C@H]3CC[C@H](N)CC3)c3ccccc23)cc1]

A 5 mL round bottom flask equipped with a magnetic stir bar and nitrogen inlet was charged with 0.015 g (0.026 mmol) of the product from Example 1, DCM (0.5 mL) and DIEA (0.17 mL, 1 mmol). trans-1,2-diaminocyclohexane was added to the yellow slurry in one portion. The reaction was stirred for 18 hours at room temperature. The reaction was evaporated to dryness using a stream of nitrogen and then dissolved in a small amount of MeOH. The entire solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.010 g of a yellow film (titled compound as TFA salt). MS (M+): calculated for $C_{34}H_{41}N_4O_7S_2$+: Exact Mass: 681.2411; Molecular Weight: 681.8414. UPLC/MS measured 681.27.

Example 10

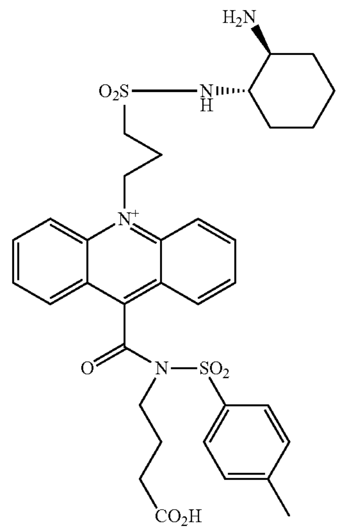 [SMILES: Cc1ccc(S(=O)(=O)N(CCCC(=O)O)C(=O)c2c3ccccc3[n+](CCCS(=O)(=O)N[C@H]3CCCC[C@@H]3N)c3ccccc23)cc1]

The titled compound was prepared using the same procedure outlined for the preparation of Example 9 utilizing 0.015 g (0.026 mmol) of the product from Example 1, DCM (0.5 mL), DIEA (0.17 mL, 1 mmol) and (+−)-trans-1,2-diaminocyclohexane (0.029 g, 0.26 mmol). Yield 0.0154 g of a yellow film (titled compound as TFA salt). MS (M+): calculated for $C_{34}H_{41}N_4O_7S_2$+: Exact Mass: 681.2411; Molecular Weight: 681.8414. UPLC/MS measured 681.34.

Example 11

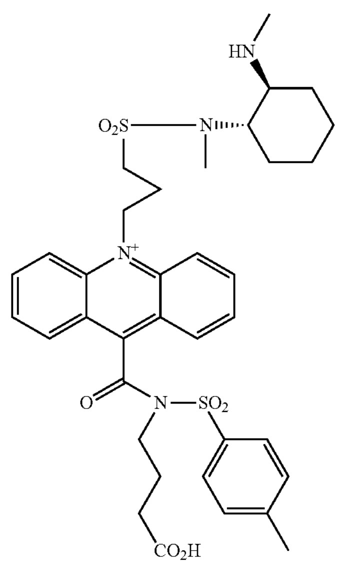 [SMILES: CN[C@H]1CCCC[C@@H]1N(C)S(=O)(=O)CCC[n+]1c2ccccc2c(C(=O)N(CCCC(=O)O)S(=O)(=O)c2ccc(C)cc2)c2ccccc21]

The titled compound was prepared using the same procedure outlined for the preparation of Example 9 utilizing 0.015 g (0.026 mmol) of the product from Example 1, DCM (0.5 mL), DIEA (0.17 mL, 1 mmol) and (S,S)-(+)-n,N'-dimethyl-1,2-cyclohexanediamine (0.037 g, 0.26 mmol). Yield 0.0056 g of a yellow film (titled compound as TFA salt). MS (M+): calculated for $C_{36}H_{45}N_4O_7S_2$+: Exact Mass: 709.2724; Molecular Weight: 709.8946. UPLC/MS measured 709.27.

Example 12

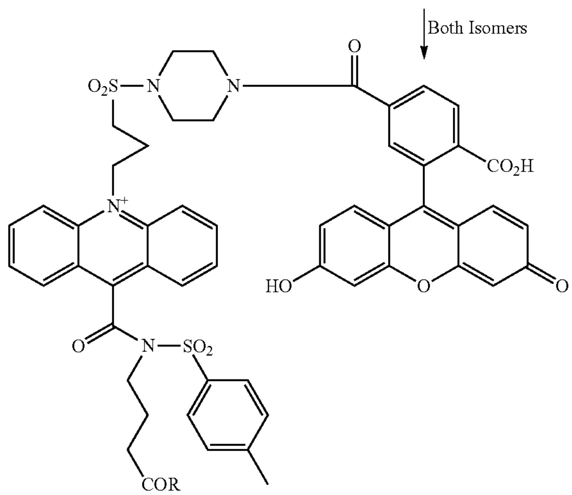

-continued

R = —OH

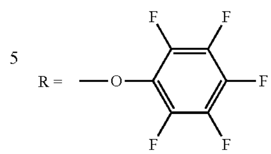

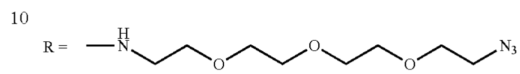

A 5 mL round bottom flask equipped with a magnetic stir bar and nitrogen inlet was charged with 0.005 g (0.0065 mmol) of the product from Example 2, DMF (0.5 mL) and 0.01 g (0.021 mmol) of a mixture of (5) 6-carboxyfluorescein-NHS esters followed by the addition of DIEA (0.05 mL, 0.28 mmol). The reaction was stirred at room temperature for 2.5 days. A few drops of water were added and the mixture was stirred at room temperature for 30 minutes. The reaction was diluted with MeOH (2 mL) and purified by reverse phase HPLC using a YMC ODS AQ 30×150 mm steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5 TFA. The fractions containing the products were combined and volatile components were removed in vacuo on a rotary evaporator at 30° C. and dried under high vacuum (1 mm Hg) over 2 hours. Yield 0.0012 g of a yellow film (titled compound). MS (M+): calculated for $C_{53}H_{47}N_4O_{13}S_2$+: Exact Mass: 1011.2576; Molecular Weight: 1012.0887. UPLC/MS measured 1011.39.

A 5 mL round bottom flask equipped with a magnetic stir bar and nitrogen inlet was charged with 0.012 g of the product from the above step, DMF (0.5 mL) and Pyridine ((0.5 mL, 0.62 mmol). Pentafluorophenyl trifluoroacetate (0.05 mL, 0.3 mmol) was then added to the mixture in one portion and the reaction was stirred at RT for 1 hr. The volatile components were removed from the mixture in vacuo and the residue was triturated 5× with 1:1 ether-hexane and the trace volatile components were removed under high vacuum (1 mm Hg) over 2 hours. Yield 0.008 g of a yellow film (titled compound, R=—O-pentafluorophenyl). MS (M+): calculated for $C_{59}H_{46}F_5N_4O_{13}S_2$+: Exact Mass: 1177.2417; Molecular Weight: 1178.1370. UPLC/MS measured 1177.21. The product was split into 2 equal portions for the next reaction and for conjugation.

0.004 g of the pentafluorophenyl ester product from the last step was dissolved in DCM (0.5 mL). Azido-dPEG3-amine (0.1 g, 0.45 mmol) in DCM (0.5 mL) was then added dropwise and the reaction mixture was stirred for one hour at RT. The volatile components were removed from the reaction mixture under a stream of nitrogen over 18 hours. The reaction mixture was diluted with MeOH (1 mL) and water (1 mL) and purified by reverse phase HPLC by elution on a YMC ODS AQ 30×150 mm steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% TFA. Fractions containing the product were combined and the volatile components were removed in vacuo on a rotary evaporator at 30° C. and dried under high vacuum (1 mm Hg) over 18 hours. Yield 0.007 g yellow film (titled compound, R=—O-PEG-Azide). MS (M+): calculated for $C_{61}H_{63}N_8O_{15}S_2$+: Exact Mass: 1211.3849; Molecular Weight: 1212.3270. UPLC/MS measured 1211.47.

Example 13

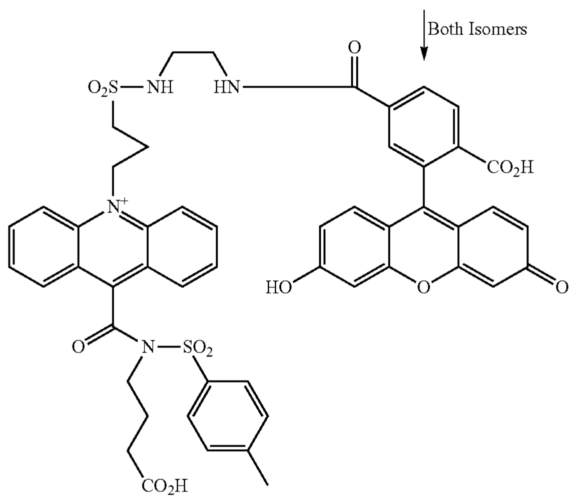 [SMILES: Cc1ccc(S(=O)(=O)N(CCCC(=O)O)C(=O)c2c3ccccc3[n+](CCCS(=O)(=O)NCCNC(=O)c3ccc(C(=O)O)c(-c4c5ccc(=O)cc-5oc5cc(O)ccc45)c3)c3ccccc23)cc1]

The titled compound was prepared using the same procedure outlined for the preparation of Example 12 utilizing 0.039 g (0.049 mmol) of the product from Example 3, DMF (2.0 mL), 0.028 g (0.06 mmol) of a mixture of (5) 6-carboxyfluorescein-NHS esters and DIEA (0.1 mL, 0.6 mmol). Yield 0.008 g of a yellow film (titled compound). MS (M+): calculated for $C_{51}H_{45}N_4O_{13}S_2$+: Exact Mass: 985.2419; Molecular Weight: 986.0515. UPLC/MS measured 985.49.

Example 14

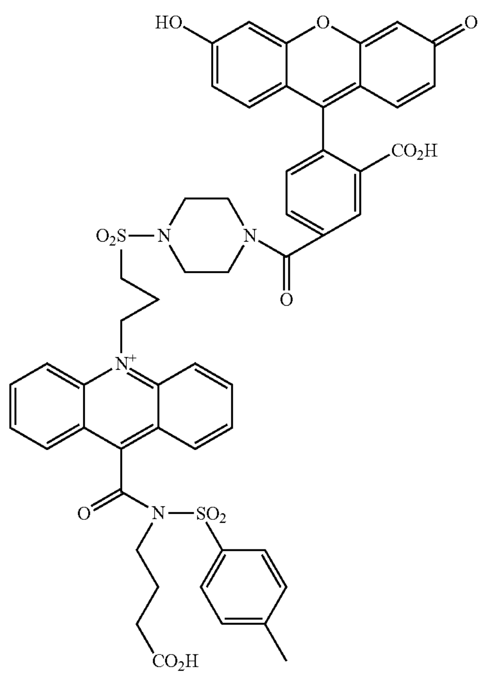 [SMILES: Cc1ccc(S(=O)(=O)N(CCCC(=O)O)C(=O)c2c3ccccc3[n+](CCCS(=O)(=O)N3CCN(C(=O)c4ccc(-c5c6ccc(=O)cc-6oc6cc(O)ccc56)c(C(=O)O)c4)CC3)c3ccccc23)cc1]

The titled compound was prepared using the same procedure outlined for the preparation of Example 12 utilizing 0.01 g (0.013 mmol) of the product from Example 2, DMF (0.25 mL), 0.03 g (0.055 mmol) of 5-carboxyfluorescein-PFP ester (from 5-carboxyfluorescein and pentafluorophenyl trifluoroacetate) and DIEA (0.025 mL, 0.055 mmol). Yield 0.0018 g of a yellow film (titled compound). MS (M+): calculated for $C_{53}H_{47}N_4O_{13}S_2$+: Exact Mass: 1011.2576; Molecular Weight: 1012.0887. UPLC/MS measured 1011.38.

Example 15

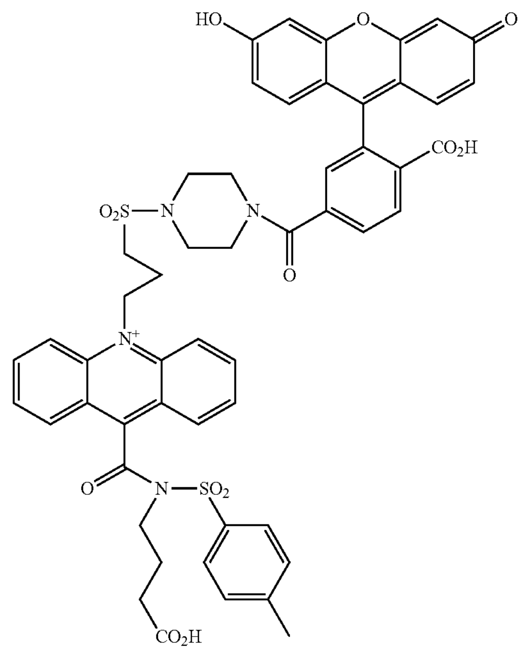 [SMILES: Cc1ccc(S(=O)(=O)N(CCCC(=O)O)C(=O)c2c3ccccc3[n+](CCCS(=O)(=O)N3CCN(C(=O)c4ccc(C(=O)O)c(-c5c6ccc(=O)cc-6oc6cc(O)ccc56)c4)CC3)c3ccccc23)cc1]

The titled compound was prepared using the same procedure outlined for the preparation of Example 12 utilizing 0.01 g (0.013 mmol) of the product from Example 2, DMF (0.25 mL), 0.03 g (0.055 mmol) of 6-carboxyfluorescein-PFP ester (from 6-carboxyfluorescein and pentafluorophenyl trifluoroacetate) and DIEA (0.025 mL, 0.055 mmol). Yield 0.0029 g of a yellow film (titled compound). MS (M+): calculated for $C_{53}H_{47}N_4O_{13}S_2$+: Exact Mass: 1011.2576; Molecular Weight: 1012.0887. UPLC/MS measured 1011.45.

Example 16

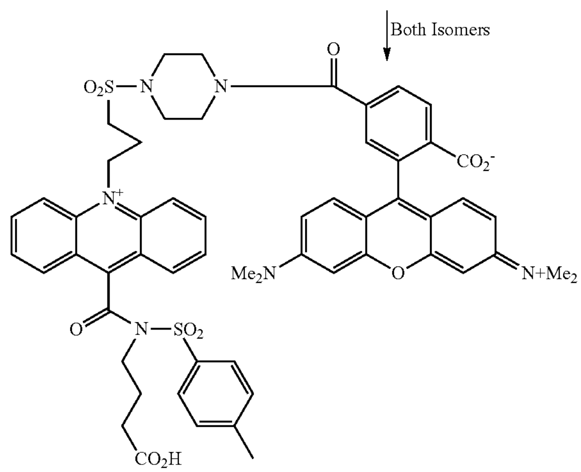

The titled compound was prepared using the same procedure outlined for the preparation of Example 12 utilizing 0.01 g (0.013 mmol) of the product from Example 2, DMF (0.25 mL), 0.011 g (0.021 mmol) of a mixture of (5) 6-TAMRA™-NHS esters and DIEA (0.025 mL, 0.055 mmol). Individual product isomers were separated during purification. Yield isomer A from fraction 9:0.002 g purple film (titled compound). MS (M+): calculated for $C_{57}H_{57}N_6O_{11}S_2$+: Exact Mass: 1065.3521; Molecular Weight: 1066.2255. UPLC/MS measured 1065.55 (weak); M++ 533.45 (strong).

Yield isomer B from fraction 10: 0.002 g purple film (titled compound). MS (M+): calculated for $C_{57}H_{57}N_6O_{11}S_2$+: Exact Mass: 1065.3521; Molecular Weight: 1066.2255. UPLC/MS measured 1065.48 (weak); M++ 533.45 (strong).

Example 17

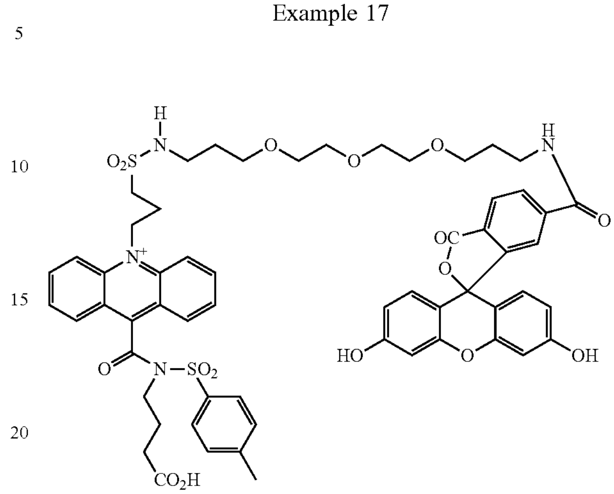

The titled compound was prepared using the same procedure outlined for the preparation of Example 12 utilizing 0.01 g (0.011 mmol) of the product from Example 4, DMF (0.25 mL), 0.014 g (0.026 mmol) of 6-carboxyfluorescein-PFP ester (prepared from 6-carboxyfluorescein and pentafluorophenyl trifluoroacetate) and DIEA (0.025 mL, 0.055 mmol). Yield 0.005 g of a yellow film (titled compound). MS (M+): calculated for $C_{59}H_{61}N_4O_{16}S_2$+: Exact Mass: 1145.3518; Molecular Weight: 1146.2623. UPLC/MS measured 1145.30.

Example 18

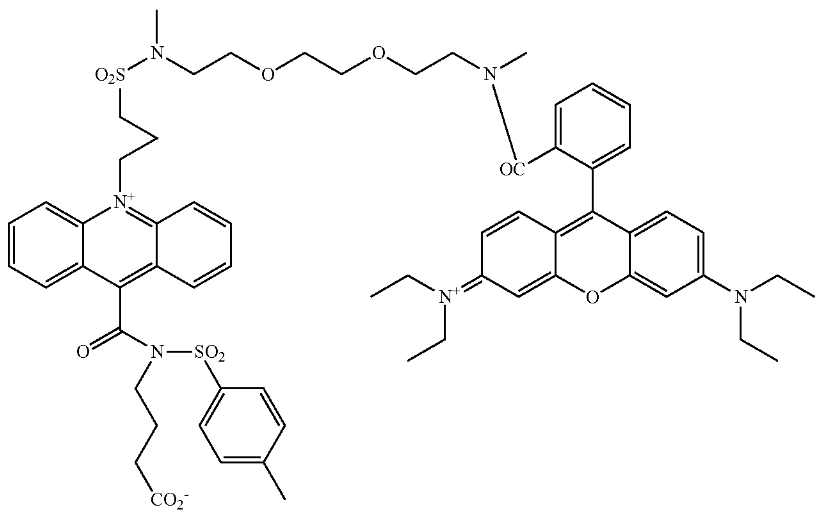

The titled compound was prepared using the same procedure outlined for the preparation of Example 12 utilizing 0.0049 g (0.0057 mmol) of the product from Example 5, DMF (0.25 mL), 0.01 g (0.016 mmol) of rhodamine B-PFP ester (prepared from rhodamine B and pentafluorophenyl trifluoroacetate) and DIEA (0.025 mL, 0.055 mmol). Yield 0.0016 g of a purple film (titled compound). MS (M+): calculated for $C_{64}H_{75}N_6O_{11}S_2$+: Exact Mass: 1167.49; Molecular Weight: 1168.45. UPLC/MS measured 1167.61.

Example 19

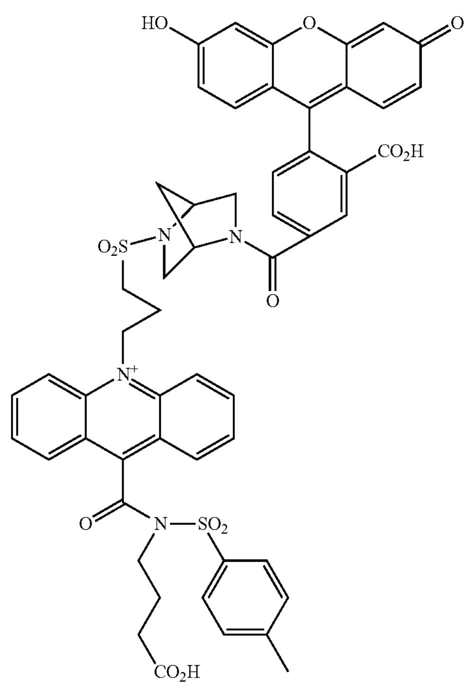 [SMILES: Cc1ccc(S(=O)(=O)N(CCCC(=O)O)C(=O)c2c3ccccc3[n+](CCCS(=O)(=O)N3CC4CC3CN4C(=O)c3ccc(-c4c5ccc(=O)cc-5oc5cc(O)ccc45)c(C(=O)O)c3)c3ccccc23)cc1]

The titled compound was prepared using the same procedure outlined for the preparation of Example 12 utilizing 0.0042 g (0.0054 mmol) of the product from Example 6, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0048 g of an orange yellow film (titled compound). MS (M+): calculated for $C_{54}H_{47}N_4O_{13}S_2$+: Exact Mass: 1023.2576; Molecular Weight: 1024.0994. UPLC/MS measured 1023.22.

Example 20

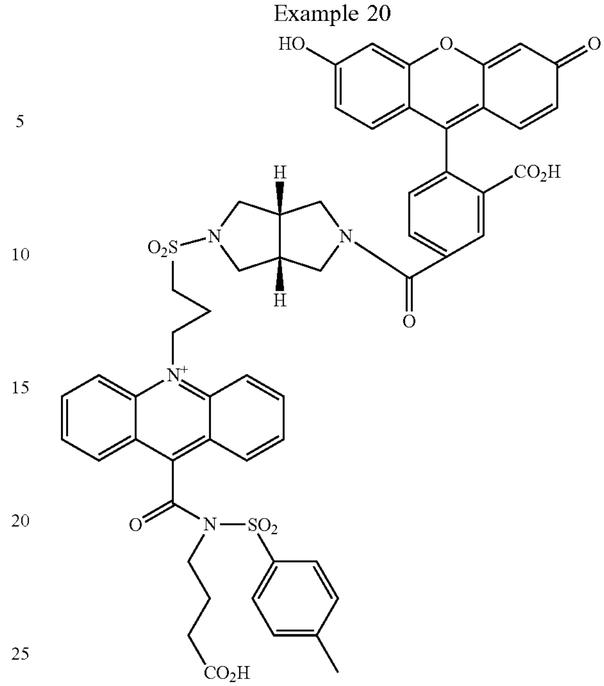

The titled compound was prepared using the same procedure outlined for the preparation of Example 12 utilizing 0.0045 g (0.005 mmol) of the product from Example 7, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0033 g of an orange yellow film (titled compound). MS (M+): calculated for $C_{55}H_{49}N_4O_{13}S_2$+: Exact Mass: 1037.2732; Molecular Weight: 1038.1260. UPLC/MS measured 1037.18.

Example 21

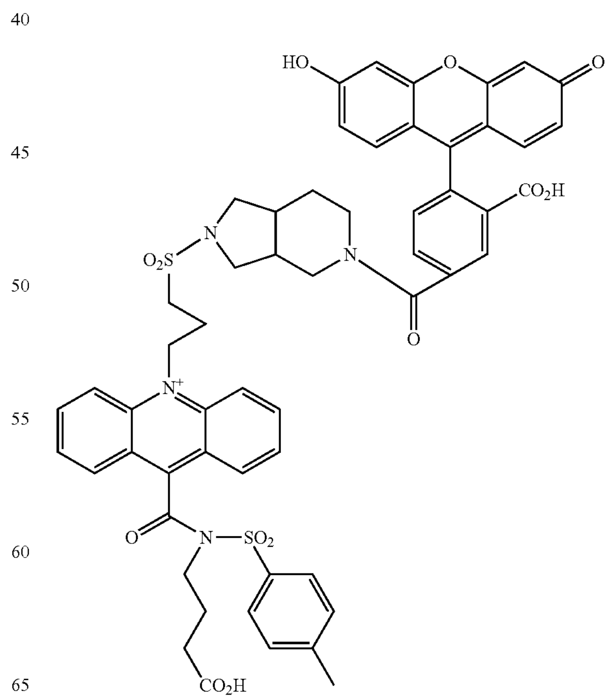

The titled compound was prepared using the same procedure outlined for the preparation of Example 12 utilizing 0.0038 g (0.0042 mmol) of the product from Example 8, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0023 g of an orange yellow film (titled compound). MS (M+): calculated for $C_{54}H_{47}N_4O_{13}S_2$+: Exact Mass: 1051.2889; Molecular Weight: 1052.1526. UPLC/MS measured 1051.30.

Example 22

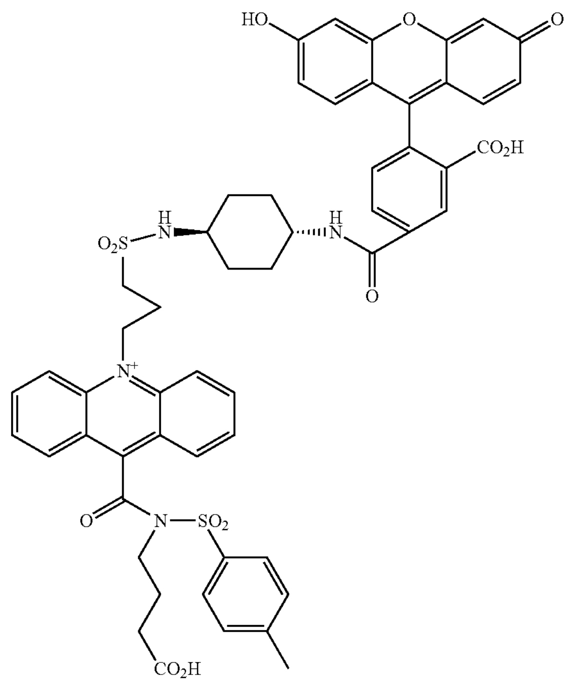 [SMILES: Cc1ccc(S(=O)(=O)N(CCCC(=O)O)C(=O)c2c3ccccc3[n+](CCCS(=O)(=O)N[C@H]3CC[C@H](NC(=O)c4ccc(-c5c6ccc(=O)cc-6oc6cc(O)ccc56)c(C(=O)O)c4)CC3)c3ccccc23)cc1]

The titled compound was prepared using the same procedure outlined for the preparation of Example 12 utilizing 0.005 g (0.0063 mmol) of the product from Example 9, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0042 g of a yellow film (titled compound). MS (M+): calculated for $C_{55}H_{51}N_4O_{13}S_2$+: Exact Mass: 1039.2889; Molecular Weight: 1040.1419. UPLC/MS measured 1039.29.

Example 23

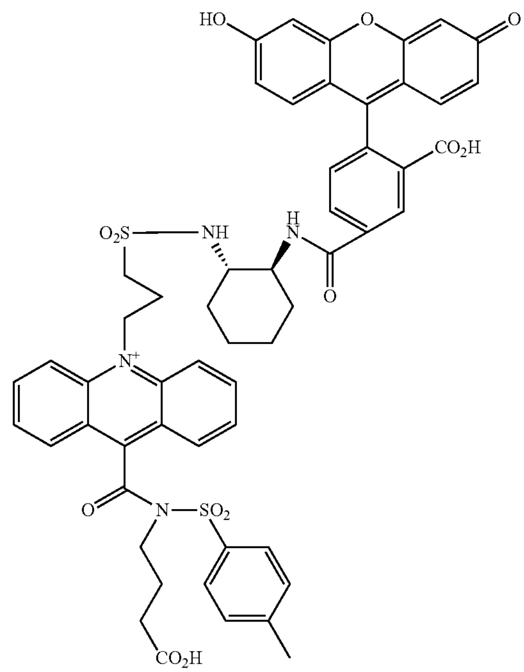 [SMILES: Cc1ccc(S(=O)(=O)N(CCCC(=O)O)C(=O)c2c3ccccc3[n+](CCCS(=O)(=O)N[C@H]3CCCC[C@@H]3NC(=O)c3ccc(-c4c5ccc(=O)cc-5oc5cc(O)ccc45)c(C(=O)O)c3)c3ccccc23)cc1]

The titled compound was prepared using the same procedure outlined for the preparation of Example 12 utilizing 0.0057 g (0.0072 mmol) of the product from Example 10, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0024 g of a yellow film (titled compound). MS (M+): calculated for $C_{55}H_{51}N_4O_{13}S_2$+: Exact Mass: 1039.2889; Molecular Weight: 1040.1419. UPLC/MS measured 1039.21.

Example 24

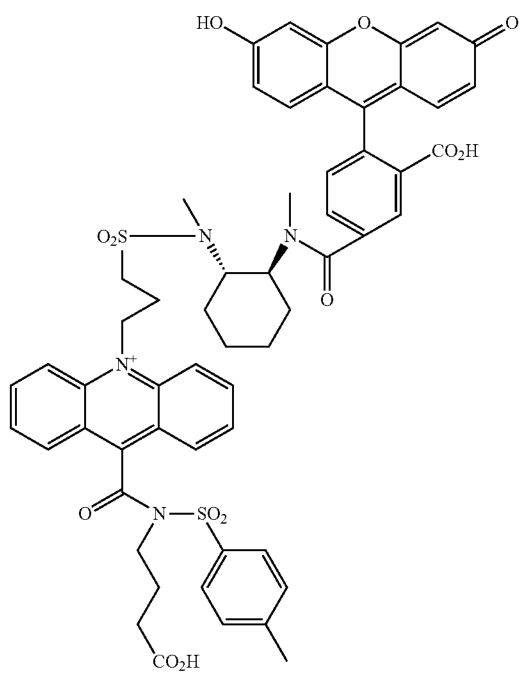 [SMILES: Cc1ccc(S(=O)(=O)N(CCCC(=O)O)C(=O)c2c3ccccc3[n+](CCCS(=O)(=O)N(C)[C@H]3CCCC[C@@H]3N(C)C(=O)c3ccc(-c4c5ccc(=O)cc-5oc5cc(O)ccc45)c(C(=O)O)c3)c3ccccc23)cc1]

The titled compound was prepared using the same procedure outlined for the preparation of Example 12 utilizing 0.003 g (0.0036 mmol) of the product from Example 11, DMF (0.2 mL), 0.008 g (0.017 mmol) of 5-carboxyfluorescein-PFP ester (from 5-carboxyfluorescein and pentafluorophenyl trifluoroacetate) and DIEA (0.01 mL, 0.06 mmol). Yield 0.0006 g of a yellow film (titled compound). MS (M+): calculated for $C_{57}H_{55}N_4O_{13}S_2$+: Exact Mass: 1067.32; Molecular Weight: 1068.20. UPLC/MS measured 1067.14.

Example 25

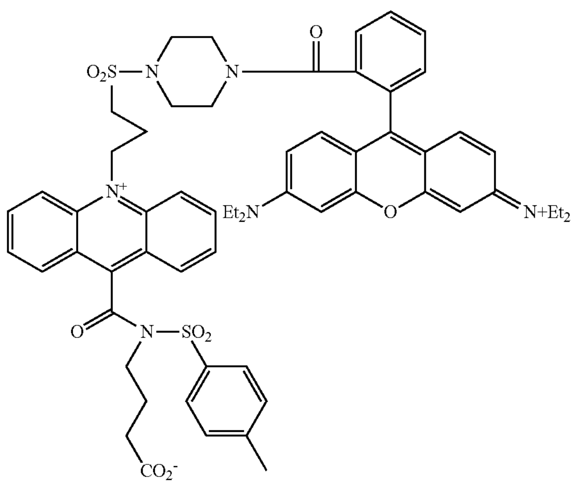

The titled compound was prepared using the same procedure outlined for the preparation of Example 12 utilizing 0.006 g (0.008 mmol) of the product from Example 2, DMF (0.2 mL), 0.008 g (0.013 mmol) of rhodamine B-PFP ester (prepared from rhodamine B and pentafluorophenyl trifluoroacetate) and DIEA (0.01 mL, 0.06 mmol). Yield 0.0031 g of a purple film (titled compound). MS (M+): calculated for $C_{60}H_{65}N_6O_9S_2$+: Exact Mass: 1077.42; Molecular Weight: 1078.33. UPLC/MS measured 1077.51.

Example 26

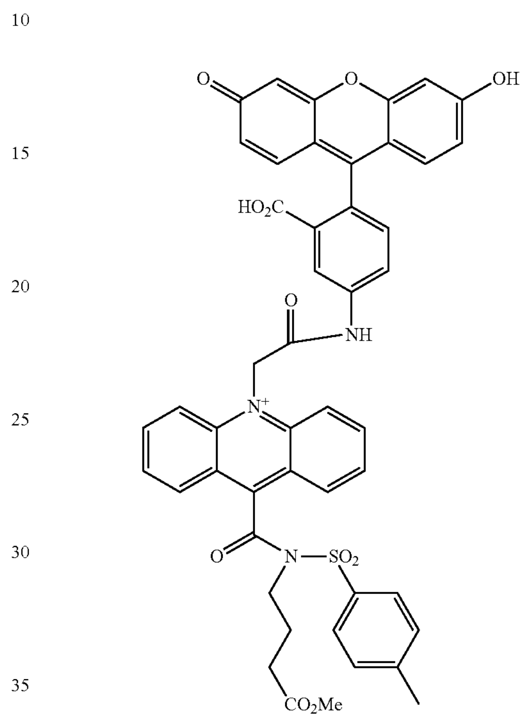

CP-acridine methyl ester (*J. Org. Chem.* 1998, 63, 5636-5639) (0.012 g, 0.025 mmol) and 5-(iodoacetamido) fluorescein (0.015 g, 0.029 mmol) were mixed in a 5 mL round bottom flask equipped with a nitrogen inlet. Without solvent, the flask was heated in an oil bath at 160-170° C. for 15 minutes. After this time, LCMS indicated a complex mixture with the starting materials both present as well as the titled compound as a component. The reaction was taken up in DMF/MeOH/water (~0.5 mL of each) and purified by reverse phase HPLC using a YMC ODS AQ 30×150 mm steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% Formic acid. The volatile components were removed in vacuo on a rotary evaporator at 30° C. and dried under high vacuum (1 mm Hg) over 24 hours. Yield 0.0007 g of a yellow film (titled compound). MS (M+): calculated for $C_{48}H_{38}N_3O_{11}S$+: Exact Mass: 864.2222; Molecular Weight: 864.8933. UPLC/MS measured 864.43.

Example 27

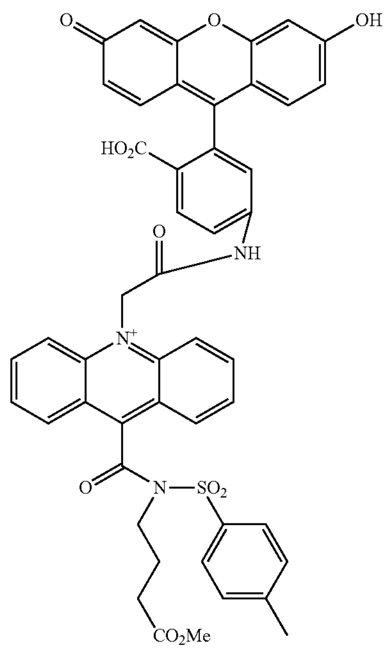 [SMILES: COC(=O)CCCN(C(=O)c1c2ccccc2[n+](CC(=O)Nc2ccc(C(=O)O)c(-c3c4ccc(=O)cc-4oc4cc(O)ccc34)c2)c2ccccc12)S(=O)(=O)c1ccc(C)cc1]

The titled compound was prepared using the same procedure outlined for the preparation of Example 26 utilizing 0.012 g (0.025 mmol) CP-acridinium methyl ester and 0.006 g (0.012 mmol) of 6-(iodoacetamido) fluorescein. Yield 0.0011 g of a yellow film (titled compound). MS (M+): calculated for $C_{48}H_{38}N_3O_{11}S+$: Exact Mass: 864.2222; Molecular Weight: 864.8933. UPLC/MS measured 864.51.

Example 28

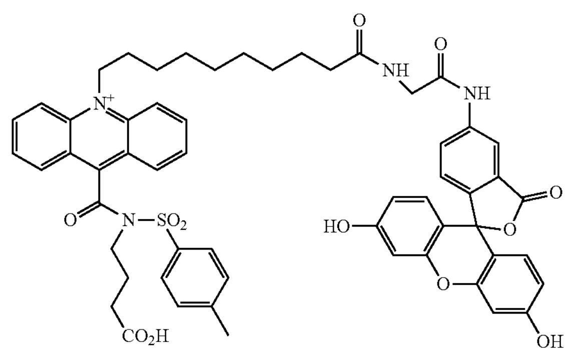 [SMILES: Cc1ccc(S(=O)(=O)N(CCCC(=O)O)C(=O)c2c3ccccc3[n+](CCCCCCCCCC(=O)NCC(=O)Nc3ccc4c(c3)C(=O)OC43c4ccc(O)cc4Oc4cc(O)ccc43)c3ccccc23)cc1]

The above compound was prepared from:

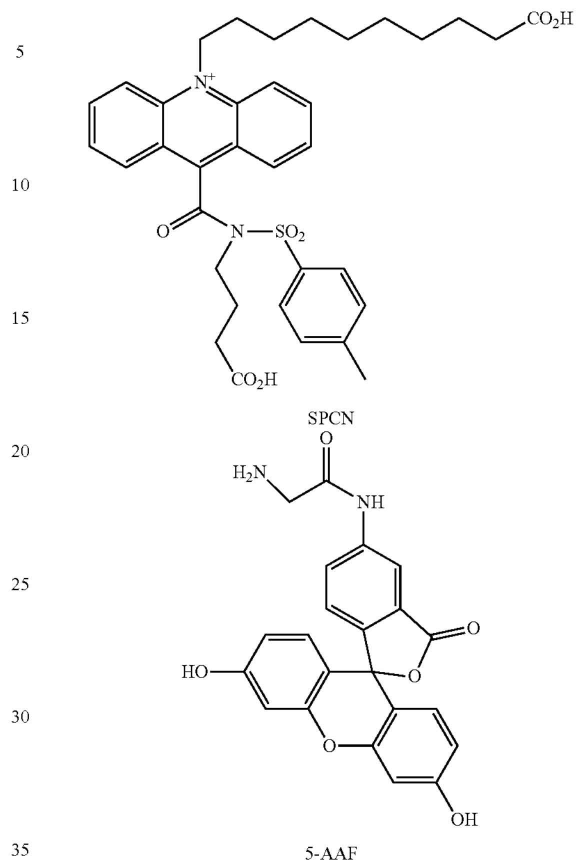

SPCN

5-AAF

SPCN (0.048 g), (*Organic Letters,* 2003, 5 (21), 3779), was dissolved in 0.5 mL DMF. 0.128 mL of DIEA was added followed by PyAOP (0.032 g). The reaction was stirred at ambient temperature for 5 minutes (preactivation). 0.032 g 5-acetamidoaminofluorescein (5-AAF) (Chemistry of Materials, 1992, 4 (4), 879-84) was dissolved in 1 mL of DMF and 0.064 mL of DIEA. The 5-AAF solution was added to the SPCN solution. After 18 hr, the reaction was treated with 3 mL of water. The solution was purified by HPLC by directly injecting the solution onto a YMC ODS-AQ column (40×100). Elution was at 45 mL/min with a gradient of 5 to 40% acetonitrile over 70 minutes (mobile phase ACN/$H_2O$/$H_2O$-0.5% TFA). The fractions containing the product were frozen and lyophilized. Yield 0.026 g (titled compound). MS consistent with titled compound.

Example 29

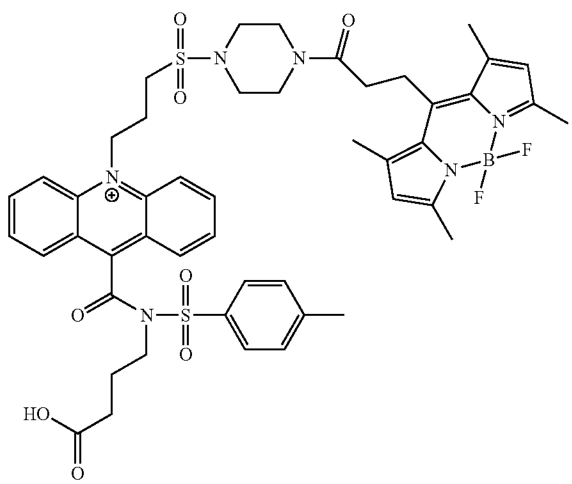

The titled compound was prepared using a similar procedure outlined for the preparation of example 12 utilizing 0.01 g of the product from example 2, DMF (0.5 mL), 0.005 g (0.012 mmol) of BODIPY™ 493/503 NHS Ester (ThermoFisher) and DIEA (0.01 mL, 0.06 mmol). Reaction was stirred overnight. Yield 0.0021 g of a red film (titled compound). MS (M+): calculated for $C_{48}H_{54}BF_2N_6O_8S_2$+; Exact Mass: 955.3500; Molecular Weight: 955.9203. UPLC/MS measured 955.38.

Example 30

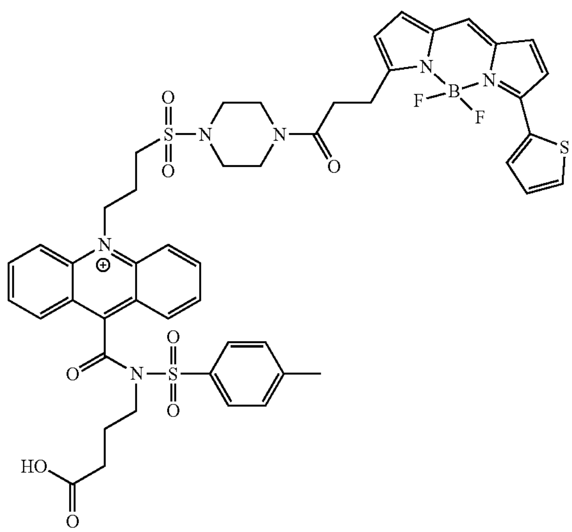

The titled compound was prepared using a similar procedure outlined for the preparation of example 12 utilizing 0.014 g (0.018 mmol) of the product from example 2, DMF (0.5 mL), 0.005 g (0.011 mmol) of BDP 558/568 NHS Ester (Lumiprobe) and DIEA (0.01 mL, 0.06 mmol). Reaction was stirred overnight. Yield 0.0033 g of a purple film (titled compound). MS (M+): calculated for $C_{48}H_{48}BF_2N_6O_8S_3$+; Exact Mass: 981.2751; Molecular Weight: 981.9323. UPLC/MS measured 981.33.

Example 31

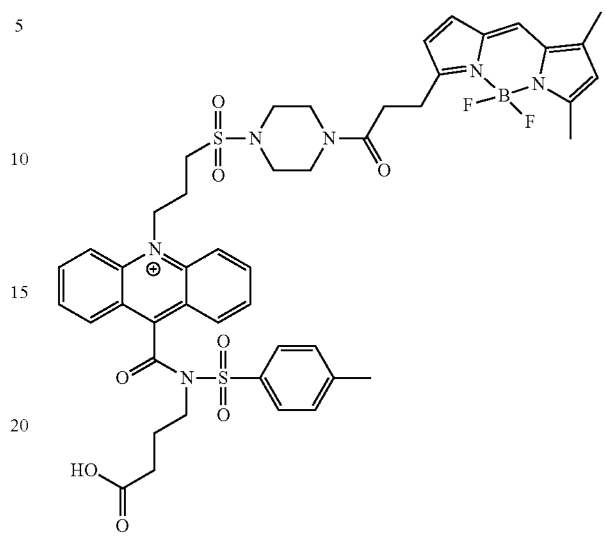

The titled compound was prepared using a similar procedure outlined for the preparation of example 12 utilizing 0.03 g (0.039 mmol) of the product from example 2, DMF (1 mL), 0.01 g (0.025 mmol) of BDP FL NHS Ester (Lumiprobe) and DIEA (0.02 mL, 0.12 mmol). Reaction was stirred overnight. Yield 0.0026 g of a red film (titled compound). MS (M+): calculated for $C_{46}H_{50}BF_2N_6O_8S_2$+; Exact Mass: 927.3187; Molecular Weight: 927.8663. UPLC/MS measured 927.52.

Example 32

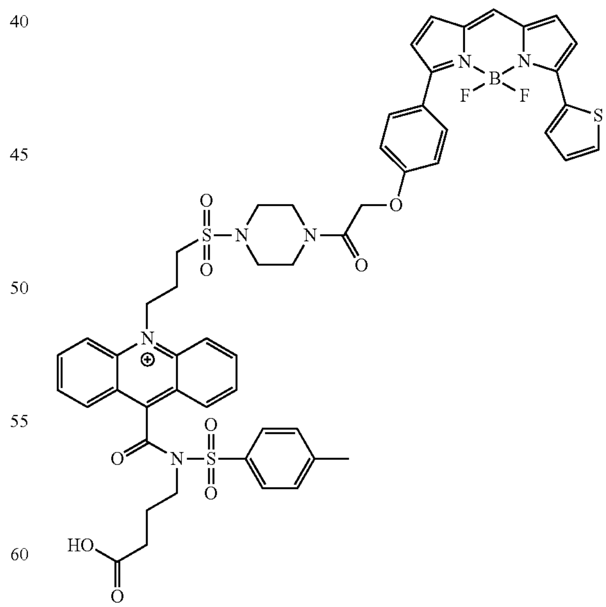

The titled compound was prepared using a similar procedure outlined for the preparation of example 12 utilizing 0.03 g (0.039 mmol) of the product from example 2, DMF (1 mL), 0.014 g (0.027 mmol) of BDP TR NHS Ester (Lumiprobe) and DIEA (0.02 mL, 0.12 mmol). Reaction was stirred overnight. Yield 0.019 g of a blue film (titled compound). MS (M+): calculated for $C_{53}H_{50}BF_2N_6O_9S_3$+; Exact Mass: 1059.2857; Molecular Weight: 1060.0023. UPLC/MS measured 1059.26.

Example 33

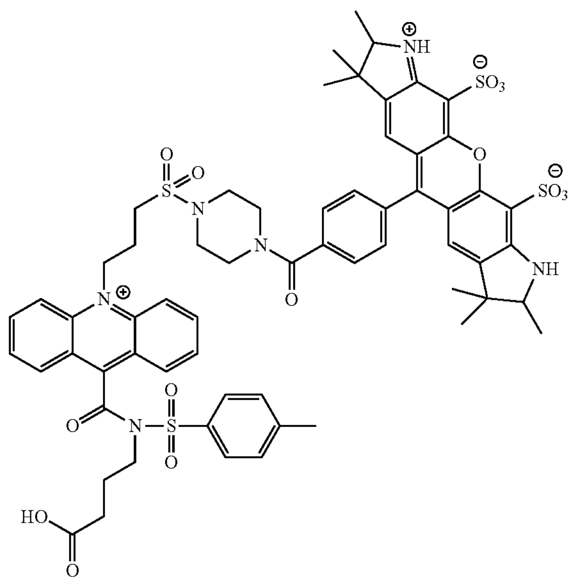

A 4 mL reaction vial equipped with a magnetic stir bar and nitrogen inlet was charged with 0.005 g (0.0069 mmol) of Alexa Fluor 532 carboxylic acid, 0.0029 g of HBTU (0.0076 mmol), DMSO (0.5 mL) and DIEA (0.05 mL, 0.3 mmol). The reaction was stirred at room temperature for 15 minutes before adding a DMSO solution (0.5 mL) containing the product from example 2 (0.015 g, 0.020 mmol). The reaction was stirred overnight. The crude reaction mixture was diluted with MeOH and water. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.0025 g of red film. MS (M+): calculated for $C_{62}H_{64}N_6O_{15}S_4$: Exact Mass: 1260.3312; Molecular Weight: 1261.4610. UPLC/MS measured 1262.42.

Example 34

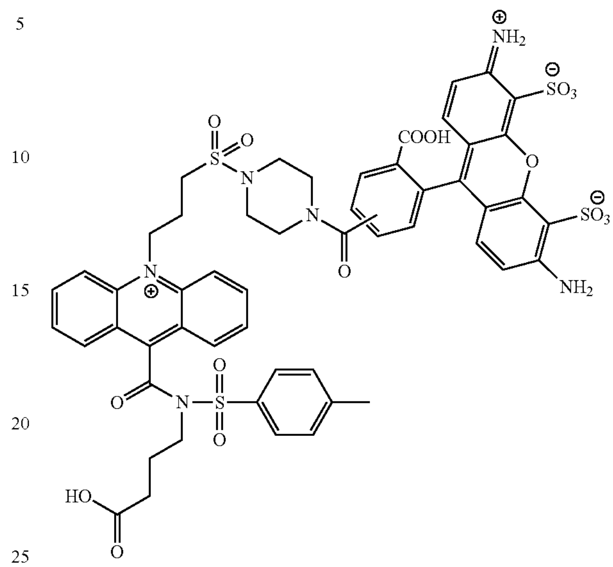

The titled compound was prepared using a similar procedure outlined for the preparation of Example 33 utilizing 0.012 g (0.016 mmol) of the product from Example 2, DMSO (1 mL), 0.005 g (0.0059 mmol) of Alexa Fluor 488 carboxylic acid, 0.0025 g (0.0066 mmol) of HBTU, and DIEA (0.05 mL, 0.3 mmol). Yield 0.002 g of a red film (titled compound 5 (6)-mixed isomers). MS (M+): calculated for $C_{53}H_{48}N_6O_{17}S_4$; Exact Mass: 1168.1959; Molecular Weight: 1169.2320. UPLC/MS measured 1169.28.

Example 35

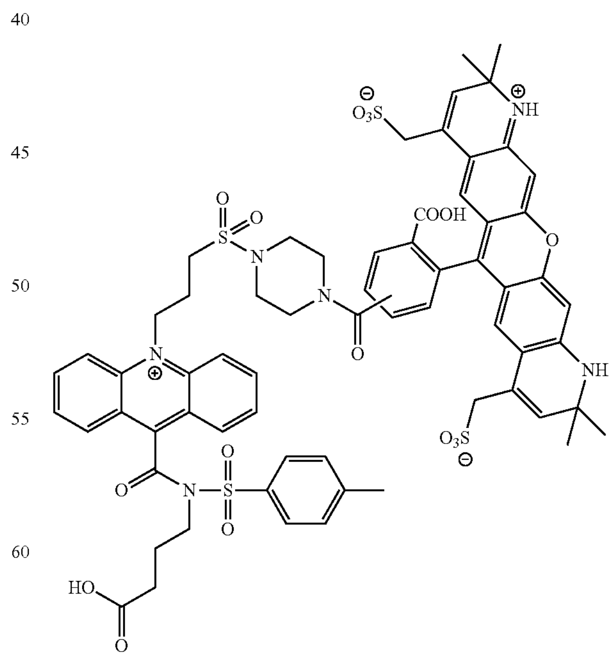

The titled compound was prepared using a similar procedure outlined for the preparation of Example 33 utilizing 0.0085 g (0.011 mmol) of the product from Example 2, DMSO (1 mL), 0.005 g (0.005 mmol) of Alexa Fluor 568 carboxylic acid, 0.0021 g (0.0055 mmol) of HBTU, and DIEA (0.05 mL, 0.3 mmol). Yield 0.0025 g of a purple film (titled compound 5 (6)-mixed isomers). MS (M+): calculated for $C_{65}H_{64}N_6O_{17}S_4$; Exact Mass: 1328.3211; Molecular Weight: 1329.4920. UPLC/MS measured 1330.24.

Example 36

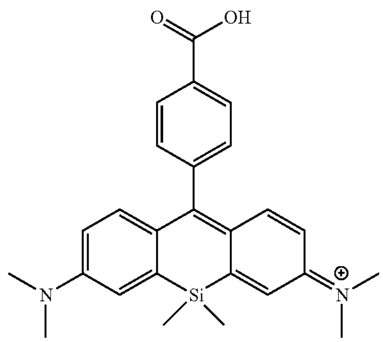

A 20 mL reaction vial equipped with a magnetic stir bar was charged with 0.075 g (0.17 mmol) of Methyl-4-carboxy-siliconrhodamine (*Angew. Chemi. Int. Ed.* 2018, 57, 2436-2440) and aqueous HCl (1 mL, 6 M). The contents were heated to 90° C. for 1 hour. The mixture was cooled to room temperature before diluting with 4:1 $CHCl_3$:methanol solvent mixture. The organic layer was washed with water and then brine before drying over sodium sulfate. The solvent was removed in vacuo. The crude solid was dissolved with MeOH and water. The entire solution was purified by reverse phase HPLC by elution on a YMC ODS AQ 50×250 mm I.D. steel column with a Waters Separations 2000 system monitored at 254 nm. Recorder chart speed 5 mm/min. A manual step gradient method (flow rate 70 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.054 g of blue film. MS (M+): calculated for $C_{26}H_{29}N_2O_2Si+$; Exact Mass: 429.1993; Molecular Weight: 429.6145. UPLC/MS measured 429.19.

Example 37

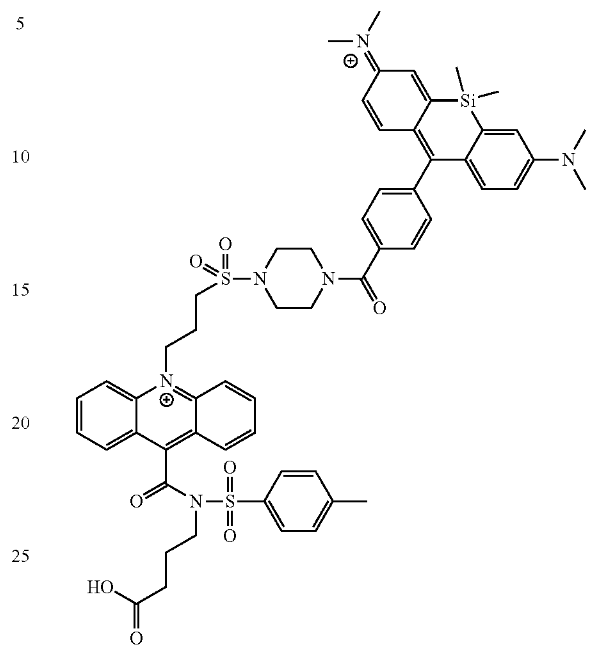

The titled compound was prepared using a similar procedure outlined for the preparation of Example 12 utilizing 0.025 g (0.033 mmol) of the product from Example 2, DMF (1 mL), 0.009 g (0.015 mmol) of 4-carboxy-SiR—PFP ester (example 37 and pentafluorophenyl trifluoroacetate) and DIEA (0.1 mL, 0.6 mmol). Yield 0.004 g of a blue film (titled compound). MS (M+): calculated for $C_{58}H_{64}N_6O_8S_2Si^{2+}$; Exact Mass: 1064.3985; Molecular Weight: 1065.3879. UPLC/MS measured 1064.44 (weak); M++ 532.46 (strong).

Example 38

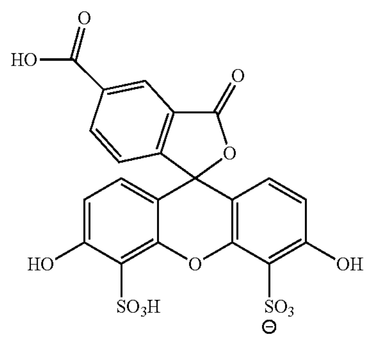

A 20 mL reaction vial equipped with a magnetic stir bar was charged with 0.315 g (0.84 mmol) of 5-carboxyfluorescein and fuming sulfuric acid (5 mL, 30% free $SO_3$ basis), and was heated to 90° C. for 1 hour. The reaction mixture was cooled to room temperature and then carefully added to a beaker containing ice before adding KCl (1 g) resulting in a yellow precipitate. The solid was filtered, washed with cold water and acetone, and dried under high vacuum for 18 hours. The solid was used in the next step without further purification. Yield 0.250 g of a yellow solid. MS (M−): calculated for $C_{21}H_{11}O_{13}S_2$—; Exact Mass: 534.9647; Molecular Weight: 535.4265. UPLC/MS measured 534.93.

Example 39

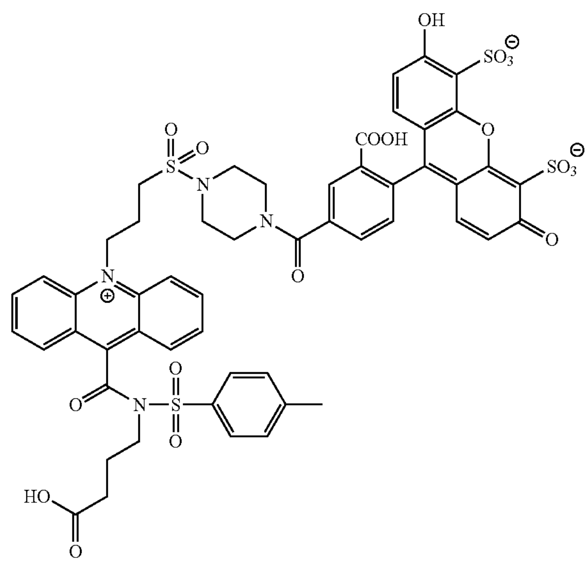

The titled compound was prepared using a similar procedure outlined for the preparation of Example 12 utilizing 0.009 g (0.012 mmol) of the product from Example 2, DMF (0.5 mL), 0.009 g (0.015 mmol) of 5-carboxy-4',5'-disulfo-fluorescein-PFP ester (Example 38 and pentafluorophenyl trifluoroacetate) and DIEA (0.05 mL, 0.3 mmol). Yield 0.007 g of a yellow film. MS (M−): calculated for $C_{53}H_{45}N_4O_{19}S_4$; Exact Mass: 1169.1566; Molecular Weight: 1170.1925. UPLC/MS measured 1169.99.

Example 40

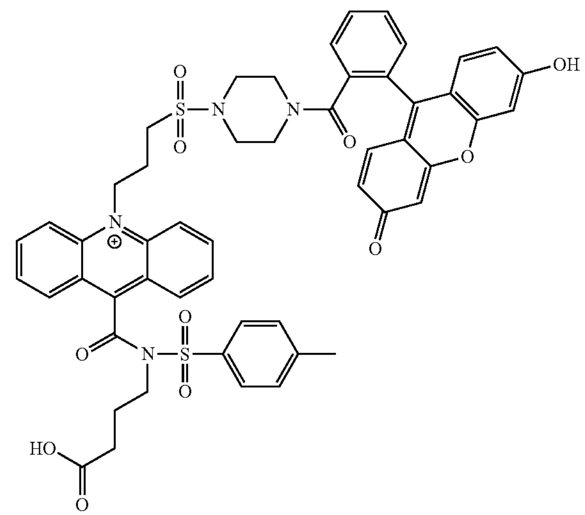 [SMILES: Cc1ccc(S(=O)(=O)N(CCCC(=O)O)C(=O)c2c3ccccc3[n+](CCCS(=O)(=O)N3CCN(C(=O)c4ccccc4-c4c5ccc(=O)cc-5oc5cc(O)ccc45)CC3)c3ccccc23)cc1]

A 4 mL reaction vial equipped with a magnetic stir bar and nitrogen inlet was charged with 0.013 g (0.04 mmol) of fluorescein, 0.014 g of HBTU (0.037 mmol), DMSO (1 mL) and DIEA (0.1 mL, 0.6 mmol). The reaction was stirred at 45° C. for 60 minutes. The solution was then cooled to room temperature before adding a DMSO solution (0.5 mL) containing the product from Example 2 (0.04 g, 0.052 mmol). The reaction was stirred overnight. The crude reaction mixture was diluted with MeOH and water. The entire solution was purified by reverse phase HPLC by elution on a YMC ODS AQ 50×250 mm I.D. steel column with a Waters Separations 2000 system monitored at 254 nm. Recorder chart speed 5 mm/min. A manual step gradient method (flow rate 70 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.002 g of red film. MS (M+): calculated for $C_{52}H_{47}N_4O_{11}S_2$+; Exact Mass: 967.2677; Molecular Weight: 968.0845. UPLC/MS measured 967.32 (weak); M++ 484.38 (strong).

Example 41

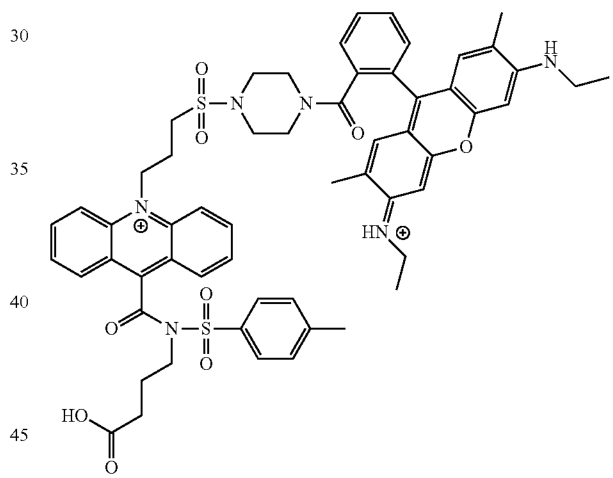

The titled compound was prepared using a similar procedure outlined for the preparation of Example 12 utilizing 0.015 g (0.020 mmol) of the product from Example 2, DMF (0.5 mL), 0.008 g (0.016 mmol) of rhodamine 19-NHS ester (Rhodamine 19 and TSTU) and DIEA (0.05 mL, 0.3 mmol). Yield: 0.002 g of red film. MS (M+): calculated for $C_{58}H_{62}N_6O_9S_2^{2+}$; Exact Mass: 1050.4009; Molecular Weight: 1051.2859. UPLC/MS measured 1049.31 (weak); M++ 525.46 (strong).

Example 42

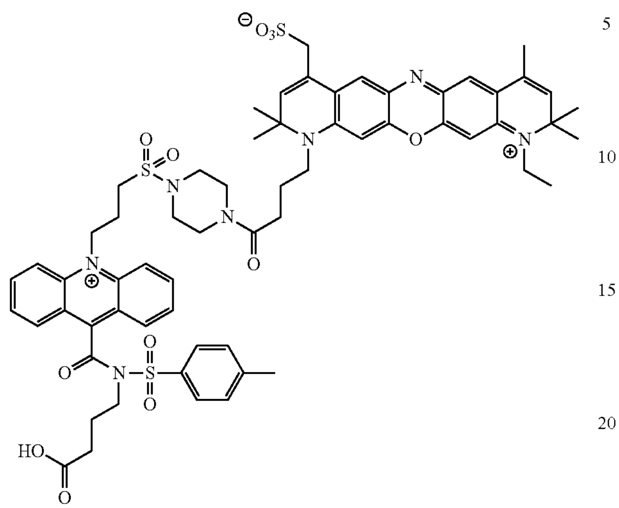

The titled compound was prepared using a similar procedure outlined for the preparation of Example 12 utilizing 0.0065 g (0.0085 mmol) of the product from Example 2, DMF (0.4 mL), 0.002 g (0.003 mmol) of Atto 700 NHS-ester, and DIEA (0.05 mL, 0.3 mmol). Yield: 0.003 g of green film. MS (M+): calculated for $C_{62}H_{70}N_7O_{12}S_3$+; Exact Mass: 1200.4239; Molecular Weight: 1201.4585. UPLC/MS measured 1200.56 (weak); M++ 600.92 (strong).

Example 43

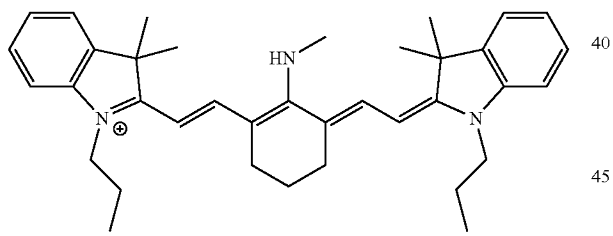

A 20 mL reaction vial equipped with a magnetic stir bar and nitrogen inlet was charged with 0.2 g (0.30 mmol) of IR 780 iodide, DMF (2 mL), and a solution of methylamine in THF (3 mL, 2 M). This was heated to 80° C. for 1 hour, during which time the color of the solution changed from green to blue. The reaction mixture was cooled to room temperature before triturating the product in diethyl ether. The product was used in the next step without further purification. Yield: 0.160 g of blue powder. MS (M+): calculated for Chemical Formula: $C_{37}H_{48}N_3$+; Exact Mass: 534.3843; Molecular Weight: 534.8115. UPLC/MS measured 534.37.

Example 44

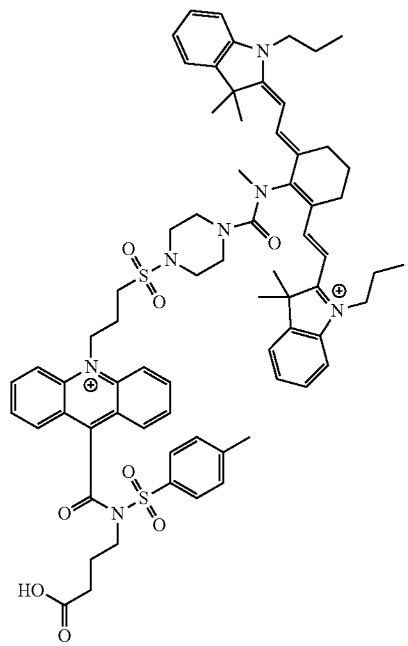 [SMILES: CCCN1/C(=C/C=C2\CCCC(/C=C/C3=[N+](CCC)c4ccccc4C3(C)C)=C2N(C)C(=O)N2CCN(S(=O)(=O)CCC[n+]3c4ccccc4c(C(=O)N(CCCC(=O)O)S(=O)(=O)c4ccc(C)cc4)c4ccccc43)CC2)C(C)(C)c2ccccc21]

In a 20 mL reaction vial equipped with a magnetic stir bar and nitrogen inlet was charged with 0.025 g (0.038 mmol) of the product from Example 43, DOM (10 mL), and 0.033 g (0.114 mmol) of triphosgene. The reaction mixture was cooled to 0° C. in an ice bath before adding 0.3 mL of DIEA. Stirring was continued for 1 hour before the solvent was removed in vacuo. The crude material was then charged with 0.040 g (0.052 mmol) of the product from Example 2, DMF (1 mL), and DIEA (0.1 mL, 0.6 mmol). The reaction mixture was stirred for 36 hours at room temperature. The crude reaction mixture was diluted with MeOH and water. The entire solution was purified by reverse phase HPLC by elution on a YMC ODS AQ 50×250 mm I.D. steel column with a Waters Separations 2000 system monitored at 254 nm. Recorder chart speed 5 mm/min. A manual step gradient method (flow rate 70 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield 0.004 g of green film. MS (M+): calculated for $C_{70}H_{83}N_7O_8S_2^{2+}$; Exact Mass: 1213.5734; Molecular Weight: 1214.5939. UPLC/MS measured 1212.50 (weak); M++ 607.05 (strong).

Example 45

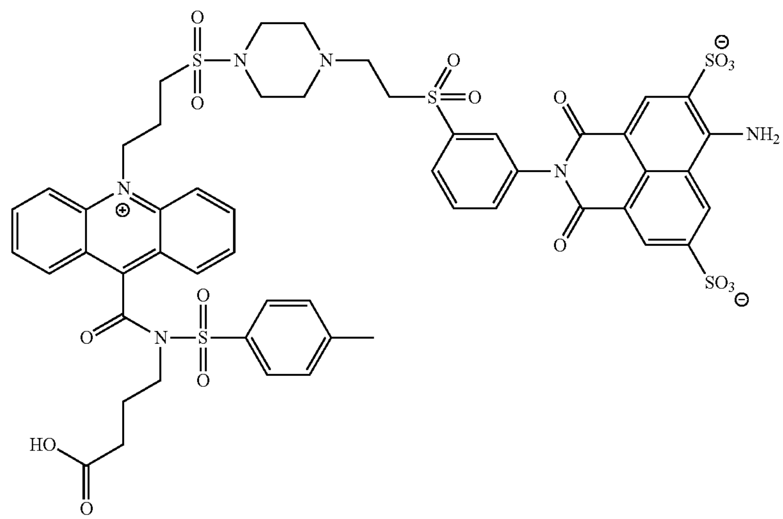

The titled compound was prepared using a similar procedure outlined for the preparation of Example 12 utilizing 0.0165 g (0.021 mmol) of the product from Example 2, DMF (1 mL), 0.008 g (0.015 mmol) of Lucifer Yellow VS dilithium salt, and DIEA (0.05 mL, 0.3 mmol). Yield: 0.009 g of yellow powder. MS (M−): calculated for $C_{52}H_{49}N_6O_{17}S_5$; Exact Mass: 1189.1763; Molecular Weight: 1190.2895. UPLC/MS measured 1189.42.

Example 46

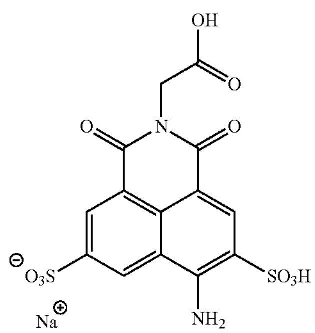

A 4 mL reaction vial equipped with a magnetic stir bar was charged with 0.110 g (0.30 mmol) of Lucifer Yellow anhydride, 0.123 g (1.65 mmol) of glycine, and an aqueous solution of sodium acetate (3 mL, 1M). The mixture was heated to 90° C. and stirred overnight. The crude reaction mixture was diluted with MeOH and water. The entire solution was purified by reverse phase HPLC by elution on a YMC ODS AQ 50×250 mm I.D. steel column with a Waters Separations 2000 system monitored at 254 nm. Recorder chart speed 5 mm/min. A manual step gradient method (flow rate 70 mL/min) was used with a mobile phase of ACN/$H_2O$/$H_2O$-0.5% TFA. Fractions containing the product were combined and the volatile components were removed in vacuo on a rotary evaporator at 30° C. followed by high vacuum for 18 hours at room temperature. Yield: 0.120 g of yellow powder. MS (M−): calculated for $C_{14}H_9N_2O_{10}S_2$; Exact Mass: 428.9704; Molecular Weight: 429.3505. UPLC/MS measured 429.05.

Example 47

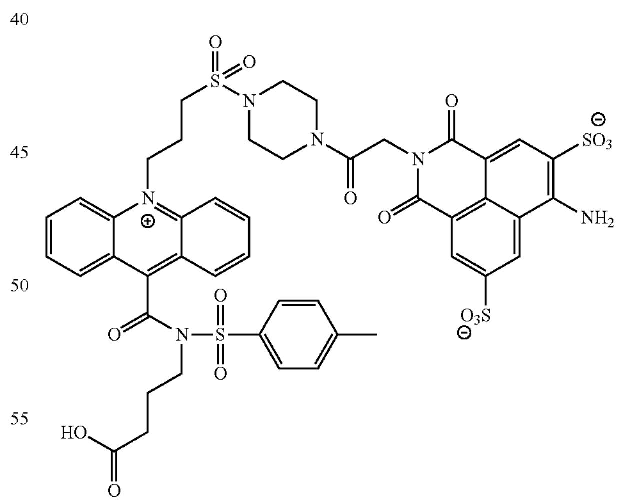

The titled compound was prepared using a similar procedure outlined for the preparation of Example 12 utilizing 0.085 g (0.11 mmol) of the product from Example 2, DMF (1 mL), 0.040 g (0.076 mmol) of the product from Example 46-NHS ester (example 46 and TSTU) and DIEA (0.17 mL, 1 mmol). Yield: 0.018 g of yellow powder. MS (M−): calculated for $C_{46}H_{43}N_6O_{16}S_4$—, Exact Mass: 1063.1624, Molecular Weight: 1064.1165, UPLC/MS measured 1063.24.

Example 48

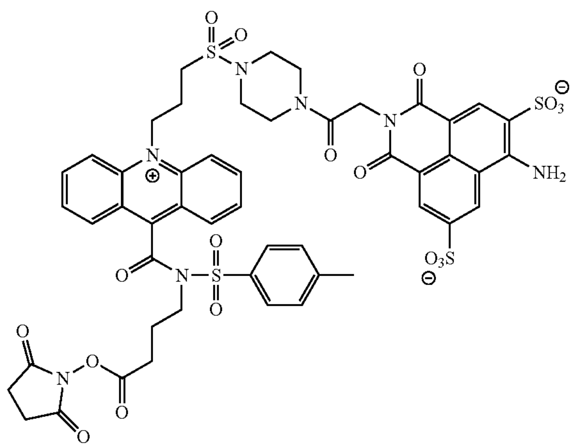

A 4 mL reaction vial equipped with a magnetic stir bar and nitrogen inlet was charged with 0.013 g (0.012 mmol) of the product from Example 47, 0.0055 mg (0.018 mmol) of TSTU, DMSO (0.5 mL), and DIEA (0.05 mL, 0.3 mmol). Mix was stirred for 1 hour at room temperature before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of $ACN/H_2O/H_2O$-0.05% formic acid. Fractions containing the product were combined and the volatile components were removed in vacuo on a rotary evaporator at 30° C. followed by high vacuum for 18 hours at room temperature. Yield: 0.008 mg of yellow film. MS (−): calculated for $C_{50}H_{46}N_7O_{18}S_4$—; Exact Mass: 1160.1788; Molecular Weight: 1161.1895. UPLC/MS measured 1160.28.

Example 49

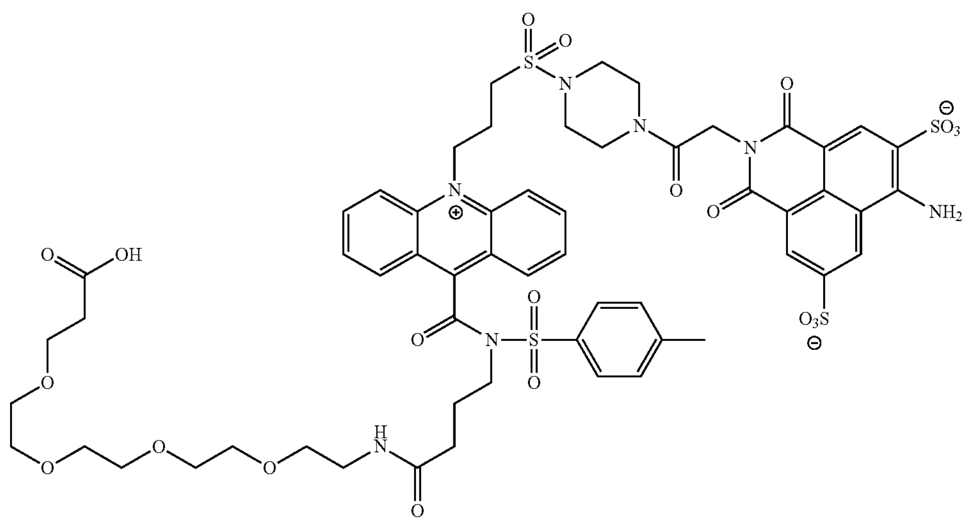

A 4 mL reaction vial equipped with a magnetic stir bar and nitrogen inlet was charged with 0.006 g (0.0052 mmol) of the product from Example 48, 0.020 g (0.062 mmol) of Amino-dPEG®$_4$-t-butyl ester, DMF (0.5 mL), and DIEA (0.1 mL, 0.6 mmol). The mixture was stirred for 1 hour before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of $ACN/H_2O/H_2O$-0.5% formic acid. Fractions containing the product were combined and the volatile components were removed in vacuo on a rotary evaporator at 30° C. followed by high vacuum for 18 hours at room temperature. The purified material was transferred to a 4 mL reaction vial equipped with a stir bar and was dissolved in 1 mL of DCM and 1 mL of TFA. The mixture stirred for 1 hour before removing the solvents in vacuo on a rotary evaporator at 30° C. followed by high vacuum for 18 hours at room temperature. No further purification was necessary. Yield: 0.0088 g of yellow film. MS (−): calculated for $C_{57}H_{64}N_7O_{21}S_4$—; Exact Mass: 1310.3044; Molecular Weight: 1311.4075. UPLC/MS measured 1310.82.

Example 50

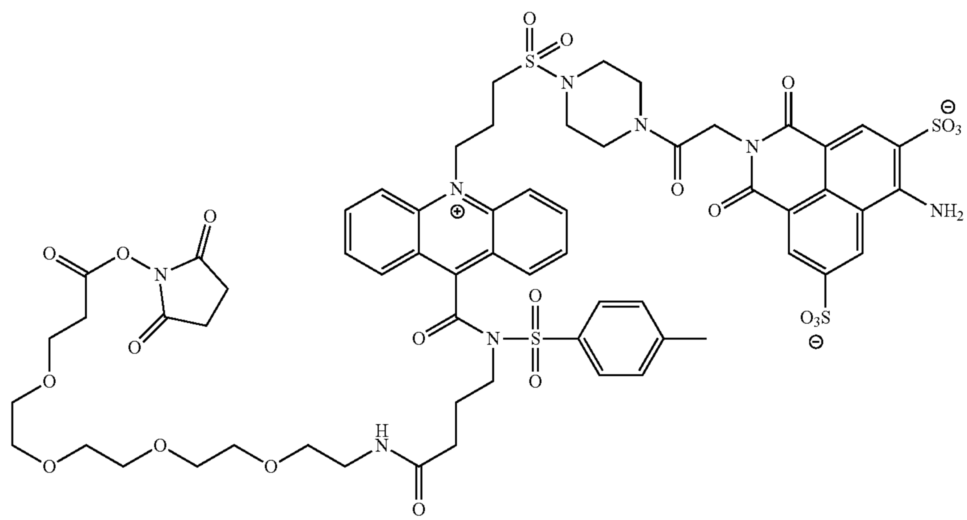

The titled compound was prepared using a similar procedure outlined for the preparation of Example 48 utilizing 0.0088 g (0.0067 mmol) of the product from Example 49, 0.003 g (0.010 mmol) of TSTU, DMF (0.5 mL), and DIEA (0.05 mL, 0.3 mmol). After purification and evaporation, 10% of the material had hydrolyzed back to the carboxylic acid form. Yield: 0.006 g. MS (−): calculated for $C_{61}H_{67}N_8O_{23}S_4$—; Exact Mass: 1407.3207; Molecular Weight: 1408.4805. UPLC/MS measured 1408.50.

Example 51

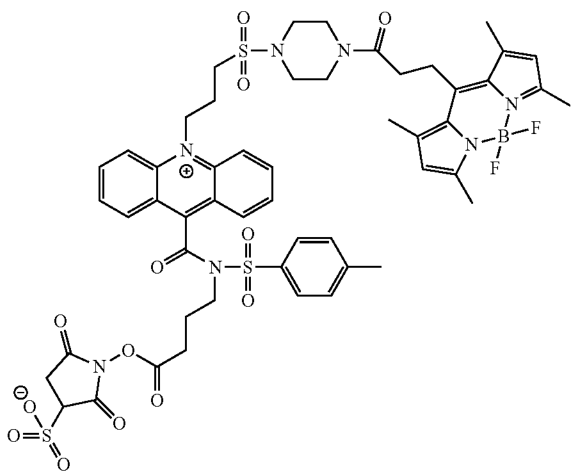

A 4 mL reaction vial equipped with a magnetic stir bar and nitrogen inlet was charged with 0.007 g (0.0072 mmol) of the product from Example 29, 0.0026 g (0.017 mmol) of EDC, 0.0036 g (0.017 mmol) of N-hydroxysulfosuccinimide sodium salt, DMF (0.5 mL), and DIEA (0.01 mL, 0.06 mmol). Reaction was stirred overnight before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.05% formic acid. Fractions containing the product were combined and the volatile components were removed in vacuo on a rotary evaporator at 30° C. followed by high vacuum for 18 hours at room temperature. Yield: 0.0025 g. MS (+): calculated for $C_{52}H_{56}BF_2N_7O_{13}S_3$; Exact Mass: 1131.3159; Molecular Weight: 1132.0428. UPLC/MS measured (M-F)+ 1112.20.

Example 52

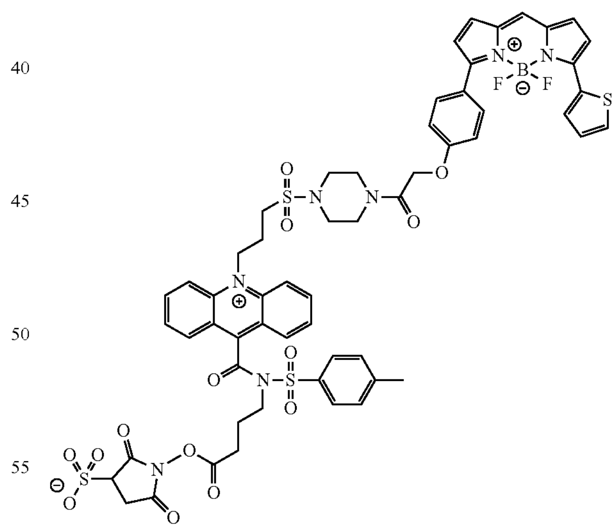

The titled compound was prepared using a similar procedure outlined for the preparation of Example 51 utilizing 0.009 g (0.0085 mmol) of the product from Example 32, 0.0026 g (0.017 mmol) of EDC, 0.0036 g (0.017 mmol) of N-hydroxysulfosuccinimide sodium salt, DMF (0.5 mL), and DIEA (0.01 mL, 0.06 mmol). Yield: 0.0013 g. MS (+): calculated for $C_{57}H_{52}BF_2N_7O_{14}S_4$; Exact Mass: 1235.2516; Molecular Weight: 1236.1248. UPLC/MS measured (M-F)+ 1216.40.

Example 53

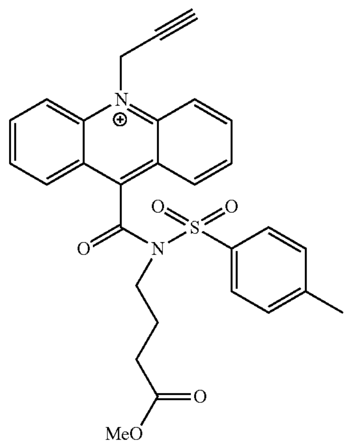 [SMILES: C#CC[n+]1c2ccccc2c(C(=O)N(CCCC(=O)OC)S(=O)(=O)c2ccc(C)cc2)c2ccccc21]

A 100 mL RB flask equipped with a stir bar and nitrogen inlet was charged with propargyl triflate (*J. Org Chem.*, 1977, 42, 3109-3113) (20.98 mmol) and $CH_2Cl_2$ (25 mL). To this solution was added 2,6-di-tert-butylpryridine (6.96 mL, 31.45 mmol) followed by the acridine (*J. Org Chem.*, 1998, 63, 5636-5639) (1.00 g, 2.10 mmol) and stirred for 18 h. The mixture was concentrated in vacuo. The residue was purified by reverse phase HPLC using a gradient method of 10% to 90% Acetonitrile/$H_2O$ with 0.5% TFA. The desired fractions were collected, pooled, frozen and lyophilized to afford 1.213 g of the title compound as a yellow solid (quant.). Yield: 1.213 g of yellow solid. MS (+): calculated for $C_{29}H_{27}N_2O_5S^+$; Exact Mass: 515.6; Molecular Weight: 515.6. UPLC/MS measured (M)+ 514.85.

Example 54

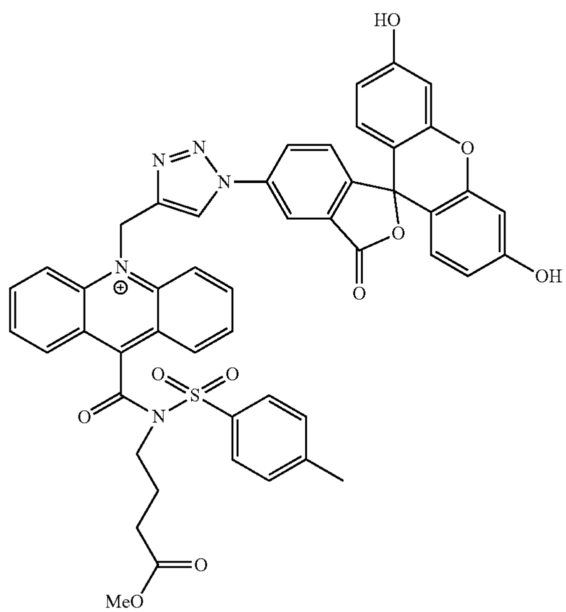 [SMILES: COC(=O)CCCN(C(=O)c1c2ccccc2[n+](Cc2cn(-c3ccc4c(c3)C(=O)OC43c4ccc(O)cc4Oc4cc(O)ccc43)nn2)c2ccccc12)S(=O)(=O)c1ccc(C)cc1]

A 50 mL Rb flask equipped with a stir bar and nitrogen inlet was charged with the product of Example 53 (0.014 g, 0.027 mmol), 5-azidofluorescein (*J. Am. Chem. Soc.* 2012, 134, 17428-17431) (0.010 g, 0.027 mmol) and a solution of DMF:$H_2O$ (2 mL, 1:1). To this mixture was added a solution of copper (II) sulfate (0.001 g, 0.001 mmol) in $H_2O$ (100 μL) followed by a solution of sodium ascorbate (0.001 g, 0.005 mmol) in $H_2O$ (100 μL) and stirred for 18 h. The mixture was purified by reverse phase HPLC purified using a gradient method of 10% to 90% Acetonitrile/$H_2O$ with 0.5% TFA. The desired fractions were collected, frozen and lyophilized to afford 14 mg of the title compound (58%). Yield: 0.014 g. MS (+): calculated for $C_{49}H_{39}N_5O_{11}S^+$; Exact Mass: 888.23; Molecular Weight: 888.92. UPLC/MS measured (M)+888.46.

Example 55

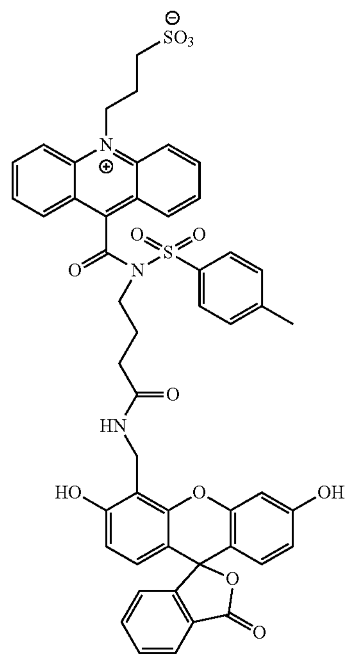

A 25 mL RB flask equipped with a stir bar and nitrogen inlet was charged with CPSP (0.020 g, 0.034 mmol), HBTU (0.014 g, 0.037 mmol), HOBt (0.005 g, 0,037 mmol) and DMF (2 mL). To this mixture was added DIEA (0.030 mL, 0.171 mmol) and stirred for 30 min. To this mixture was added 4'-aminomethylfluorescein (U.S. Pat. No. 4,510,251, 1985) (0.034 g, 0.094 mmol) and stirred for 18 h. The mixture was concentrated in vacuo. The residue was purified by reverse phase HPLC using a gradient method of 10% to 90% Acetonitrile/$H_2O$ with 0.5% TFA. The desired fractions were collected, frozen and lyophilized to afford 0.010 g of the title compound as a yellow-orange solid (32%). Yield: 0.010 g of a yellow-orange solid. MS (+): calculated for $C_{49}H_{41}N_3O_{12}S_2^+$; Exact Mass: 927.21; Molecular Weight: 928.00. UPLC/MS measured (M)+ 928.50.

Example 56

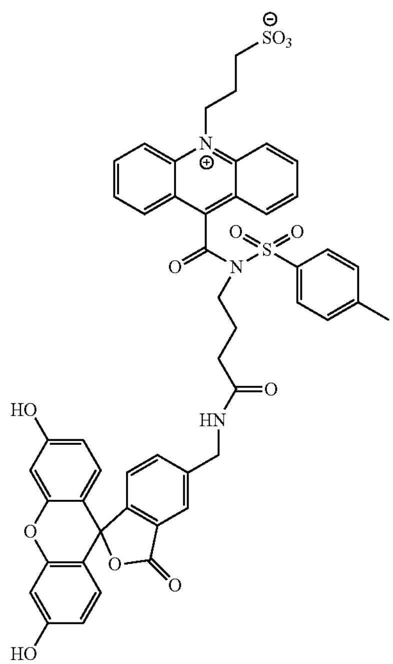

A 25 mL RB flask equipped with a stir bar and nitrogen inlet was charged with CPSP (0.050 g, 0.086 mmol), HBTU (0.036 g, 0.094 mmol), and HOBt (0.013 g, 0.094 mmol) and DMF (2 mL). To this mixture was added DIEA (0.074 mL, 0.428 mmol) and the reaction was stirred for 30 min. To this mixture was added 5-aminomethylfluorescein (*Bioconjugate Chem.* 1992, 3, 430-431) (0.034 g, 0.094 mmol) and stirred for 18 h. The mixture was concentrated in vacuo. The residue was purified by reverse phase HPLC using a gradient method of 10% to 90% Acetonitrile/$H_2O$ with 0.5% TFA. The desired fractions were collected and lyophilized to afford 0.027 g of the title compound as a yellow-orange solid (34%). Yield: 0.027 g of a yellow-orange solid. MS (+): calculated for $C_{49}H_{41}N_3O_{12}S_2^+$; Exact Mass: 927.21; Molecular Weight: 928.00. UPLC/MS measured (M+H)+ 929.45.

Example 57

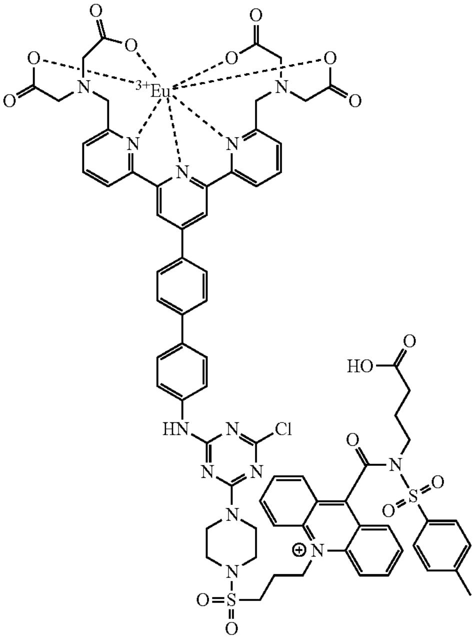

A 4 mL reaction vial equipped with a magnetic stir bar and nitrogen inlet was charged with 0.007 g (0.0072 mmol) of the product from Example 2, 0.003 g (0.003 mmol) of DTBTA-$Eu^{3+}$ (*Inorg. Chem.,* 2006, 45, 4088-4096), DMF (0.5 mL), and DIEA (0.01 mL, 0.06 mmol). Reaction was stirred overnight before being diluted in a small amount of ACN/$H_2O$. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.05 formic acid. Fractions containing the product were combined and the volatile components were removed in vacuo on a rotary evaporator at 30° C. followed by high vacuum for 18 hours at room temperature. Yield 0.002 g of a light-yellow powder. MS (M+): calculated for $C_{72}H_{65}ClEuN_{13}O_{15}S_2^{4+}$; Exact Mass: 1603.3043; Molecular Weight: 1603.9198. UPLC/MS measured 1604.65.

Example 58

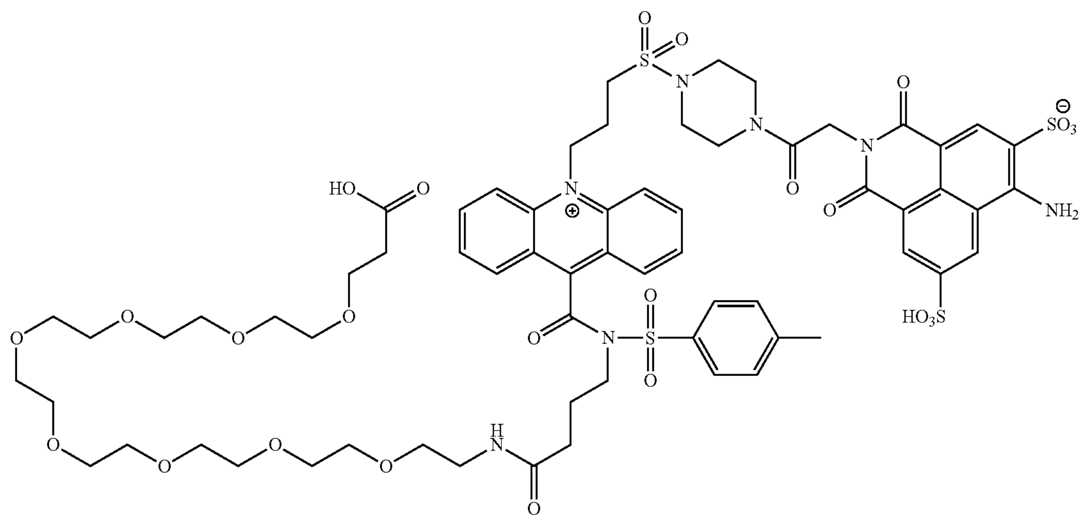

The titled compound was prepared using a similar procedure outlined for the preparation of Example 49 utilizing 0.011 g (0.0095 mmol) of the product from Example 48, 0.045 g (0.090 mmol) of Amino-dPEG®8-t-butyl ester, DMF (0.5 mL), and DIEA (0.1 mL, 0.6 mmol). Yield: 0.006 g of yellow film. MS (−): calculated for $C_{65}H_{81}N_7O_{25}S_4$—; Exact Mass: 1487.4165; Molecular Weight: 1488.6270. UPLC/MS measured 1487.71.

Example 59

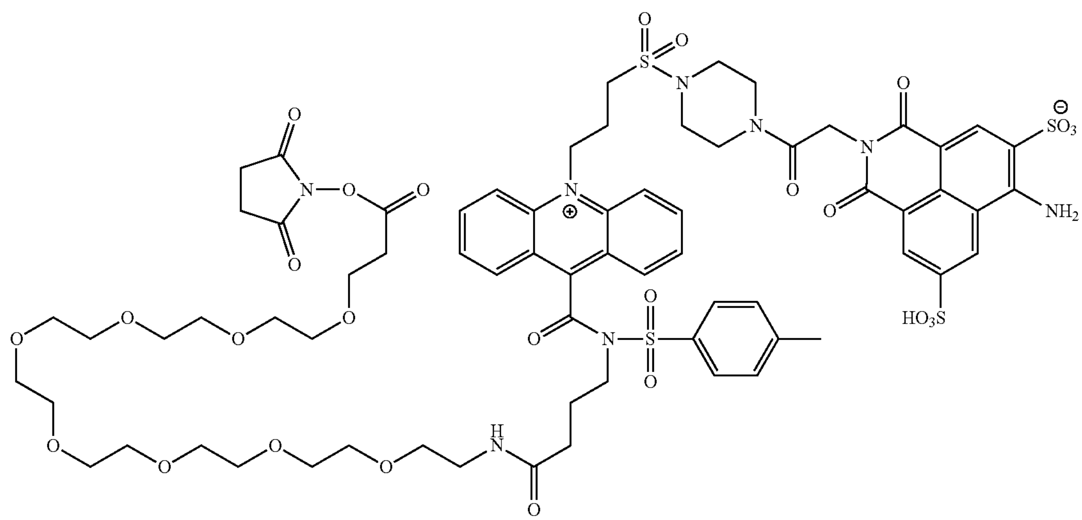

The titled compound was prepared using a similar procedure outlined for the preparation of Example 48 utilizing 0.006 g (0.0067 mmol) of the product from Example 58, 0.002 g (0.0067 mmol) of TSTU, DMF (0.5 mL), and DIEA (0.03 mL, 0.17 mmol). Yield: 0.004 g MS (−): calculated for $C_{69}H_{84}N_8O_{27}S_4$—; Exact Mass: 1584.4329; Molecular Weight: 1585.7000. UPLC/MS measured 1584.75.

Example 60

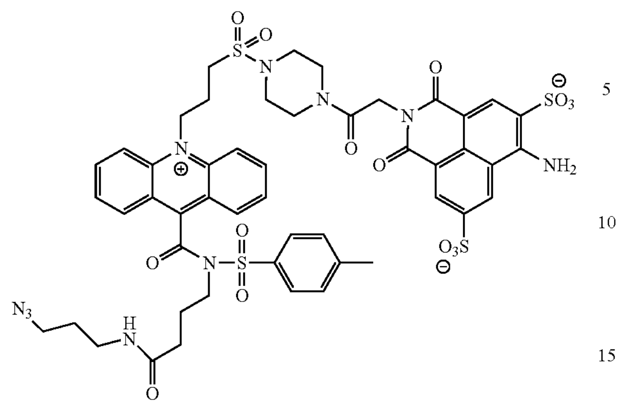

A 4 mL reaction vial equipped with a magnetic stir bar and nitrogen inlet was charged with 0.006 g (0.0052 mmol) of the product from Example 48, 0.025 g (0.25 mmol) of 3-azido-1-propanamine, DMF (0.5 mL), and DIEA (0.1 mL, 0.6 mmol). The mixture was stirred for 1 hour before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% formic acid. Fractions containing the product were combined and the volatile components were removed in vacuo on a rotary evaporator at 30° C. followed by high vacuum for 18 hours at room temperature. Yield: 0.003 g of yellow film. MS (−): calculated for $C_{49}H_{50}N_{10}O_{15}S_4$—; Exact Mass: 1145.2267; Molecular Weight: 1146.2265. UPLC/MS measured 1145.63.

Example 61

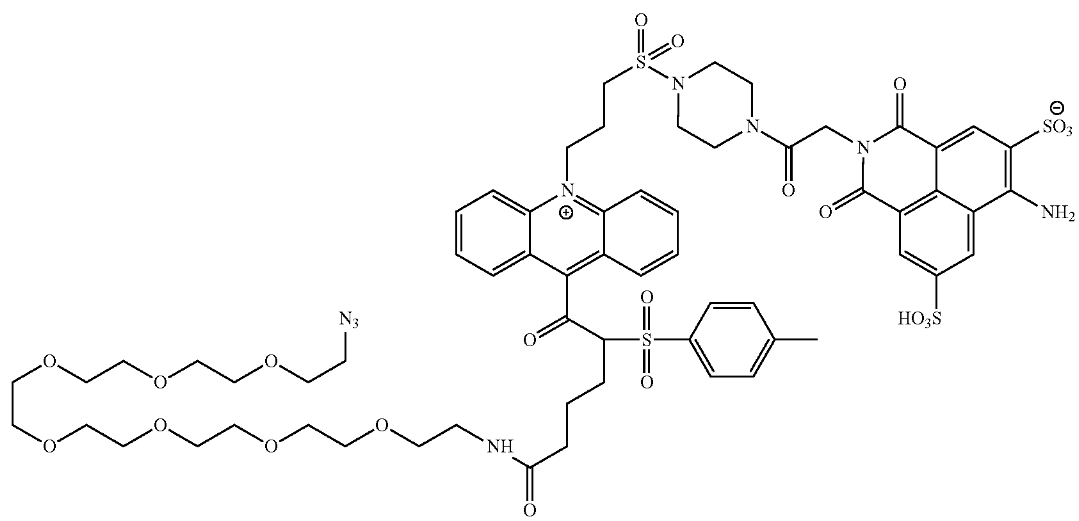

The titled compound was prepared using a similar procedure outlined for the preparation of Example 60 utilizing 0.006 g (0.0052 mmol) of the product from Example 48, 0.030 g (0.076 mmol) of azido-dPEG®7-amine, DMF (0.5 mL), and DIEA (0.1 mL, 0.6 mmol). Yield: 0.004 g of yellow film. MS (−): calculated for $C_{62}H_{76}N_{10}O_{22}S_4$; Exact Mass: 1440.4018; Molecular Weight: 1441.5780. UPLC/MS measured 1440.82.

Example 62

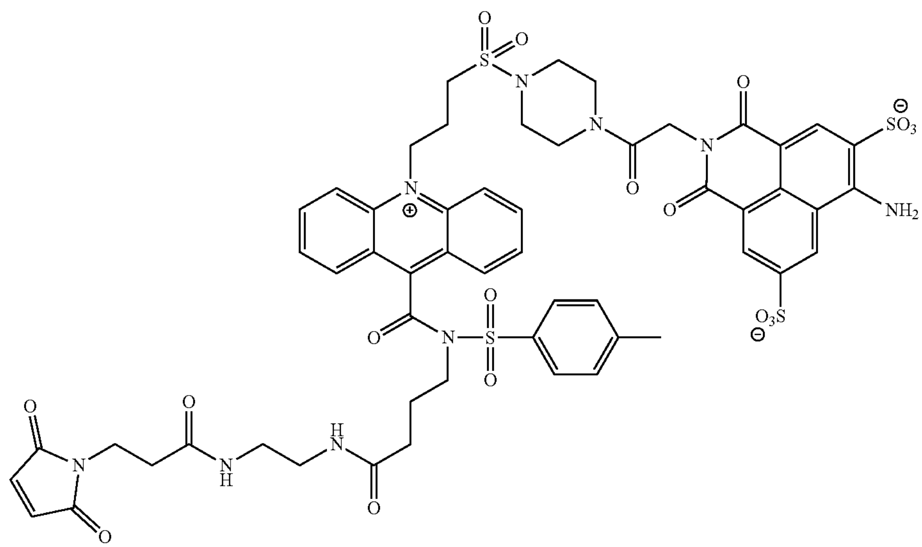

The titled compound was prepared using a similar procedure outlined for the preparation of Example 60 utilizing 0.0075 g (0.0065 mmol) of the product from Example 48, 0.020 g (0.076 mmol) of MPS-EDA (Quanta Biodesign), DMF (0.5 mL), and DIEA (0.1 mL, 0.6 mmol). Yield: 0.002 g of yellow film. MS (−): calculated for $C_{55}H_{54}N_9O_{18}S_4$; Exact Mass: 1256.2475; Molecular Weight: 1257.3225. UPLC/MS measured 1256.53

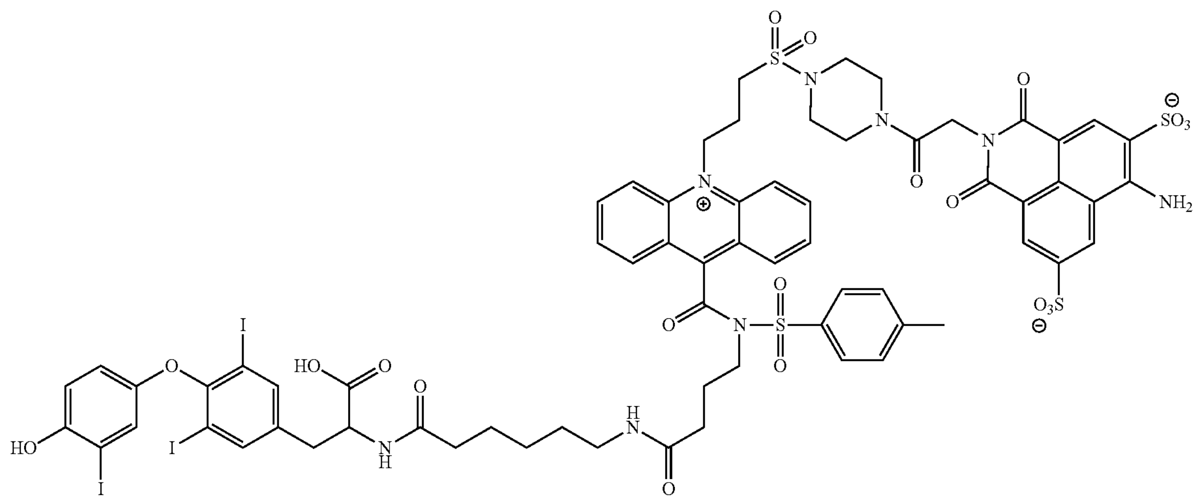

The titled compound was prepared using a similar procedure outlined for the preparation of Example 60 utilizing 0.006 g (0.0052 mmol) of the product from Example 48, 0.005 g (0.0067 mmol) of 2-(6-aminohexanamido)-thyroxine (*Bioconjugate Chem.* 1997, 8, 133-145), DMF (0.5 mL), and DIEA (0.01 mL, 0.06 mmol). Yield: 0.005 g of yellow film. MS (−): calculated for $C_{67}H_{65}I_3N_8O_{20}S_4^-$; Exact Mass: 1810.0332; Molecular Weight: 1811.2464. UPLC/MS measured 1810.59 (weak); $M^{2-}$ 904.99 (strong).

Example 64

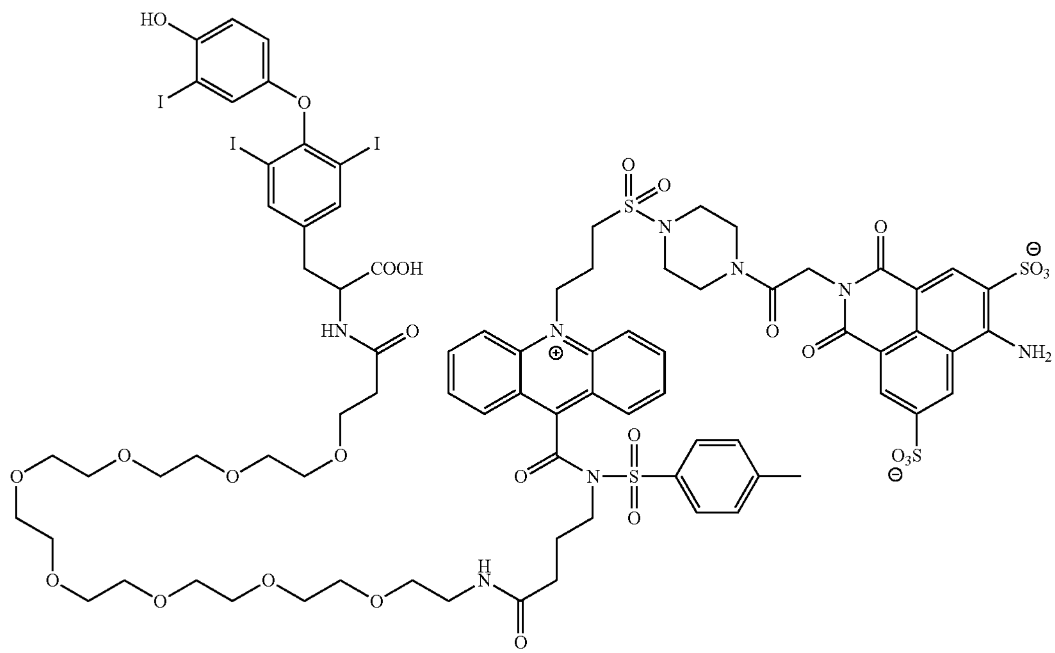

A 4 mL reaction vial equipped with a magnetic stir bar and nitrogen inlet was charged with 0.004 g (0.0025 mmol) of the product from Example 59, 0.0082 g (0.013 mmol) of thyroxine, DMF (0.5 mL), and DIEA (0.01 mL, 0.06 mmol). The mixture was stirred for 1 hour before being diluted in a small amount of ACN. The entire solution was purified by reverse phase HPLC by elution on a YMC ODS AQ 30×150 mm I.D. steel column with a Waters Separations 2000 system monitored at 254 nm. Recorder chart speed 5 mm/min. A manual step gradient method (flow rate 40 mL/min) was used with a mobile phase of ACN/$H_2O$/$H_2O$-0.5% formic acid. Fractions containing the product were combined and the volatile components were removed in vacuo on a rotary evaporator at 30° C. followed by high vacuum for 18 hours at room temperature. Yield: 0.002 g of yellow film. MS (−): calculated for $C_{80}H_{90}I_3N_8O_{28}S_4^-$; Exact Mass: 2119.1887; Molecular Weight: 2120.5820. UPLC/MS measured $M^{2-}$ 1059.82

Example 65

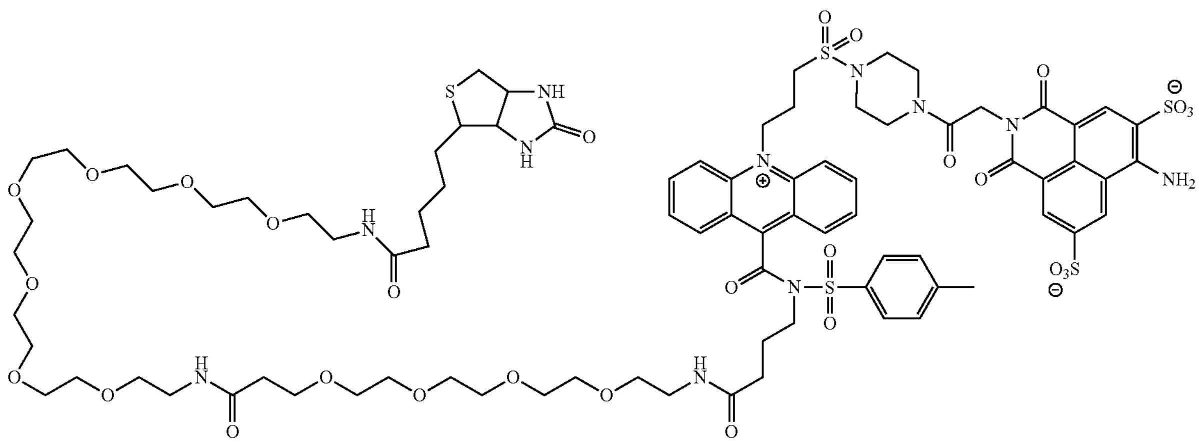

The titled compound was prepared by treating a solution of Example 50, (0.0018 g, 0.0013 mmol) in DMF (0.25 mL) with a solution of biotin-dPEG7-NH2 (Quanta BioDesign catalog #10826, 0.030 g, in DMF (1 mL). The reaction was stirred for 1 hour at room temperature. The resulting solution was purified by reverse phase HPLC using a YMC ODS AQ 30×150 mm I.D. steel column with a Waters Separations 2000 system monitored at 254 nm. Recorder chart speed 5 mm/min. A manual step gradient method (flow rate 40 mL/min) was used ACN/H2O/H2O-0.5 TFA. Fractions containing the product were combined and the volatile components were removed in vacuo on a rotary evaporator at 30° C. followed by high vacuum for 18 hours at room temperature. Yield 0.0024 g of a yellow film. MS (−): calculated for $C_{83}H_{112}N_{11}O_{29}S_5^-$; Exact Mass: 1886.6236; Molecular Weight: 1888.16. UPLC/MS measured 1887.59.

Example 66

Chemiluminescence Data

Protocol for measurement of full chemiluminescence spectrum in the visible wavelength range. Equipment: ANDOR® Shamrock 303i imaging spectrograph, 50 lines/mm ruled grating, 600 nm blaze, aluminum with MgF2 coating, 100 μm entrance slit. ANDOR® iXon$^{EM}$+512×512 CCD camera, model DU-897E-CSO-#BV, back illuminated sensor with 550 nm AR coating. CCD detector chip is E2V Tech CCD97 with electron multiplying readout, with 16 $\mu m^2$ pixel. Thermoelectric cooling was to −70° C. Pixel (column) binning along the vertical (image of slit) for maximum sensitivity was selected covering most of the extent of the chip. Detection wavelength was calibrated using the spectrograph's software by several mercury lines of an Ar—Hg pen lamp, and the resulting spectral dispersion at the detector was approximately 1 nm/pixel. Integration was 5 seconds, which is usually about 5 decay lifetimes of chemiluminescence. Software: ANDOR® Solis for Spectroscopy: X3964, version 4.3. Reagents: ARCHITECT® pretrigger solution, 6E23-65, with detergent, acid, and hydrogen peroxide; ARCHITECT® trigger solution, 6C55-60, with detergent and base. Method: A Hi-Tech Rapid Kinetics Accessory, model SFA-11 was used to mix solutions in the chamber in less than 20 ms per the user manual. The software data acquisition was triggered by hotkey, and two 2.5 mL syringes were pushed manually to achieve 50:50 mixing in the cuvette. The delay from start of integration to mixing was estimated as less than 0.5 sec. The cuvette was oriented giving a 2 mm path length. Samples were typically tested at 500 nanomolar concentration as determined by UV absorbance at the appropriate wavelength per fluorophore.

Protocol for luminometer plate reader measurement of chemiluminescence at multiple wavelengths. Equipment: Berthold Mithras LB940 microplate reader; Optical filters, Semrock Brightline single-band bandpass, multilayer dielectric, 442/46 nm, 531/46 nm; White 96-well plate, MICROFLUOR® I, Thermo 6905. Software: Mikrowin 2000 v. 4.41. Reagents: ARCHITECT® pretrigger solution, 6E23-65, with detergent, acid, and hydrogen peroxide; ARCHITECT® trigger solution, 6C55-60, with detergent and base. 50 μL of test compound in ARCHITECT® Pretrigger solution was placed in a well of the 96-well plate, separate wells were filled for each wavelength measurement. Method: Samples were typically tested at 20-200 pM concentration as determined by absorbance at the appropriate wavelength per fluorophore. In the luminometer, an optical filter of the appropriate wavelength was chosen for the readout. 75 μL of ARCHITECT® Trigger solution was injected into each well just prior to detection. Light counts were measured by the photomultiplier tube with 0.1 sec intervals over 10 sec. Readings were measured in triplicate. Results of the above assays are presented in Table 1.

TABLE 1

Chemiluminescence Data

| Compound | Emission Wavelength Maximum** | Emission 400-500 nm Region | Emission 500-800 nm Region | Relative Intensity† |
|---|---|---|---|---|
| Example 12 | 535 nm | 1% | 99% | 87%‡ |
| Example 13 | 535 nm | 1% | 99% | 40%‡ |
| Example 14 | 532 nm | 3% | 97% | 264% |
| Example 15 | 527 nm | 3% | 97% | 325% |
| Example 16 | 580 nm | 5% | 95% | 324% |
| Example 17 | 525 nm | 3% | 97% | 57% |
| Example 18 | 587 nm | 3% | 97% | 114% |
| Example 19 | 530 nm | 3% | 97% | 297% |
| Example 20 | 530 nm | 2% | 98% | 255% |
| Example 21 | 528 nm | 3% | 97% | 240% |
| Example 22 | 531 nm | 3% | 97% | 291% |
| Example 23 | 532 nm | 2% | 98% | 284% |
| Example 24 | 529 nm | 3% | 97% | 133% |
| Example 25 | 586 nm | 23% | 77% | 98% |
| Example 26 | 526 nm | 18% | 82% | 331% |
| Example 27 | 524 nm | 3% | 97% | 280% |
| Example 28 | 535 nm | 1% | 99% | n.d. |
| Example 29 | 508 nm | 9% | 91% | 165% |
| Example 30 | 574 nm | 9% | 91% | 151% |
| Example 31 | 514 nm | 5% | 95% | 210% |
| Example 32 | 624 nm | 3% | 97% | 207% |
| Example 33 | 557 nm | 40% | 60% | 57% |
| Example 34 | 521 nm | 13% | 87% | 81% |
| Example 35 | 601 nm | 2% | 98% | 167% |
| Example 37 | 439 nm (676 nm) | 87% | 13% | 58% |
| Example 39 | 518 nm | 7% | 93% | 231% |
| Example 40 | 534 nm | 1% | 99% | 334% |
| Example 41 | 560 nm | 10% | 90% | 161% |
| Example 42 | 720 nm | 16% | 84% | 116% |
| Example 44 | 441 nm (817 nm) | 96% | 4% | 37% |
| Example 45 | 537 nm | 9% | 91% | 86% |
| Example 47 | 532 nm | 9% | 91% | 72% |
| Example 54 | 535 nm | 3% | 97% | 37%‡ |
| Example 55 | 440 nm (n.d.) | 94% | 6% | 70%‡ |
| Example 56 | 440 nm (n.d.) | 95% | 5% | 71%‡ |
| Example 57 | 614 nm* | 49% | 51% | 118% |

†Relative total light output from 400-800 nm of the example compound in comparison to CPSP acridinium at a similar concentration (based on literature extinction coefficients of the fluorophore only) as measured by the Andor Shamrock 303i imaging spectrograph, unless otherwise noted. The calculation does not consider differences in measurement efficiency of the CCD camera across the wavelength span or changes in extinction coefficient of the fluorophores when directly linked to acridinium. The calculation was made to simply compare individual compounds within the series shown. Measurements were performed in Architect Pretrigger and Trigger solutions (see methods description).

‡Noted measurements were performed on a Berthold Mithras LB940 microplate reader luminometer.

*Four peaks were observed representative of Europium complex photon emission (590, 614, 650, and 690 nm)

**Emission Wavelength maximum listed in parenthesis denote the wavelength of the shifted-emission band observed when the shifted band was not the maximum emission band.

n.d. = not determined

Example 67

Fluorophore attachment point and linker length were examined using an acetamide linker and isolated 5 and 6 carboxy isomers of fluorescein. The data, shown in FIG. 1, demonstrate that shifted emission is dictated by fluorophore attachment point which may lead to differing overall orientation of the two species or species aggregation and altered ability to shift emission in the short linker configuration.

The 5 and 6 carboxy isomers of fluorescein were further examined using a piperazine linker. Data are shown in FIG. 2. Shifted emission was observed at near 100% efficiency, however differences in intensity were noted between the 5 and 6-isomer moieties. Intensity differences may be attributed to hinderance of the chemical reaction which drives chemiluminescence, or an unfavorable orientation possibly leading to quenching or a non-radiative decay pathway, or compound aggregation leading to altered absorbance/emission profiles. These results illustrate that selection of fluorophore attachment point is an important factor for shifted emission.

Figure 3:
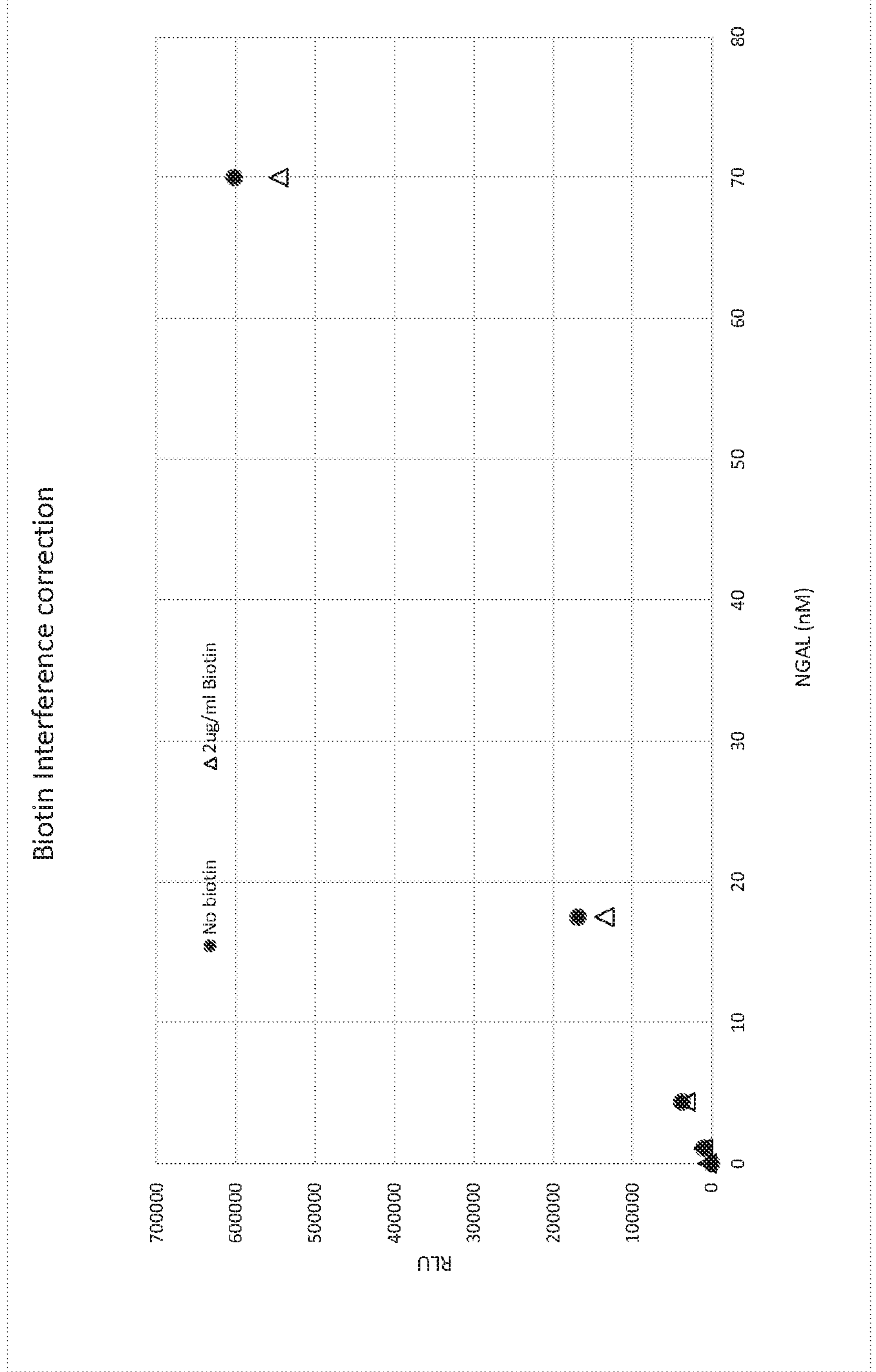
FIG. 3 is a graph of dose response curves from the NGAL assay described in Example 71, including the original biotin-free data as well as the corrected signal from the biotin inference experiment.

Fluorophore attachment point and linker length were also examined for emission efficiency using both a 5/6 carboxy rhodamine dye mixture and a 2 carboxy rhodamine dye. Data are shown in FIG. 3. The 5/6 carboxy rhodamine showed efficient shifted emission while the 2 carboxy rhodamine showed efficient shifted emission in most circumstances with some discrepancies depending on linker type. For example, 2-carboxy Rhodamine B showed efficient stable shifted emission when linked to acridinium through a dimethyl-PEG (2)-diamine linker while the same 2-carboxy Rhodamine B showed increasing levels of acridone emission within the measuring interval when linked to acridinium through a piperazine linkage. These findings indicate the construct may not be stable under the triggering conditions employed. In contrast, 2 carboxy Rhodamine 6G appeared to produce stable shifted emission when linked to acridinium through a piperazine linkage, although shifted emission was only 90% with 10% blue light observed.

Figure 4:
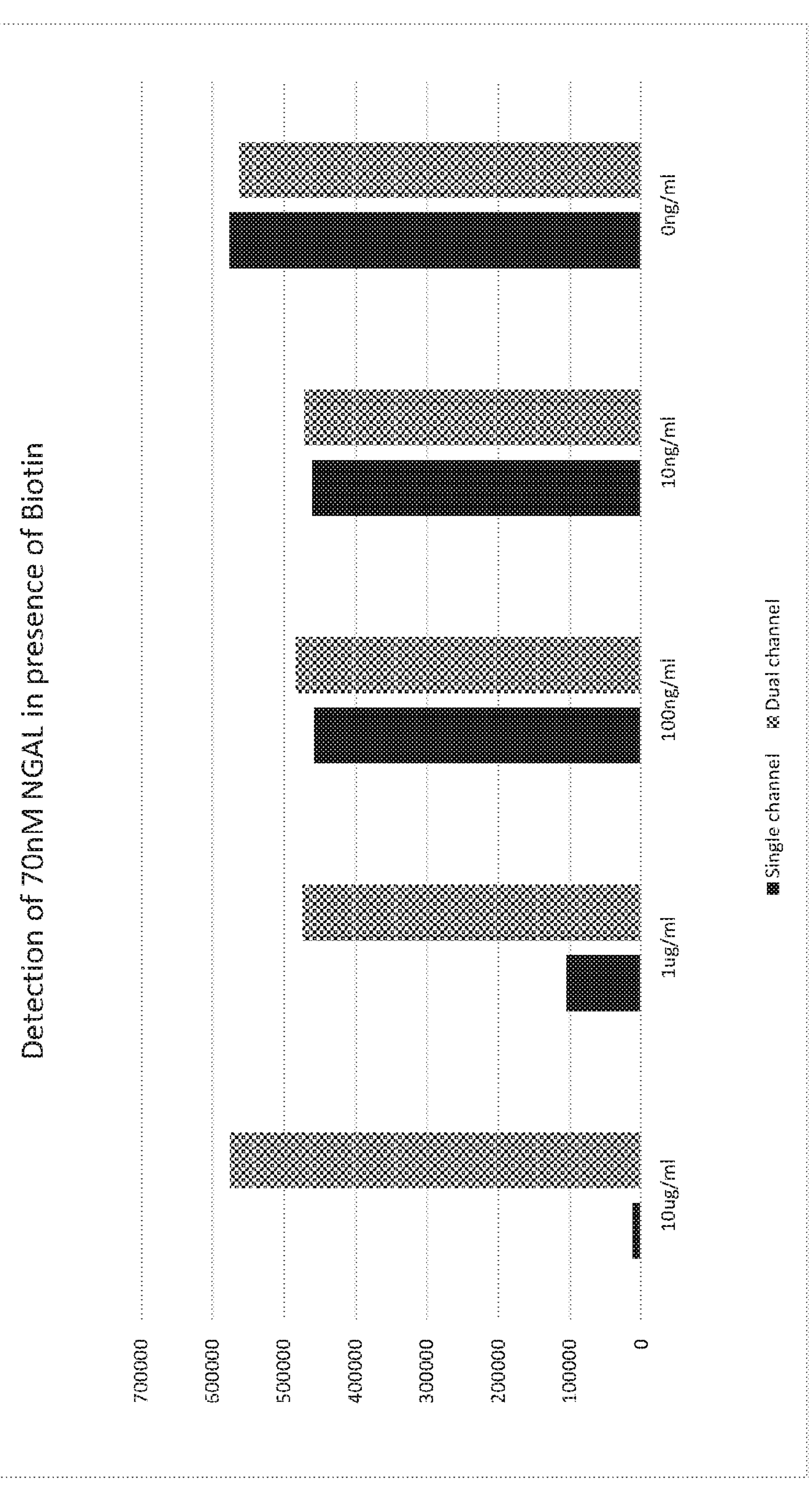
FIG. 4 is a graph showing the data from the NGAL assay described in Example 71, conducted in the presence of biotin in both the single and dual channel systems. In the dual channel system, the corrected signal for NGAL is plotted and remains constant, regardless of biotin concentration.

Initiator attachment point was examined by varying the position of the fluorophore between the sulfopropyl moiety to that of the carboxypropyl moiety of carboxypropyl sulfopropyl acridinium. Attachment to the carboxypropyl group positions the fluorophore on the leaving group of acridinium/acridone molecule. Therefore, on triggering, the fluorophore would dissociate from the resulting acridone moiety. Two fluorescein compounds were attached to acridinium via a xanthene ring attachment point or a phenyl ring attachment point to examine two different molecular orientations. Emission was measured on a luminometer fitted with 442 nm and 531 nm filters. Data are shown in FIG. 4. The fluorescein compounds prepared with carboxypropyl initiator attachment failed to show shifted emission and produced similar wavelength light to that of an acridinium control. Carboxy propyl modification with the preferred piperazine linkage was also attempted and resulted in emission similar to an acridinium control. FIG. 4 shows that the light output and distribution in each filter channel matched that of an acridinium control compound for a selection of the prepared carboxy propyl compounds.

Figure 5:
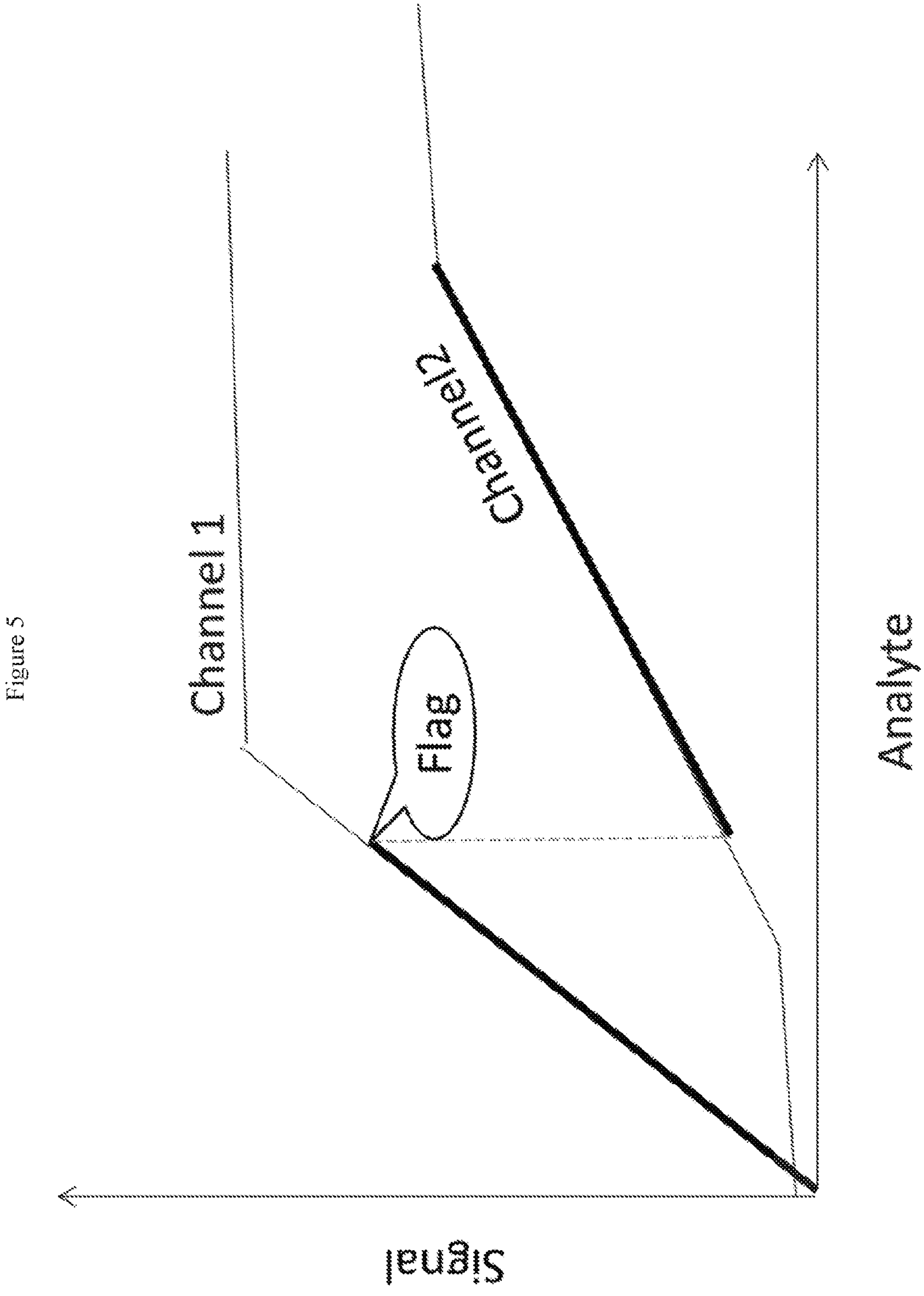
FIG. 5 is a graph illustrating the results of the immunoassay described in Example 72.

Linker type and linker length were examined using diamine linkers of various length and rigidity. A rigid linker may hold the initiator and acceptor in an orientation favorable for shifted emission while the longer linker has the flexibility to bend and twist into a favorable orientation. Data are shown in FIG. 5. Shifted emission was observed at near 100% efficiency for each of the compounds. However, a difference in intensity was noted for the ethylenediamine linker. Intensity differences may be attributed to hinderance of the chemical reaction which drives chemiluminescence, or an unfavorable orientation possibly leading to quenching or a non-radiative decay pathway. These data illustrate that selection of linker may be an important factor for shifted emission.

This example demonstrates that several structural factors are important in developing chemiluminescent acridinium compounds with shifted wavelength emission. The stability of fluorophores to triggering conditions is of significant importance. For example, linkage of cyanine and silicon rhodamine dyes to acridinium resulted in brief shifted emission followed by acridone emission indicating possible construct instability in the triggering matrix. Water solubility is another element needed for function in aqueous based usage such as immunoassays. Overall, selection of linker length, fluorophore attachment point, and initiator attachment drive shifted emission. Without wishing to be limited by theory, these three criteria appear to dictate fluorophore and initiator orientation relative to one another and therefore efficiency of shifted emission.

Example 68

HIV p24 mAb-Acridinium-Lucifer Yellow Conjugate. A stock solution of compound from Example 48 was prepared by reconstituting the dried powder in dimethyl sulfoxide (DMSO). Two 100× dilutions of the stock solution were prepared using a pH 5.5 MES buffer. Concentration was determined by reading absorbance at 370 nm using a Cary 60 UV-Vis spectrophotometer.

Approximately 0.3 mg of HIV p24 mAb was added to 35 μL of 10 mM phosphate buffered saline (PBS) and the pH was adjusted using 5 μL of spiking buffer (250 mM PBS with 7.5% CHAPS, pH 8) to achieve a final reaction pH of 7.5 and a final CHAPS concentration of 0.5% in separate reaction vessels. The vessels were protected from light and the compound from Example 48 stock solution was added to each reaction vessel to achieve a molar input ratio of 6, 9, or 12 over moles of mAb. The reaction vessels were lightly vortexed and then statically incubated overnight, approximately 20 hours, protected from light. After this time, the reaction vessels were centrifuged to separate insoluble aggregates and the protein remaining in the supernatant was was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Protein and Example 48 label concentrations were determined by UV-Vis (280 and 370 nm, respectively). Label to protein incorporation ratio (IR) was determined by dividing the molar concentration of Example 48 to that of the HIV mAb. Final IR values of 2.0, 2.5, and 3.0 were achieved for the 1:6, 1:9, 1:12 molar input ratios, respectively. Protein conjugates were stored at 2-8° C. protected from light until time of use.

Label to protein incorporation ratio was determined by dividing the corrected A280 concentration (A280 absorbance minus A280 contribution of acridinium) by the A370 absorbance of acridinium. Protein conjugates were stored at 2-8° C. until time of use.

Example 69

Anti-Human IgM mAb-Acridinium-Lucifer Yellow Conjugate. A stock solution of compound from Example 48 was prepared by reconstituting the dried powder in DMSO. Two 100× dilutions of the stock solution were prepared using a pH 5.5 MES buffer. Concentration was determined by reading absorbance at 370 nm using a Cary 60 UV-Vis spectrophotometer.

Approximately 0.3 mg of Anti-Human IgM mAb was added to 35 μL of 10 mM phosphate buffered saline (PBS) and the pH was adjusted using 5 μL of spiking buffer (250 mM PBS with 7.5% CHAPS, pH 8) to achieve a final reaction pH of 7.5 and a final CHAPS concentration of 0.5%. The vessel was protected from light and compound from Example 48 stock solution was added to achieve a molar input ratio of 8.5 over moles of mAb. The reaction vessel was lightly vortexed and then statically incubated for 5 hours, protected from light. After this time, the reaction vessel was centrifuged to separate insoluble aggregates and the protein remaining in the supernatant was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Protein and Example 48 label concentrations were determined by UV-Vis (280 and 370 nm, respectively). Label to protein incorporation ratio (IR) was determined by dividing the molar concentration of Example 48 to that of the HIV mAb. A final IR value of 2.6 was achieved for the 1:8.5 molar input ratio. Protein conjugate was stored at 2-8° C. protected from light until time of use.

Example 70

Anti-Human IgG mAb-Acridinium-Fluorescein Conjugate. A stock solution of active ester compound from Example 12 was prepared by reconstituting the dried powder in DMSO to 5 mg/mL by dry weight.

Approximately 2 mg of anti-Human IgG antibody was added to approximately 890 μL of 10 mM phosphate buffered saline pH 8.0 in separate reaction vessels. The vessels were protected from light and active ester of Example 12 solution was added to each reaction vessel to achieve a molar input ratio of 3, 5, or 7 over moles of mAb. The reaction vessels were lightly vortexed and then statically incubated overnight, approximately 16 hours, protected from light. After this time, the reaction vessels were centrifuged to separate insoluble aggregates and the protein remaining in the supernatant was desalted using PD10 G25 desalting columns with a mobile phase of 10 mM PBS pH 6.3. Triggerable counts were measured by adding 70 ng/ml conjugate to ARCHITECT® Pre-Trigger and Trigger on a Mithras LB 940 luminometer. Protein conjugates were stored at 2-8° C. protected from light until time of use.

Example 71

HIV p24 mAb-Acridinium-Fluorescein Conjugate. A 10 mg/mL stock solution of DBCO-PEG-NHS (Click Chemistry Tools A134) was prepared by reconstituting the dried powder in dimethyl sulfoxide (DMSO). The HIV p24 mAb was desalted using a zeba spin column and the antibody concentration was determined by UV-Vis absorbance at 280 nm. The reaction vessel was protected from light and the DBCO solution was added to achieve a molar input ratio of 8 over moles of mAb. The reaction vessel was lightly vortexed and then statically incubated overnight (approximately 20 hours). The resulting solution as purified by HPLC. The DBCO-antibody concentration was again determined by UV-Vis absorbance at 280 nm. A stock solution of the azide compound from Example 12 was prepared at 3.2 μM by dry weight in DMSO. The DBCO-antibody was reacted with the Example 12 azide by incubating 50 μL DBCO-antibody solution with 50 μL Example 12 azide solution in a reaction vessel protected from light overnight (20 hours) at room temperature. Label to protein incorporation ratio (IR) was determined by dividing the molar concentration of Example 12 to that of the HIV mAb. A final IR value of approximately 2.0 was achieved. Protein conjugate was stored at 2-8° C. protected from light until time of use.

Example 72

HIV p24 mAb-Acridinium-BODIPY 493 Conjugate. A stock solution of compound from Example 51 was prepared by reconstituting the dried powder in DMSO. Two 100× dilutions of the stock solution were prepared using a pH 5.0 MES buffer. Concentration was determined by reading absorbance at 370 nm using a Cary 60 UV-Vis spectrophotometer.

Approximately 0.3 mg of HIV p24 mAb was added to approximately 40 μL of 10 mM phosphate buffered saline (PBS) in separate reaction vessels. The vessels were protected from light and compound from Example 51 stock solution was added to each reaction vessel to achieve a molar input ratio of 5, 10, or 15 over moles of mAb. The reaction vessels were lightly vortexed and then statically incubated overnight, approximately 16 hours, protected from light. After this time, the reaction vessels were centrifuged to separate insoluble aggregates and the protein remaining in the supernatant was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Protein and Example 51 label concentrations were determined by UV-Vis (280 and 370 nm, respectively). Label to protein incorporation ratio (IR) was determined by dividing the molar concentration of Example 51 to that of the HIV mAb. The soluble conjugate aggregates produced IR values of 8.8, 7.9, and 8.4 for the 1:5, 1:10, 1:15 molar input ratios, respectively, representing a saturation point for IR with the input ratios investigated. Protein conjugates were stored at 2-8° C. protected from light until time of use.

Example 73

HIV p24 mAb-Acridinium-BODIPY TEXAS RED (TR) Conjugate. A stock solution of compound from Example 52 was prepared by reconstituting the dried powder in DMSO. Two 100× dilutions of the stock solution were prepared using a pH 5.5 MES buffer. Concentration was determined by reading absorbance at 370 nm using a Cary 60 UV-Vis spectrophotometer.

Approximately 0.3 mg of HIV p24 mAb was added to approximately 7.5 μL of 10 mM phosphate buffer in separate reaction vessels. The vessels were protected from light and compound from Example 52 stock solution was added to each reaction vessel to achieve a molar input ratio of either 1:10. DMSO was added in increasing amounts up to 30% reaction volume to help solubilize the Example 52 compound. The final reaction volume was 25 μL. The reaction vessels were lightly vortexed and then statically incubated overnight, approximately 16 hours, protected from light. After this time, the reaction vessels were centrifuged to separate insoluble aggregates and the protein remaining in the supernatant was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Soluble aggregates were observed and isolated for further testing. Protein conjugates were stored at 2-8° C. protected from light until time of use.

Example 74

HIV p24 mAb-PEG-Acridinium-Lucifer Yellow Conjugate. A stock solution of compound from Example 50 was prepared by reconstituting the dried powder in DMSO. Two 100× dilutions of the stock solution were prepared using a pH 5.5 MES buffer. Concentration was determined by reading absorbance at 370 nm using a Cary 60 UV-Vis spectrophotometer.

Approximately 0.3 mg of HIV p24 mAb was added to 35 μL of 10 mM phosphate buffered saline (PBS) and the pH was adjusted using 5 μL of spiking buffer (250 mM PBS with 7.5% CHAPS, pH 8) to achieve a final reaction pH of 7.5 and a final CHAPS concentration of 0.5%. The vessel was protected from light and compound from Example 50 stock solution was added to the reaction vessel to achieve a molar input ratio of 20 over moles of mAb. The reaction vessel was lightly vortexed and then statically incubated overnight, approximately 16 hours, protected from light. After this time, the reaction vessel was centrifuged to separate insoluble aggregates and the protein remaining in the supernatant was purified by HPLC on a TSKGel G3000SWxl column with a mobile phase of 10 mM PBS pH 6.3. A flow rate of 1 mL/min was used and the eluent was monitored with a Photodiode array detector at 280 nm, 370 nm, and 431 nm. Protein and Example 50 label concentration was determined by UV-Vis (280 and 370 nm, respectively). Label to protein incorporation ratio (IR) was determined by dividing the molar concentration of Example 50 to that of the HIV mAb. A final IR value of 4.0 was achieved for the 1:20 molar input ratio. Protein conjugates were stored at 2-8° C. protected from light until time of use.

Example 75

Anti-human IgG MAB-Lucifer Yellow-CPSP-PEG4 Acridinium Conjugate. A stock solution of Lucifer Yellow-CPSP-PEG4 active ester (Example 50) was prepared by reconstituting the dried powered in DMSO to 9.3 mg/mL.

Approximately 1 mg of anti-Human IgG mAb was dialyzed against 50 mM potassium phosphate 150 mM potassium chloride pH 8.0 at a ratio of 0.2 L/mL. After dialysis, 0.7 mg of antibody was added to 60 μL of potassium phosphate buffer containing cyclodextrin (30% in reaction), pH 8.0 in a light protected reaction vessel. Lucifer Yellow-CPSP-PEG4 acridinium solution was added to the reaction vessel to achieve a molar input ratio of 10 over moles of mAb. The reaction vessel was lightly vortexed and incubated statically overnight, approximately 22 hours, protected from light. The reaction vessel was centrifuged to separate insoluble aggregates and the remaining supernatant was purified via SEC-HPLC on a G3000 column with a mobile phase of 10 mM PBS pH 6.3. The conjugate IR was determined via UV-VIS, measuring A280 and A370. The protein conjugate was stored at 2-8° C.

Example 76

Anti-TSH MAB-Lucifer Yellow-CPSP-PEG4 Acridinium Conjugate. A stock solution of Lucifer Yellow-CPSP-PEG4 active ester (Example 50) was prepared by reconstituting the dried powered in DMSO to 9.3 mg/mL.

Approximately 3 mg of anti-TSH mAb was desalted over Zeba desalting columns into phosphate buffer pH 8.0. After desalting, 2.6 mg of antibody was added to 200 μL of phosphate buffer containing cyclodextrin (30% in reaction), pH 8.0 in a light protected reaction vessel. Lucifer Yellow-CPSP-PEG4 acridinium solution was added to the reaction vessel to achieve a molar input ratio of 7.5 over moles of mAb. The reaction vessel was lightly vortexed and incubated statically overnight, approximately 18 hours, protected from light. The reaction vessel was centrifuged to separate insoluble aggregates and the remaining supernatant was purified via SEC on a Sephacryl S-300 column with a mobile phase of 10 mM PBS pH 6.3. The conjugate IR was determined via UV-VIS, measuring A280 and A370. The protein conjugate was stored at 2-8° C.

Example 77

Anti-NGAL mAb biotin-Acridinium-Lucifer Yellow (LY). A stock solution of biotin active ester (purchased) and acridinium lucifer yellow (Example 48) were prepared by reconstituting the dried powders in DMSO to 10 mg/mL by dry weight, separately.

Approximately 200 μg of anti-NGAL IgG antibody was added to approximately 100 μL of 10 mM phosphate buffered saline pH 8.0. The vessels were protected from light and active ester of biotin solution was added to achieve a molar input ratio of 5 times over moles of mAb. The reaction vessels were lightly vortexed and then statically incubated overnight, approximately 16 hours, protected from light. The solution was then loaded onto a desalting column (Zeba Spin desalting column from Thermo Scientifics). The concentration of the labeled antibody was determined by measuring the absorption spectrum at A280 nm. The extinction coefficient for A280 was 1.45/mg/mL. The purified protein was then reacted with active ester of acridinium-lucifer yellow at molar ratio of 1:0.5 (mAb: Acridinium-LY) for another 16 hours. The amount of acridinium-LY used in labeling was purposely kept low. It is preferable to remove the unreacted acridinium-LY with another desalting column, but the product can also be used without further purification. Protein conjugates were stored at 2-8° C. protected from light until time of use.

Example 78

This example demonstrates a method of detecting a macroprolactin interferent in an immunoassay for detecting prolactin in accordance with the present disclosure.

The present disclosure describes the use of differentiated reporter conjugates (emission wavelength or time-resolved emission), one which targets prolactin and one that targets macroprolactin/big-prolactin (interference molecule). The conjugate which targets the interference molecule may be an anti-human IgG, an anti-macroprolactin Ab, or any other construct that preferentially binds to macroprolactin in the presence of prolactin. The capture agent (solid support coated with anti-prolactin antibody or other capture agent) captures both prolactin and macroprolactin in the sample. The two conjugates would then be added, and luminescence read via a detection system capable of differentiating emission wavelength (for example multiple, filtered photomultiplier tube (PMT) setup or charge coupled device (CCD) camera) or time-resolved luminescence. The presence of macroprolactin would be determined using either a threshold value for macroprolactin conjugate response or as a ratio of the prolactin conjugate versus macroprolactin conjugate responses.

To this end, an anti-Human IgG mAb-acridinium-lucifer yellow conjugate may be prepared. A stock solution of acridinium-lucifer yellow active ester is prepared by reconstituting dried powder in DMSO. Two 100× dilutions of the stock solution is prepared using a pH 5.5 MES buffer. Concentration is determined by reading absorbance at 370 nm using a Cary 60 UV-Vis spectrophotometer.

Approximately 0.3 mg of anti-human IgG mAb is added to 35 μL of 10 mM phosphate buffered saline (PBS) and the pH was adjusted using 5 μL of spiking buffer (250 mM PBS with 7.5% CHAPS, pH 8) to achieve a final reaction pH of 7.5 and a final CHAPS concentration of 0.5%. The vessel is protected from light and the label stock solution is added to achieve a molar input ratio of 8.0 over moles of mAb. The reaction vessel is lightly vortexed and then statically incubated for 5 hours, protected from light. After this time, the reaction vessel is centrifuged to separate insoluble aggregates and the protein remaining in the supernatant is purified by HPLC on a TSKGel G3000SWxl column with a mobile phase of 10 mM PBS pH 6.3. A flow rate of 1 mL/min is used and the eluent is monitored with a Photodiode array detector at 280 nm, 370 nm, and 431 nm. Protein and label concentrations are determined by UV-Vis (280 and 370 nm, respectively). Label to protein incorporation ratio (IR) is determined by dividing the molar concentration of acridinium-lucifer yellow to that of the anti-human IgG mAb. Protein conjugate is stored at 2-8° C. and protected from light until time of use.

A prolactin and macroprolactin combination assay for interference detection is then performed. Specifically, prolactin and marcroprolactin detection kits are assembled by diluting an anti-macroprolactin mAb-acridinium-lucifer yellow conjugate for macroprolactin detection and an anti-prolactin mAb-acridinium conjugate (50 ng/mL) for prolactin detection in ARCHITECT® (Abbott, Abbott Park, IL) prolactin conjugate diluent containing phosphate buffer and protein (piscine and bovine) stabilizers. The experimental conjugate bottle is paired with Abbott on-market prolactin microparticles (Abbott list number 7K76). Assay testing is performed on an ARCHITECT® automated immunoassay analyzer modified with a two-channel optics configuration. Briefly, a dual photomultiplier tube (PMT) assembly is constructed in which a dichroic mirror with a wavelength cutoff at 500 nm is used to reflect low wavelength light (blue) to a vertical PMT, while higher wavelength light (green) passes through the mirror to a second PMT. Appropriate filters are placed after the dichroic mirror to further filter the desired light prior to reaching the respective PMTs. Hardware on the ARCHITECT® instrument is used to read the output from the reflected (blue) PMT, while a separate counter module and laptop computer interface is used to compile signal from the in-line (green) PMT. A custom IDL code is used to automatically process the signal from the in-line PMT.

Assay testing is performed using the on-market ARCHITECT® prolactin assay file which performs a 2-step immunoassay using CMIA technology. Briefly, sample, ARCHITECT® Wash Buffer, assay diluent, and microparticles are combined in the first step. Prolactin and macroprolactin present in the sample bind to the anti-prolactin-coated microparticles. After washing, the acridinium-labeled conjugates are added and bind to the prolactin and macroprolactin captured on the microparticles. Following another wash cycle, pre-trigger and trigger solutions are added to the reaction mixture to promote the chemiluminescent signal which is measured as relative light units (RLU).

An interference test is performed in which human plasma containing a known quantity of prolactin is spiked with increasing levels of macroprolactin from 0 ng/ml to a pre-determined upper range. Signal produced in both data channels is processed and analyzed. The presence of macroprolactin interference is determined by using both a threshold value for macroprolactin conjugate response and as a ratio of the prolactin conjugate response versus macroprolactin conjugate response. Results will be verified by polyethylene glycol precipitation procedure.

Example 79

This example demonstrates a method of detecting anti-thyroglobulin antibody interferents in a thyroglobulin (Tg) detection immunoassay in accordance with the present disclosure.

Immunoassay detection of Tg in the presence of anti-Tg antibodies is important because many Tg assays fail to recognize TgAb-complexed Tg and, therefore, underestimate the true concentration of Tg. This interference is by far the major issue facing the clinical utility of sandwich format Tg immunoassays (Feldt-Rasmussen, U and Rasmussen, K., *J Endocrinol Invest.*, 8:571-576 (1985); and Schaadt et al., *Thyroid,* 5(3): 165-170 (1995)). Anti-Tg antibodies are detected in 30-60% of cases of thyroid carcinoma patients, demonstrating that the problem is relatively widespread. Quantitative assessment of anti-Tg antibodies is recommended with every measurement of Tg to identify potential anti-Tg Ab interference (Haugen et al., *Thyroid,* 26(1): 1-133 (2016); and Perros et al., *Clin Endocrinol.,* 81(s1): 1-122 (2014)).

Differentiated reporter conjugates (emission wavelength or time-resolved emission) may be used to create a Tg/anti-Tg combination assay (Tg combo) in accordance with the present disclosure. The assay format includes a Tg-coated microparticle paired with an anti-Tg conjugate and a differentiated anti-human IgG antibody conjugate. Tg from the sample competes with the Tg microparticle for binding of the anti-Tg conjugate (competitive assay), while the anti-human IgG conjugate will bind to and detect anti-Tg antibodies from the sample captured by the Tg microparticle (sandwich format). Luminescence is read via a detection system capable of differentiating emission wavelength (e.g., multiple, filtered photomultiplier tube (PMT) setup or charge coupled device (CCD) camera) or time-resolved luminescence. The Tg combo assay eliminates the need to perform two separate assays for prognosis.

To this end, a Tg combo detection kit was assembled by making two conjugates, an anti-Tg mAb-acridinium conjugate for Tg detection and an anti-human IgG mAb-acridinium-lucifer yellow conjugate (as described in Example 75, 40 ng/mL final) for anti-Tg antibody detection, both diluted in ARCHITECT® anti-Tg conjugate diluent containing MES buffer and protein (bovine) stabilizers. The experimental conjugate bottles were paired with Abbott on-market Anti-Tg microparticles (Abbott list number 2K46). Assay testing was performed on an ARCHITECT® (Abbott, Abbott Park, IL) automated immunoassay analyzer modified with a two-channel optics configuration. Briefly, a dual photomultiplier tube (PMT) assembly was constructed in which a dichroic mirror with wavelength cutoff at 500 nm was used to reflect low wavelength light (blue) to a vertical PMT, while higher wavelength light (green) passed through the mirror to a second PMT. Appropriate filters were placed after the dichroic mirror to further filter the desired light prior to reaching the respective PMTs. Hardware on the ARCHITECT® instrument was used to read the output from the reflected (blue) PMT, while a separate counter module and laptop computer interface were used to compile signal from the in-line (green) PMT. A custom computer program (IDL code) was developed to automatically process the signal from the in-line PMT.

Assay testing was performed using CMIA technology in a combined 1-step/2-step format. Briefly, sample, assay diluent, microparticles and the anti-Tg mAb conjugate were combined and incubated, followed by a wash step and the second conjugate incubation step. Following a wash cycle, pre-trigger and trigger solutions were added to the reaction mixture to promote the chemiluminescent signals which were measured as relative luminescence units (RLU).

Figure 1B:
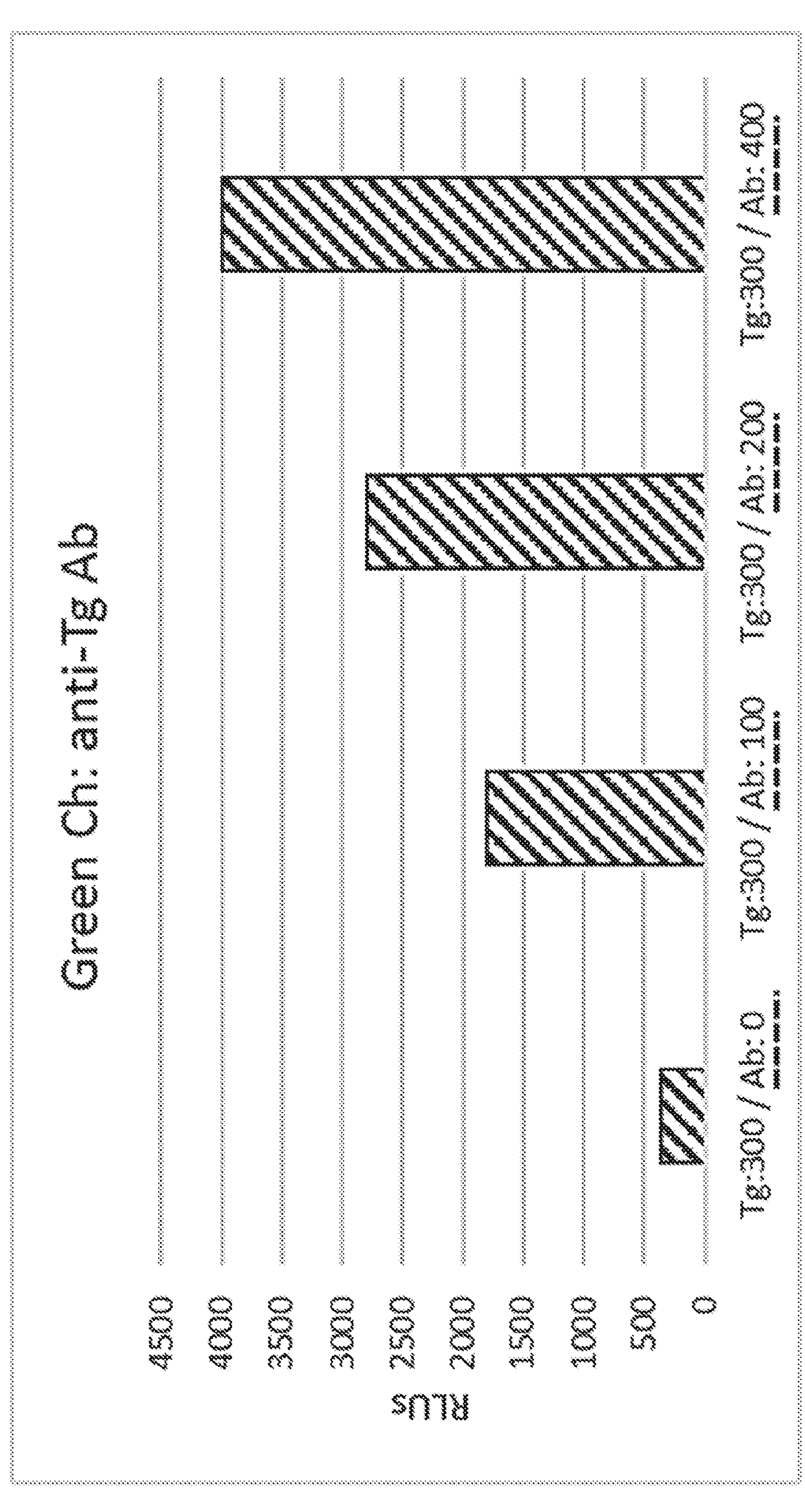
FIG. 1B is a graph showing the concentration of anti-Tg antibody measured in the Tg/anti-Tg combination assay described in Example 68. Chemiluminescent signals were measured as relative luminescence units (RLU).

An interference test was performed in which four samples of human plasma were mixed such that all 4 contained 300 ng/ml of Tg, while anti-Tg antibody was added to the following levels: 0, 100, 200, and 400 IU/mL. Signal produced in both data channels was processed and analyzed, and the results are shown in FIGS. 1A and 1B, The presence of anti-Tg antibody interference was determined by using both a threshold value for anti-Tg antibody conjugate response and as a ratio of the anti-Tg antibody conjugate response versus Tg conjugate response.

Example 80

This example demonstrates the ability to detect and quantify troponin, having corrected the bias caused by the presence of the interfering anti-troponin antibody, using the anti-troponin antibody concentration information detected and quantified in a second color channel.

The Abbott on-market troponin assay consists of microparticles, coated with anti-troponin capture antibodies, which capture troponin molecules that are subsequently detected with an acridinium-labeled, second anti-troponin antibody-conjugate. In the event that a patient sample also contains anti-troponin antibodies developed by the human immune system, these antibodies will also bind to troponin, blocking capture and/or detection of troponin in the assay and leading to an artificially lowered troponin signal.

Figure 2A:
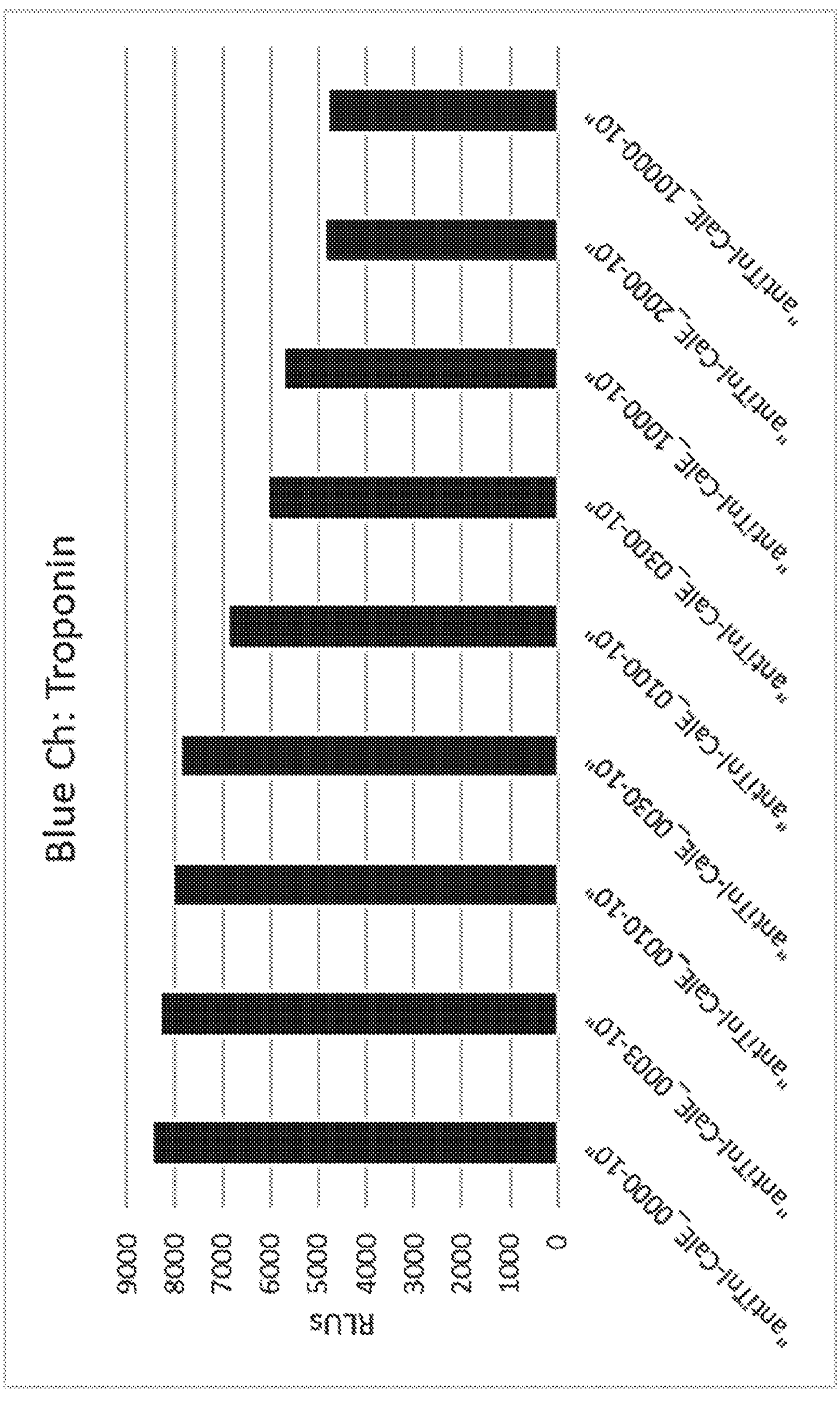
FIG. 2A is a graph showing the concentration of troponin (TnI) measured in the TnI/anti-TnI combination assay described in Example 69.
Figure 2B:
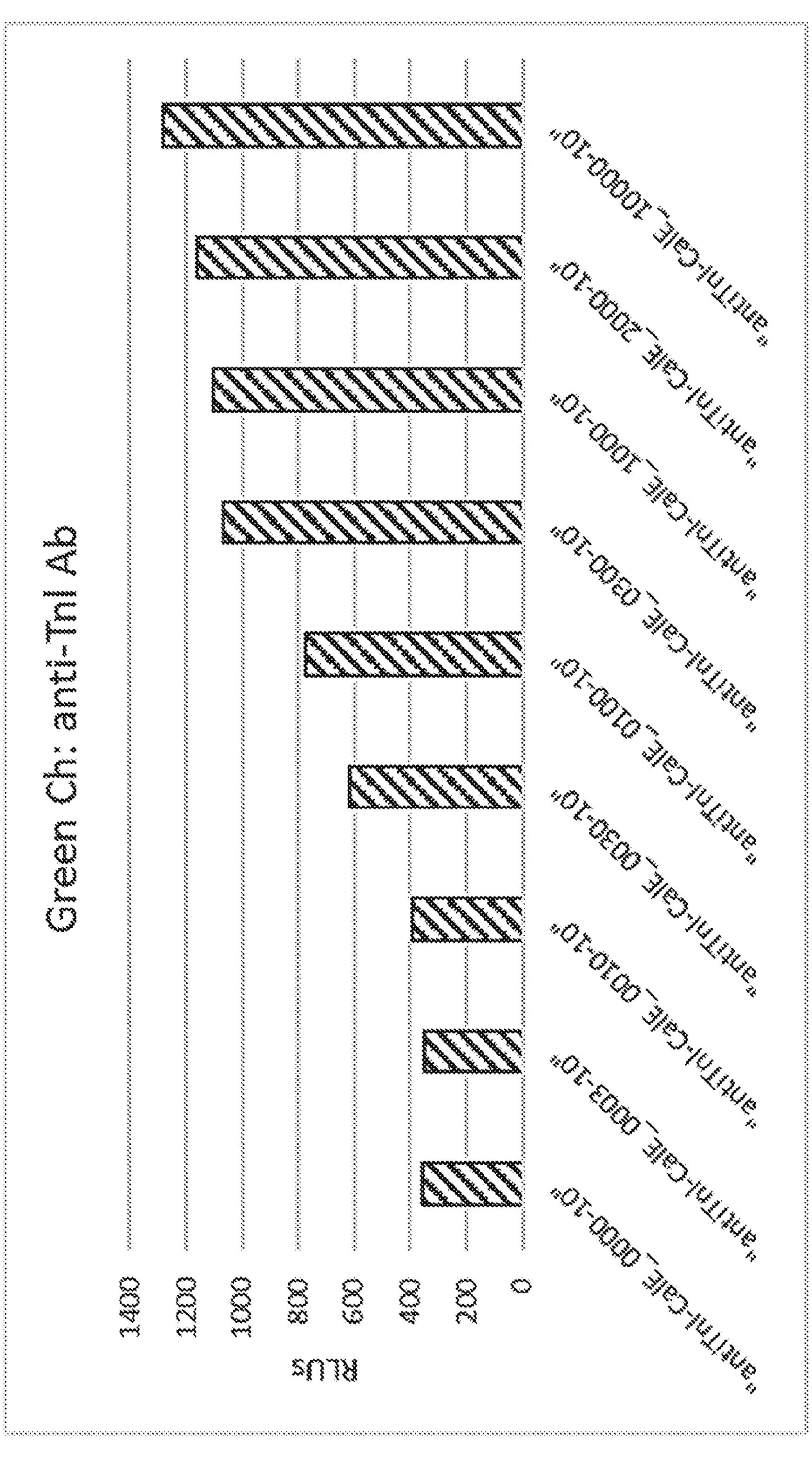
FIG. 2B is a graph showing the concentration of anti-TnI antibody measured in the TnI/anti-TnI combination assay described in Example 69. Chemiluminescent signals were measured as relative luminescence units (RLU).
Figure 2C:
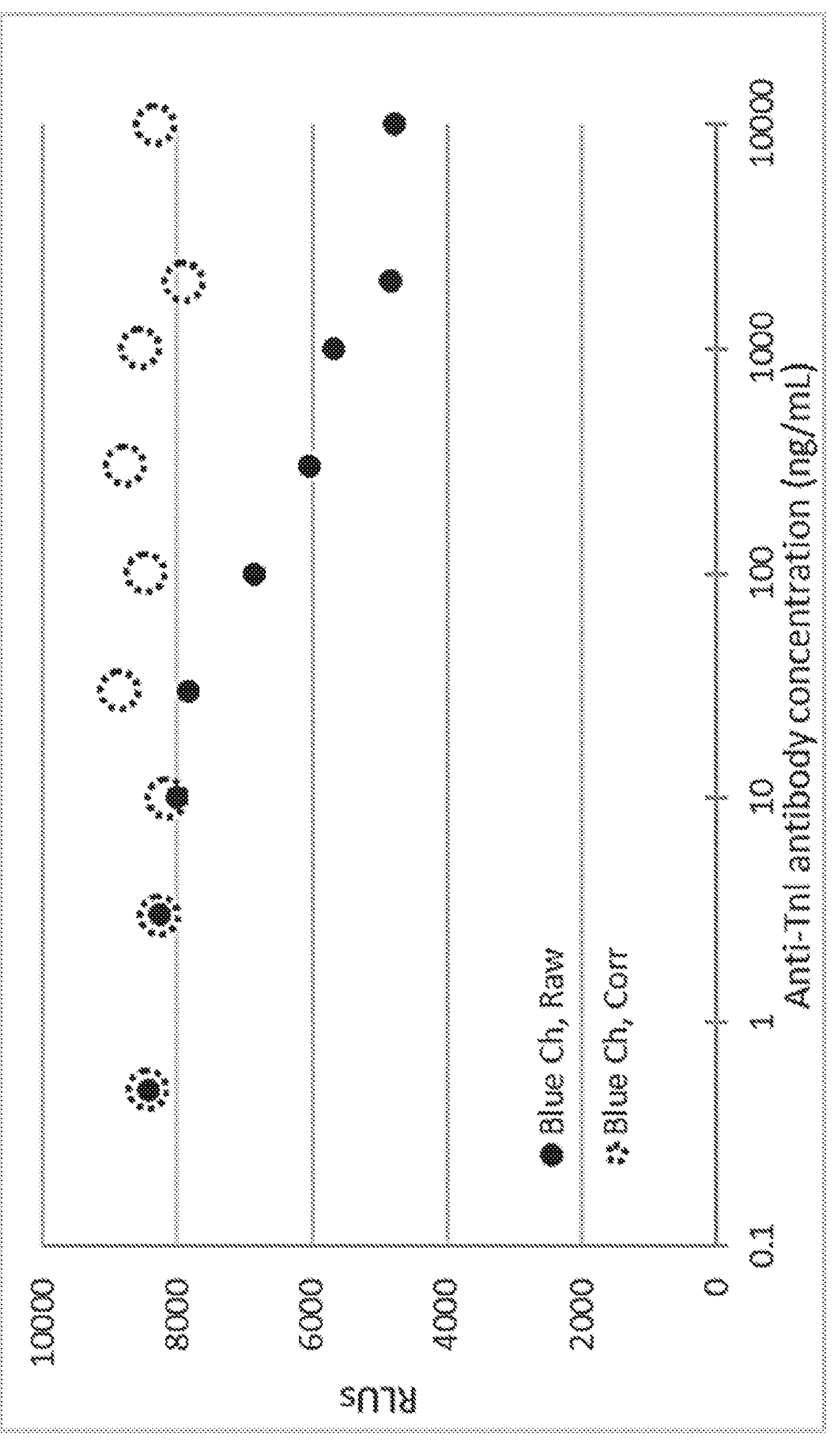
FIG. 2C is a graph showing that the blue channel signal levels can be increased by 3.8 times their respective green channel levels, generating a corrected, blue-channel troponin signal that successfully accounts for the presence of interfering antibody.

Here, a third anti-troponin human-chimeric antibody was mixed into the samples (to mimic the human autoantibody respone) and a green channel conjugate was constructed consisting of anti-human antibody labeled with Lucifer-yellow-linked acridinium conjugate (Example 75). Nine 100 μL samples of Troponin Calibrator E (10 ng/mL) were mixed to contain increasing levels of the human chimeric anti-troponin antibody (0, 3, 10, 30, 100, 300, 1000, 2000, and 10,000 ng/mL). The mixed samples were run on an Abbott ARCHITECT® (Abbott, Abbott Park, IL) instrument as a two-step assay in which the microparticles, sample, and STAT Troponin conjugate (blue channel) were mixed and incubated for 18 minutes. Following a wash step, microparticles with bound complexes were incubated with the second conjugate (200 ng/mL, green channel) for 4 minutes. After one more wash cycle, pre-trigger and trigger were added to drive the chemiluminescent reaction. The green and blue signals, separated by a dichroic mirror (500 nm cutoff), were detected by two PMTs. The correlation between the blue signal decrease (bias) and the green channel increase (interferent concentration level) was determined to be a line with slope ~3.8. As shown in FIGS. 2A-2C, the blue channel signal levels can be increased by 3.8 times their respective green channel levels, generating a corrected, blue-channel troponin signal that successfully accounts for the presence of interfering antibody.

This example demonstrates the utility of dual channel detection and dual channel calibration to mathematically eliminate in sample interference/cross reaction.

Example 81

A dual channel assay system can be used to detect and correct for biotin interference.

In the "capture on the fly" immunoassay format, the capture antibody is labeled with biotin and the detection antibody is labeled with a reporter group (e.g. acridinium). After reacting with analyte, the immunocomplex is pulled down using streptavidin-coated microparticles. If the patient already has a high level of biotin present in their bloodstream, the amount of immunocomplex captured by the microparticles could be compromised, as the free biotin also binds to the streptadivin-coated microparticles and blocks the immunocomplex. This results in reduced signal and false negatives.

To address this phenomenon, a capture antibody will be generated having dual labels (biotin and a reporter group, Label 2). The detection antibody will be labeled with a different reporter group (Label 1). Sample containing analyte will react with the capture antibody and detection antibody in aqueous solution, forming immunocomplexes. The immunocomplexes are then captured by streptavidin microparticles. After a washing step, signals emitted from the detection antibody (Label 1) and the capture antibody (Label 2) will be measured simultaneously in Channel 1 and Channel 2, respectively. In the absence of biotin interference, the capture antibody signal (Channel 2) will remain constant, regardless of analyte concentration, as it is purely determined by the pull-down efficiency. Signal from the detection antibody (Channel 1) will reflect analyte concentration. When biotin interference is present, the signal from both channels will be reduced for all analyte concentrations. However, the signal from Channel 2 can be used to correct the signal from Channel 1 against the biasing effect of biotin interference.

Using the above system, experiments were performed to detect neutrophil gelatinase-associated lipocalin (NGAL) in the presence of a high excess level of biotin. For the first experiment, the following reagents were used: anti-NGAL mAb A labeled with biotin and Lucifer-Yellow-acridinium (capture antibody), anti-NGAL mAb B labeled with acridinium (detection antibody), and streptavidin-coated microparticles (M270) (ThermoFisher Scientific, Waltham, MA). The capture and detection antibodies can simultaneously bind to NGAL and form an immunocomplex. Various concentrations of NGAL were added to a mixture containing both the capture antibody and detection antibody, and after a brief incubation, streptavidin coated microparticles were added to the solution to pull down the capture antibody and immunocomplex. A washing step was then introduced to remove unbound antibody and analytes. Finally, signals from capture antibody (Channel 2), and detection antibody (Channel 1) were simultaneously measured. The same experiment was repeated with slight modification to introduce 2 μg/ml biotin to each sample. The results are shown in Tables 2 and 3, and FIG. 3.

TABLE 2

| No biotin added | | |
|---|---|---|
| NGAL (nM) | Channel 1 | Channel 2 |
| 70 | 602079 | 50378 |
| 17.5 | 168984 | 52029 |
| 4.4 | 37773 | 57467 |
| 1.1 | 9976 | 56908 |
| 0 | 435 | 64733 |

TABLE 3

| 2 μg/ml biotin added to each sample | | | | |
|---|---|---|---|---|
| NGAL (nM) | Channel 1 | Channel 2 | Correction factor | Corrected Channel 1 |
| 70 | 73362 | 8701 | 64733/8701 = 7.4 | 73362 × 7.4 = 545785 |
| 17.5 | 12282 | 5862 | 64733/5862 = 11.0 | 12282 × 11.0 = 135619 |
| 4.4 | 3283 | 6540 | 64733 6540 = 10.9 | 3283 × 10.9 = 32498 |
| 1.1 | 1013 | 5776 | 64733/5776 = 11.2 | 1013 × 11.2 = 11358 |
| 0 | 528 | 5598 | 64733/5598 = 11.6 | 528 × 11.6 = 6101 |

In the presence of 2 μg/ml biotin, the signal from Channel 1 and Channel 2 both decreased significantly (compare Table 3 vs Table 2). If a correction factor is used, however, the signal from Channel 1 can be corrected by multiplying the correction factor (4$^{th}$ column) with the Channel 1 signal (2$^{nd}$ column). The correction factor for each sample was calculated from the ratio of the control signal (bolded value in Table 1) to each corresponding Channel 2 signal (3$^{rd}$ column).

A second experiment was performed using the following reagents: anti-NGAL mAb A labeled with biotin (Capture Antibody 1), anti-NGAL mAb A labeled with biotin and Lucifer-Yellow-acridinium (Capture Antibody 2), anti-NGAL mAb B labeled with acridinium (Detection Antibody), and streptavidin-coated microparticles (M270) (ThermoFisher Scientific, Waltham, MA). Single and dual channel systems were evaluated. For the single channel system, 100 μL of 70 nM NGAL was added to 900 μL of a mixture containing both Capture Antibody 1 and Detection Antibody), and aliquoted to 5 sample cups. Various amounts of biotin were spiked into the sample cup (final biotin concentration ranged from 10 ng/mL to 10 μg/mL). After a brief incubation, streptavidin-coated microparticles were added to reaction mixture, followed by a washing step to remove unbound biotin, antibody, and analytes. Finally, the signal from the Detection Antibody (Channel 1) was measured.

For the dual channel system, 100 μL of 70 nM NGAL was added to the 900 μL of antibody mixture (containing both the Capture Antibody 2 and Detection Antibody), and aliquoted to 5 sample cups. The same amounts of biotin used for the single channel were again spiked into the sample cups, followed by equivalent incubation and wash steps. The signals from both Capture Antibody 2 (Channel 2) and Detection Antibody (Channel 1) were simultaneously measured.

The results for both single and dual channel systems are shown in Table 4 and FIG. 4. Table 4 shows the signals measured from a series of samples in which the NGAL concentration was held constant but measured in the presence of various amounts of biotin using both a single channel and dual channel detection setup.

TABLE 4

| Signals measured in an NGAL assay with increasing biotin interference | | | | | |
|---|---|---|---|---|---|
| | Single Channel system: | Dual Channel system: Capture Ab 2 | | | |
| Biotin | Capture Ab1 Channel 1 | Channel 1 | Channel 2 | Correction Factor | Corrected Channel 1 |
| 0 | 575756 | 563074 | 51148 | 11.0 | 563074 |
| 10 ng/mL | 459850 | 491884 | 53345 | 9.2 | 471620 |
| 100 ng/mL | 457923 | 435284 | 46047 | 9.5 | 483499 |
| 1 μg/mL | 104880 | 80628 | 8704 | 9.3 | 473814 |
| 10 μg/mL | 11977 | 9261 | 824 | 11.2 | 574857 |

In the single channel system, excess amounts of biotin significantly reduced the assay signal (Table 4, 2$^{nd}$ column). In the dual channel system, excess amounts of biotin also significantly reduced the assay signal (Table 4, 3$^{rd}$ column), but Channel 2 could be used to generate a correction factor (Table 4, 4$^{th}$ column), and the corrected Channel 1 (Table 4, last column) could recover the true NGAL signal level despite the interference of biotin.

Example 82

This example describes a method of expanding the dynamic range of a two-step immunoassay.

In this two-step immunosandwich assay format, target analytes are first captured by microparticles coated with antibody, after unbound analytes are removed, then detected with two antibody conjugates which (i) have different affinities to the target analyte, (ii) are constructed with distinct labels, and (iii) are present at different concentrations. As shown in FIG. 5, the conjugate with higher affinity for the target analyte (conjugate 1) will be present at a relatively low concentration to minimize nonspecific binding. The signal emitted by conjugate 1 will be measured in channel 1 and will plateau at high analyte concentrations once all of the available conjugates in the reaction solution are bound to the analyte. In contrast, the signal from conjugate 2/channel 2 (lower affinity, high concentration) will be relatively flat at low analyte concentration, but will have a better dose-response at high analyte concentration. Used in combination, conjugates 1 and 2 enable the assay to cover a wider dynamic range. The piecewise calibration curve, built from known analyte concentrations, will comprise a first segment from channel 1 (shown in bold), a flag to delineate the boundary, and a second segment from channel 2 (shown in bold).

Example 83

This example describes a modified one-step immunoassay format with extended dynamic range in accordance with the present disclosure.

Figure 6:
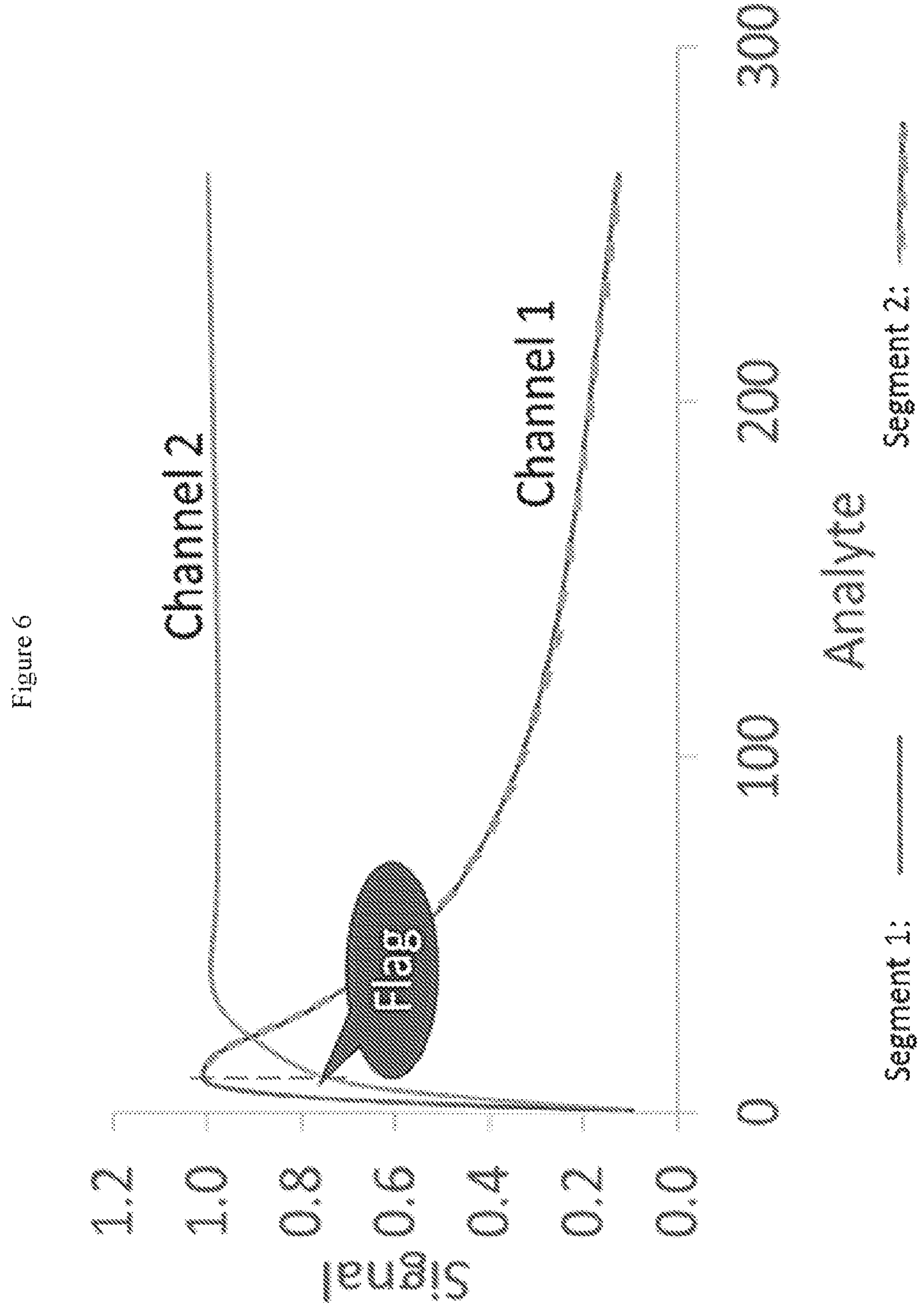
FIG. 6 is a graph illustrating the results of the immunoassay described in Example 73.

Here, one capture antibody and one detection antibody are used, but the detection antibody is composed of two sub-populations, comprising two distinct labels (Label 1 or Label 2). In the first assay step, the analyte, microparticles, and conjugate with Label 1 (Conjugate 1) are reacted together. After incubation and a washing step, the same detection antibody tagged with Label 2 (Conjugate 2) is added. After a second incubation and washing step, signals are read simultaneously from channel 1 (for detecting Conjugate 1) and channel 2 (for detecting Conjugate 2), as shown in FIG. 6. Signal from channel 1 is used to generate a calibration curve from a set of known analyte concentrations. Signal from channel 2 is used as a flag signal to indicate whether the ascending section or the descending section of the calibration curve should be referenced for a given measurement result. For example, if the signal from channel 2 is lower than the assigned flag value, then signal from channel 1 is compared to the ascending section of the calibration curve to determine analyte concentration. If the signal from channel 2 is higher than the flag value, then the descending section of the calibration curve should be used to determine analyte concentration. The flag value is measured from channel 2 and is defined to correspond with the inflection point in the channel 1 calibration curve.

Figure 7A:
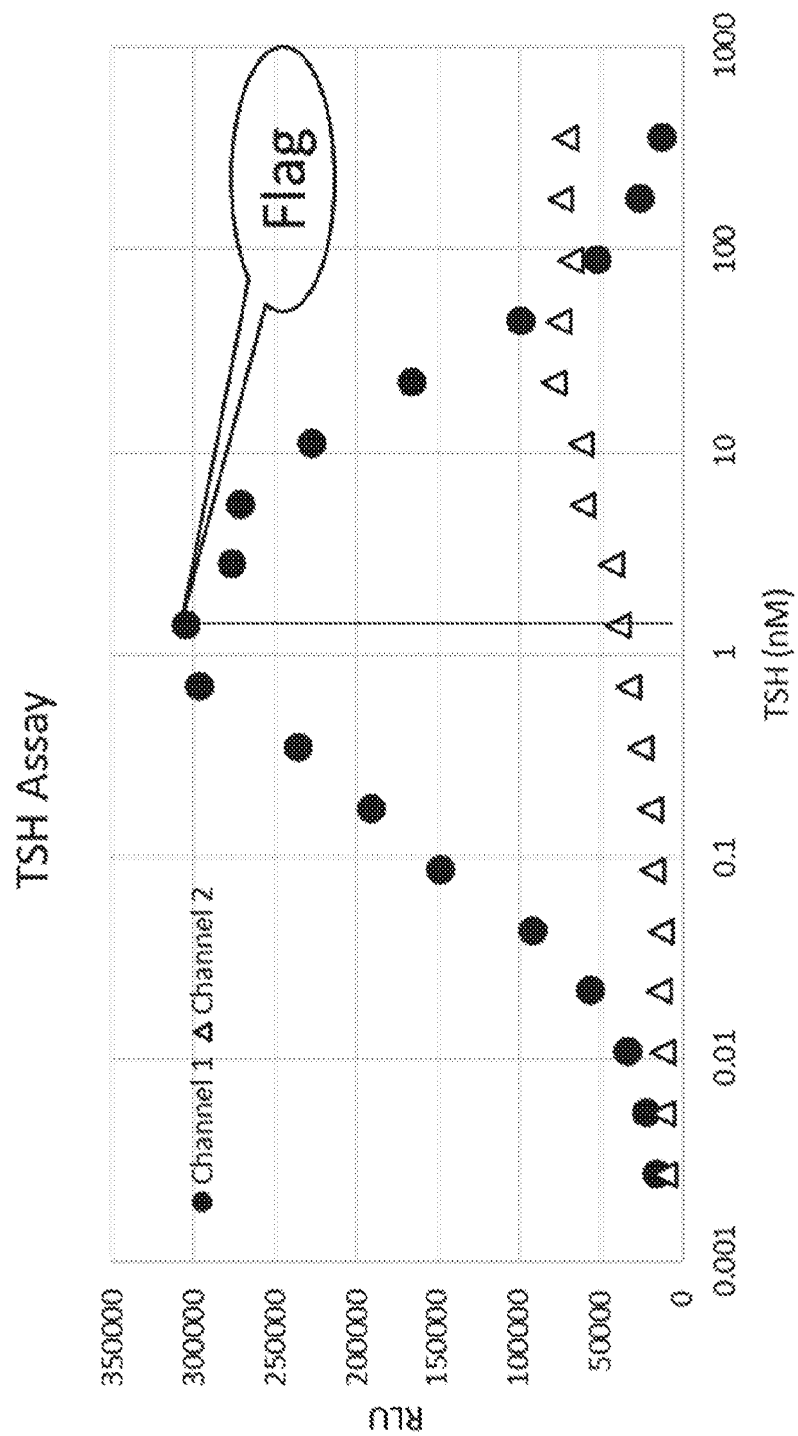
FIG. 7A is a graph showing the TSH calibration curves in both channels as described in Example 74.
Figure 7B:
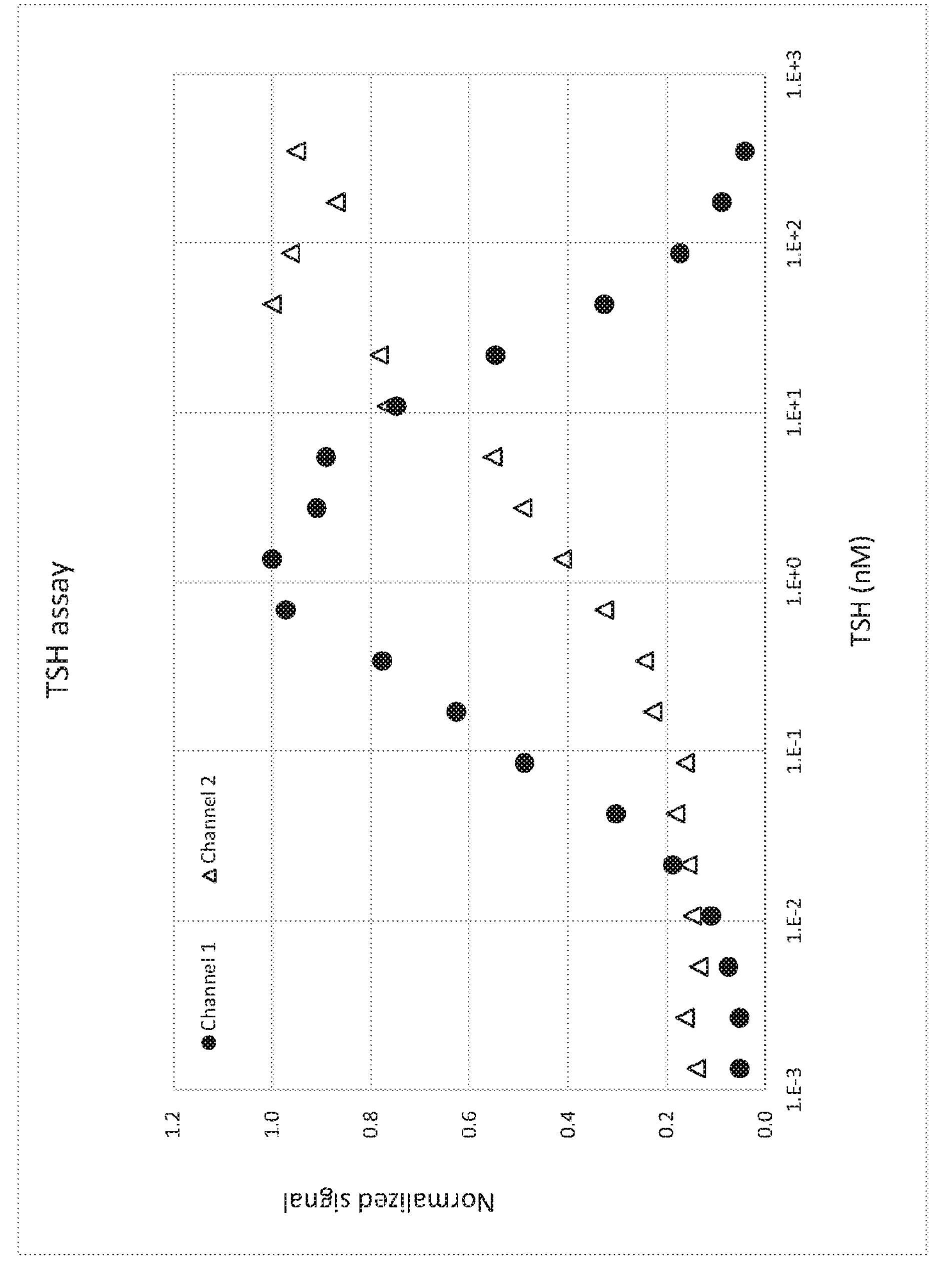
FIG. 7B is a graph showing the normalized TSH signal in both channels as described in Example 74.

A dual-color TSH assay was performed to demonstrate the feasibility of this approach. Twenty TSH samples were prepared with 2-fold serial dilutions from 351 nM to 1.3 pM, including a 0 pM control. The TSH assay kit includes the following reagents: TSH capture antibody-coated microparticles, TSH Ab-acridinium (Conjugate 1), TSH Ab-acridinium-lucifer yellow (Conjugate 2), and assay specific diluent (ASD). Conjugate 1 and Conjugate 2 are the same antibody with different labels. In the assay, 25 μL of microparticles, 150 μL sample, 70 μL ASD, and 50 μL of Conjugate 1 were mixed and incubated for 8 minutes. After a washing step, 50 μL of Conjugate 2 was added to the reaction chamber and incubated for 4 minutes. Following a second washing step, pretrigger and trigger solution were added to the reaction chamber. A dual-channel detection system incorporating a dichroic mirror was used to separate and collect signals from Conjugate 1 and Conjugate 2. FIG. 7A shows the TSH calibration curves in both channels. FIG. 7B shows the normalized signal for a clearer view of the respective curve shapes. The channel 1 signal reached its peak value at 1.4 nM (TSH), while the channel 2 signal continued to rise until it plateaued at ~20 nM. The flag value was identified and fixed at 39,000 counts. When testing an unknown sample, if the RLU from channel 2 is less than 39,000, then the ascending section of the curve from channel 1 should be used to determine analyte concentration. If the signal from channel 2 is higher than the 39,000, then the descending section of the curve from channel 1 should be used to determine analyte concentration. The shape of the calibration curve depends on the concentration of each reagent. The inflection point can be shifted to a higher or lower TSH concentration if the reagent levels are adjusted.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A kit comprising:

(a) a first conjugate comprising a first detectable label attached to a first specific binding member that specifically binds an analyte, (b) a second conjugate comprising a second detectable label attached to a second specific binding member, wherein the second specific binding member specifically binds a substance which interferes with detection of the analyte in a sample, (c) a third specific binding member attached to a solid support, which either concurrently or competitively binds to the analyte and the substance which interferes with detection of the analyte, and optionally (d) a fourth specific binding member attached to the solid support, which specifically binds to the substance which interferes with detection of the analyte, wherein at least one of the first and second detectable labels comprises a compound of formula (I), or a salt thereof:

(I)

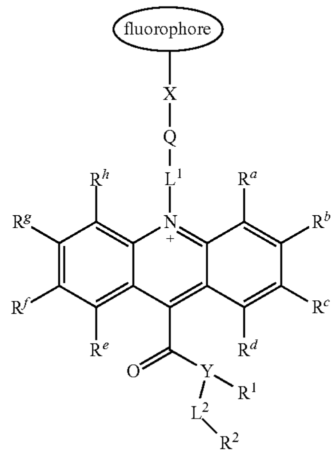

wherein:

X is ethylenediamine, 4,7,10-trioxa-1,13-tridecanediamine,

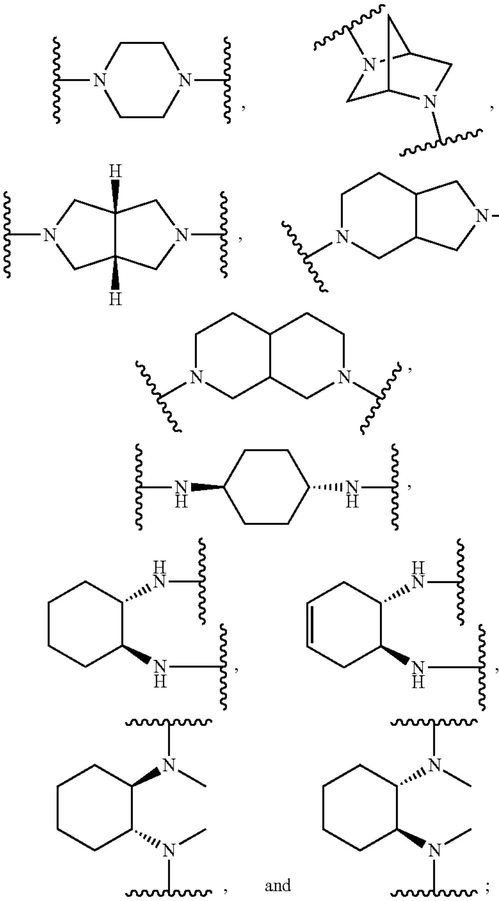

and

Y is nitrogen, oxygen, or sulfur, wherein when Y is nitrogen, $R^1$ is —$SO_2$-A, wherein A is phenyl that is unsubstituted or substituted with 1 or 2 substituents selected from $C_1$-$C_4$ alkyl, and when Y is oxygen or sulfur, $R^1$ is absent;

Q is —$SO_2$— or —CO—;

$L^1$ and $L^2$ are each independently a $C_1$-$C_4$ alkylene;

$R^2$ is —COOZ;

Z is hydrogen or $C_1$-$C_4$ alkyl; and $R^a$, $R^b$, $R^c$, $R^d$, $R^e$, $R^f$, $R^g$, and $R^h$ are each hydrogen.

2. The kit of claim 1, wherein the second specific binding member preferentially binds to the substance that interferes with detection of the analyte in the presence of the analyte.

3. The kit of claim 1, wherein the analyte is an antigen and the substance that interferes with detection of the analyte is an auto-antibody that binds to the antigen in a sample.

4. The kit of claim 1, wherein the substance that interferes with detection of the analyte is biotin.

5. A kit comprising:

(a) a first specific binding member comprising a biotin molecule and a first detectable label attached thereto, wherein the first specific binding member specifically binds an analyte;

(b) a conjugate comprising a second detectable label attached to a second specific binding member that specifically binds to the analyte;

(c) a solid support coated with streptavidin, wherein the streptavidin binds to the biotin molecule attached to the first specific binding member and a biotin molecule which interferes with detection of the analyte in a sample, wherein at least one of the first and second detectable labels comprises a compound of formula (I), or a salt thereof:

(I)

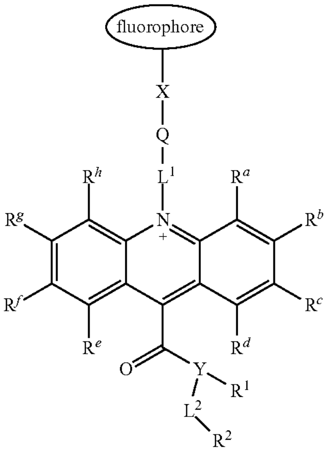

wherein:

X is ethylenediamine, 4,7,10-trioxa-1,13-tridecanediamine,

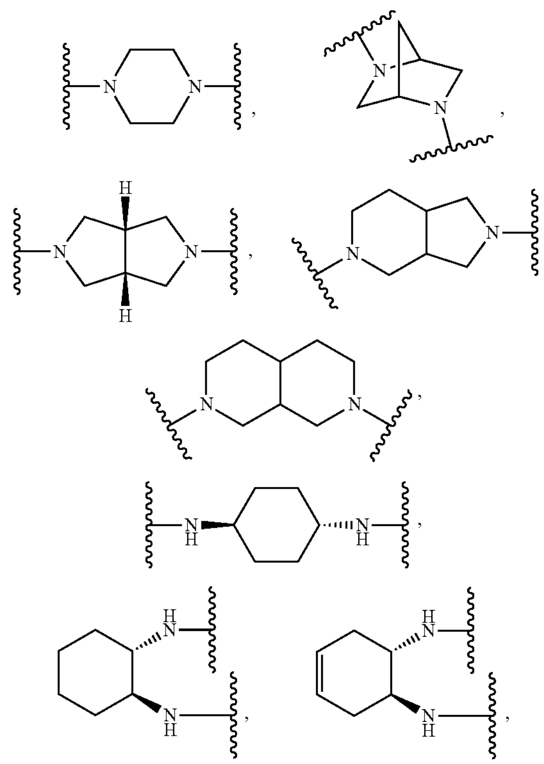

-continued

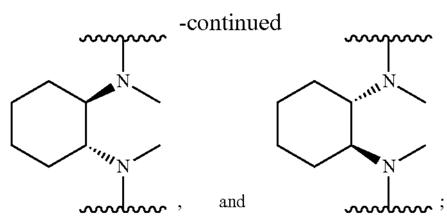

, and ;

Y is nitrogen, oxygen, or sulfur, wherein when Y is nitrogen, $R^1$ is —$SO_2$-A, wherein A is phenyl that is unsubstituted or substituted with 1 or 2 substituents selected from $C_1$-$C_4$ alkyl, and when Y is oxygen or sulfur, $R^1$ is absent;

Q is —$SO_2$— or —CO—;

$L^1$ and $L^2$ are each independently a $C_1$-$C_4$ alkylene;

$R^2$ is —COOZ;

Z is hydrogen or $C_1$-$C_4$ alkyl; and $R^a$, $R^b$, $R^c$, $R^d$, $R^e$, $R^f$, $R^g$, and $R^h$ are each hydrogen.

6. A kit comprising:

(a) a first conjugate comprising a first detectable label attached to a first specific binding member that binds an analyte, (b) a second conjugate comprising a second detectable label attached to a second specific binding member, wherein the second specific binding member binds the same analyte as the first specific binding member and the binding affinity of the first specific binding member for the analyte is greater than that of the second specific binding member, and (c) a third specific binding member attached to a solid support, which can bind to the analyte concurrently with either the first or second specific binding member, wherein at least one of the first and second detectable labels comprises a compound of formula (I), or a salt thereof:

(I)

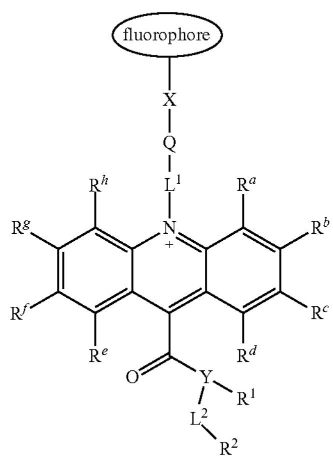

wherein:

X is ethylenediamine, 4,7,10-trioxa-1,13-tridecanediamine,

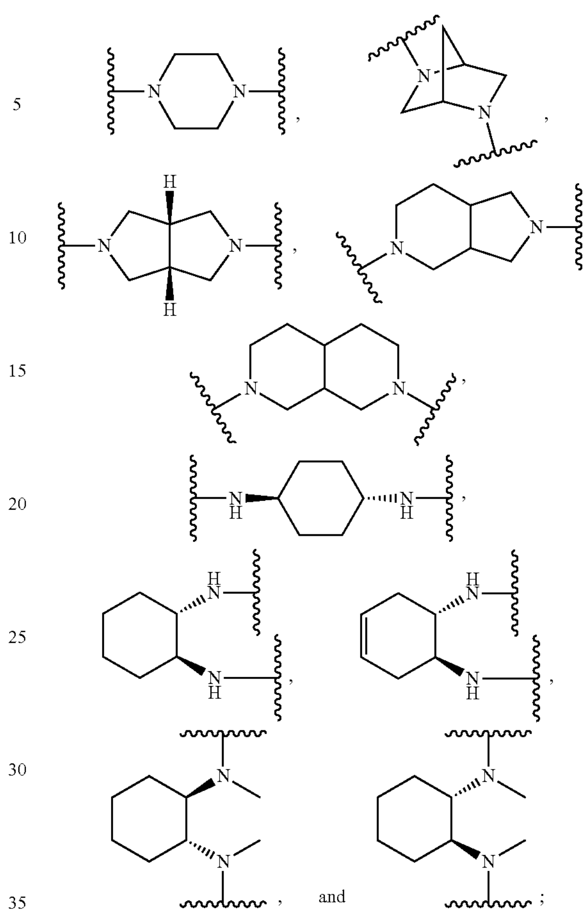

, and ;

Y is nitrogen, oxygen, or sulfur, wherein when Y is nitrogen, $R^1$ is —$SO_2$-A, wherein A is phenyl that is unsubstituted or substituted with 1 or 2 substituents selected from $C_1$-$C_4$ alkyl, and when Y is oxygen or sulfur, $R^1$ is absent;

Q is —$SO_2$— or —CO—;

$L^1$ and $L^2$ are each independently a $C_1$-$C_4$ alkylene;

$R^2$ is —COOZ;

Z is hydrogen or $C_1$-$C_4$ alkyl; and $R^a$, $R^b$, $R^c$, $R^d$, $R^e$, $R^f$, $R^g$, and $R^h$ are each hydrogen.

7. The kit of claim 6, wherein the difference in binding affinity of the first specific binding member and the second specific binding member for the analyte is from about 5-fold to about 100-fold.

8. A kit comprising:

(a) a first conjugate comprising a first specific binding member that binds an analyte and a first detectable label;

(b) a second conjugate comprising a second specific binding member and a second detectable label, wherein (i) the first specific binding member and second specific binding member are the same or are different, and (ii) the first and second detectable labels are different;

(c) a third specific binding member attached to a solid support, which can bind to the analyte concurrently with either the first or second specific binding member, wherein at least one of the first and second detectable labels comprises a compound of formula (I), or a salt thereof:

(I)

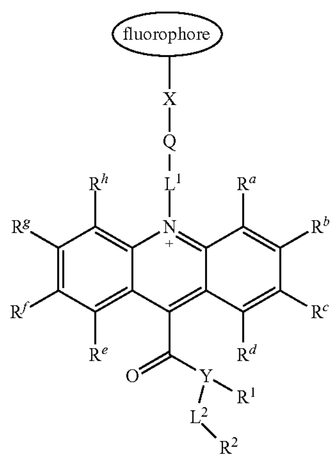

wherein:

X is ethylenediamine, 4,7,10-trioxa-1,13-tridecanediamine,

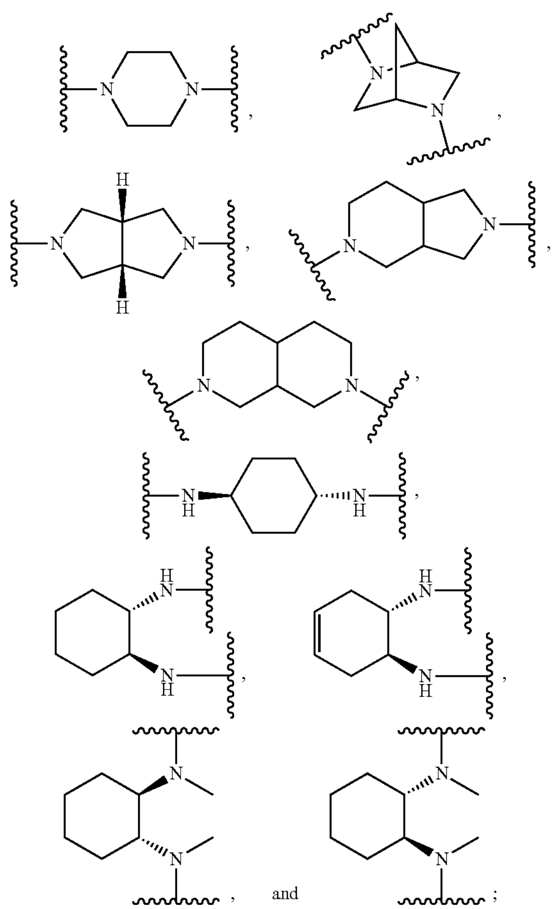

Y is nitrogen, oxygen, or sulfur, wherein when Y is nitrogen, $R^1$ is —$SO_2$-A, wherein A is phenyl that is unsubstituted or substituted with 1 or 2 substituents selected from $C_1$-$C_4$ alkyl, and when Y is oxygen or sulfur, $R^1$ is absent;

Q is —$SO_2$— or —CO—;

$L^1$ and $L^2$ are each independently a $C_1$-$C_4$ alkylene;

$R^2$ is —COOZ;

Z is hydrogen or $C_1$-$C_4$ alkyl; and $R^a$, $R^b$, $R^c$, $R^d$, $R^e$, $R^f$, $R^g$, and $R^h$ are each hydrogen.

9. The kit of claim 1, wherein X in the compound of formula (I) is

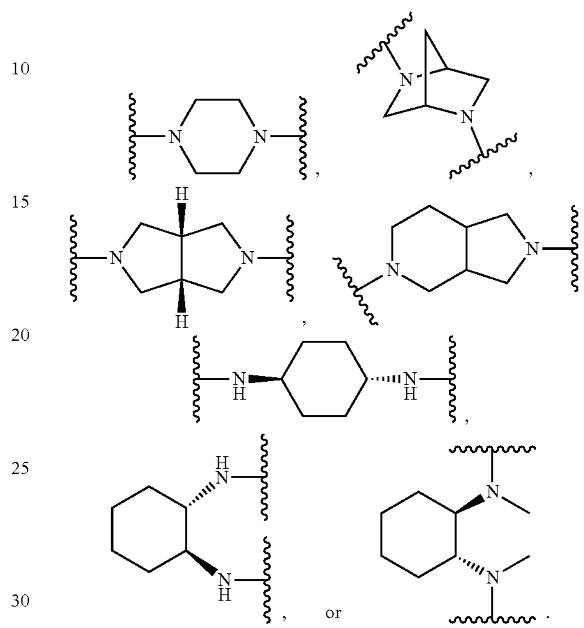

10. The kit of claim 1, wherein the compound has formula (Ia):

(Ia)

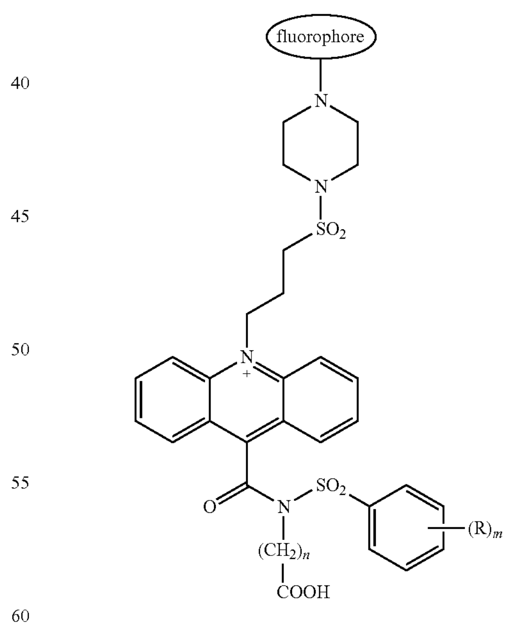

wherein:

each R is independently $C_1$-$C_4$ alkyl;

m is 0, 1, or 2; and n is 2, 3, or 4.

11. The kit of claim 1, wherein the compound has formula (Ib):

(Ib)

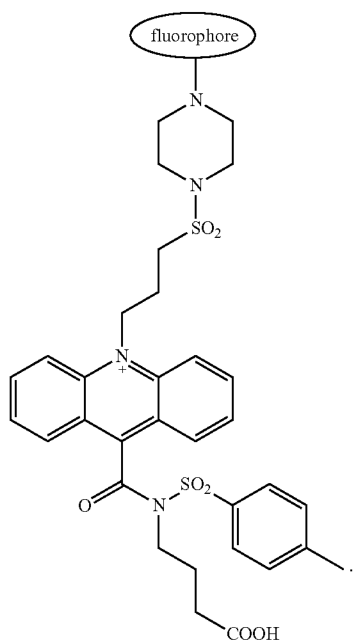

12. The kit of claim 1, wherein the first and second conjugates are of Formula (II):

(II)

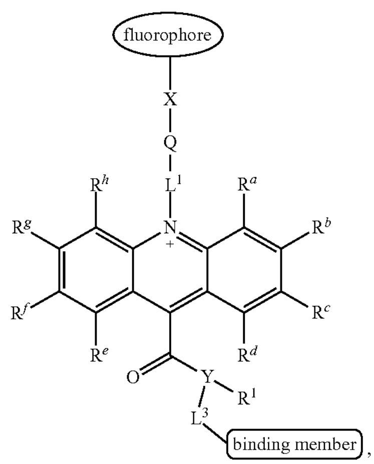

wherein:

X is ethylenediamine, 4,7,10-trioxa-1,13-tridecanediamine,

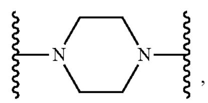,

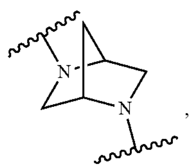,

-continued

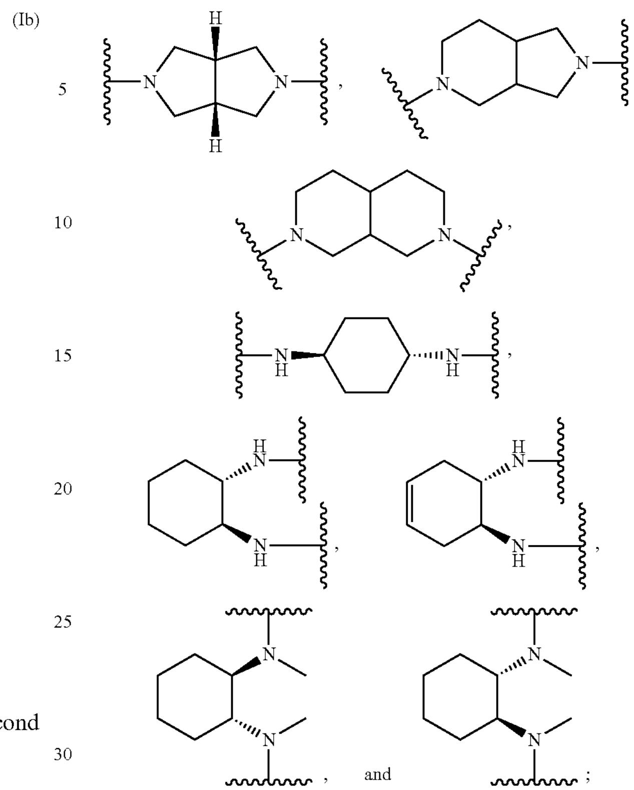

Y is nitrogen, $R^1$ is —$SO_2$-A, wherein A is phenyl that is unsubstituted or substituted with 1 or 2 substituents selected from $C_1$-$C_4$ alkyl, and when Y is oxygen or sulfur, $R^1$ is absent;

Q is —$SO_2$— or —CO—;

$L^1$ is a $C_1$-$C_4$ alkylene;

$L^3$ is a $C_1$-$C_4$ alkylene linker;

$R^a$, $R^b$, $R^c$, $R^d$, $R^e$, $R^f$, $R^g$, and $R^h$ are each hydrogen, and the binding member is a molecule capable of binding to a target analyte.

13. The kit of claim 1, wherein the fluorophore is fluorescein, a rhodamine, a boron-dipyrromethene, a cyanine, an oxazine, a thiazine, a coumarin, a naphthalimide, a rhodol, a naphthalene, a squaraine, a porphyrin, a flavin, or a lanthanide-based dye.

14. The kit of claim 1, wherein the fluorophore is

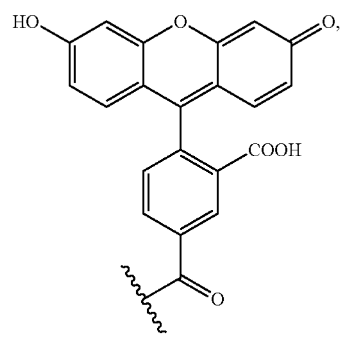

-continued
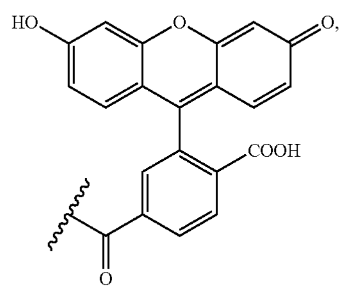
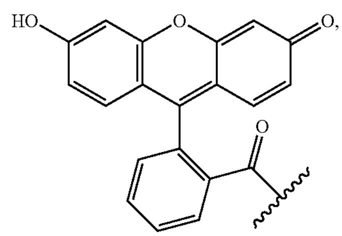
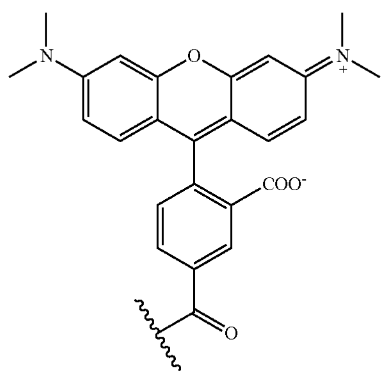
,
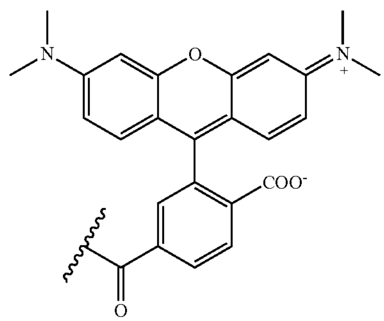
,
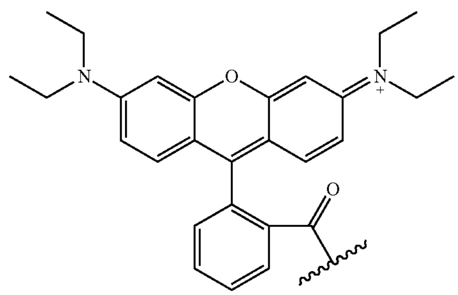
,
-continued
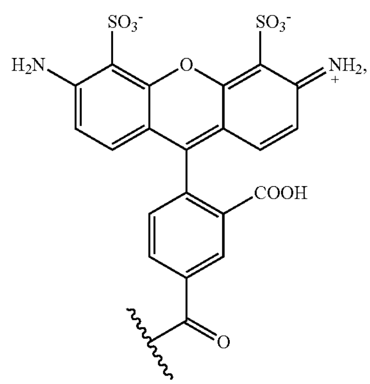
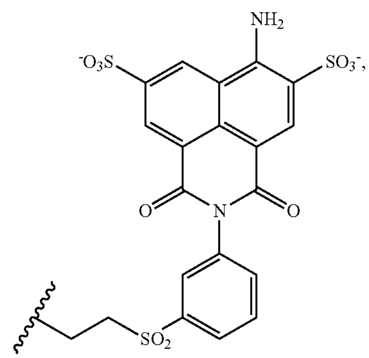
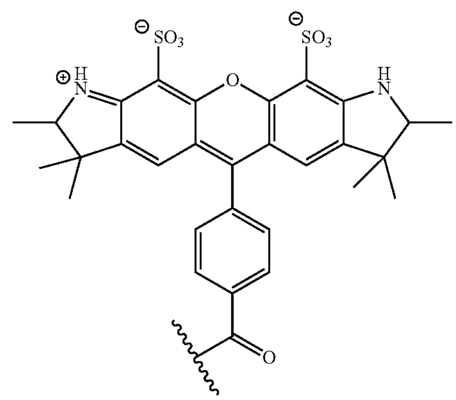
,
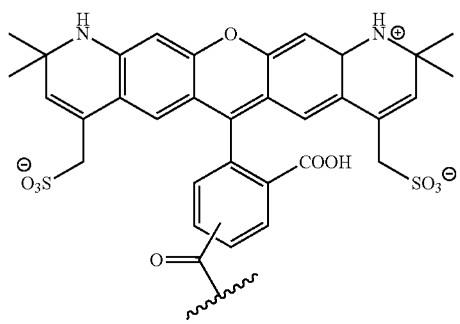
, -continued
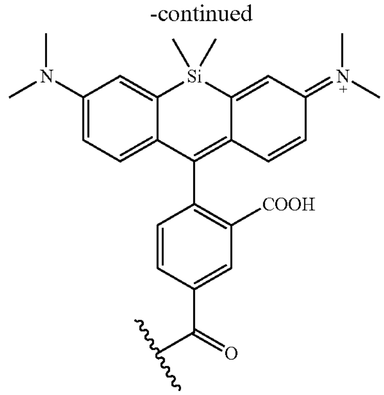
,
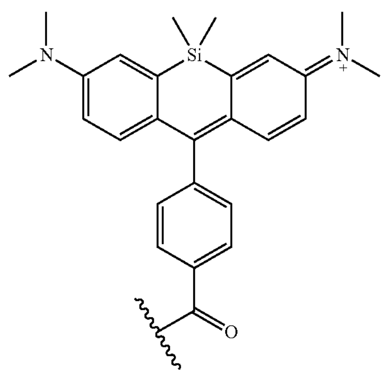
,
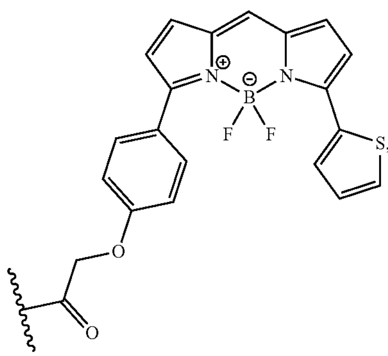
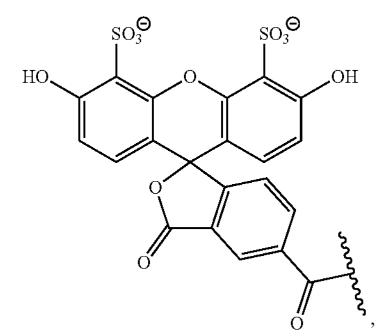
,
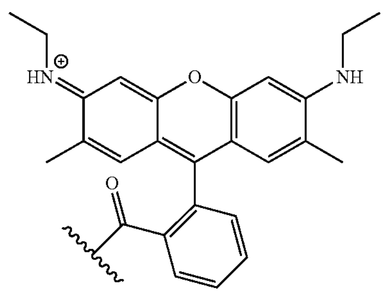
,
-continued
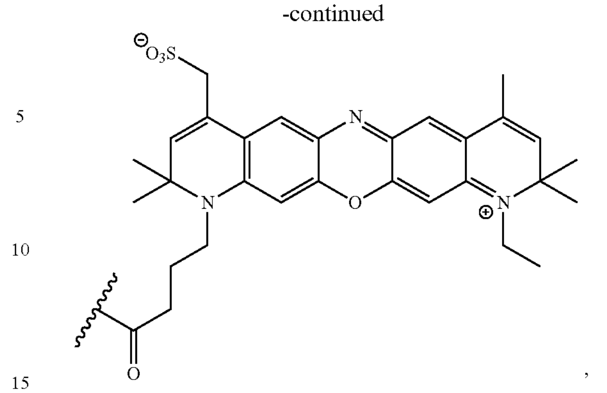
,
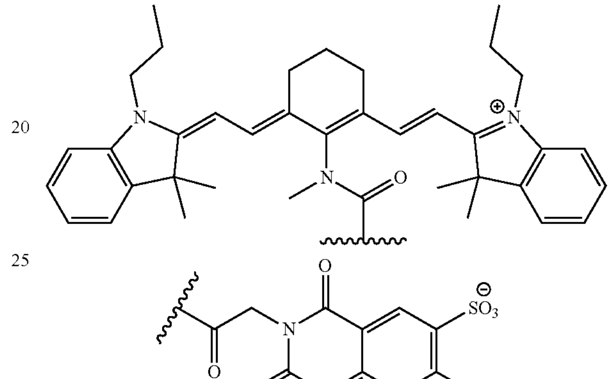
,
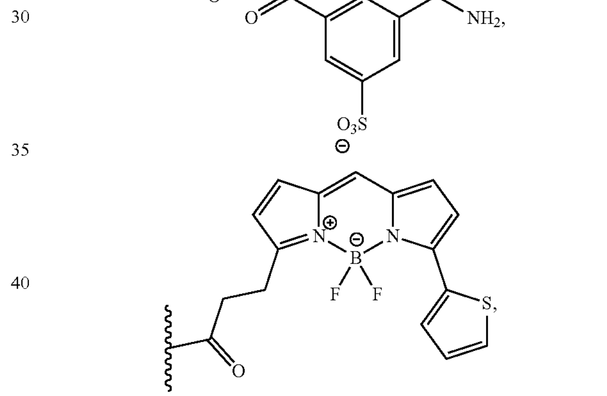
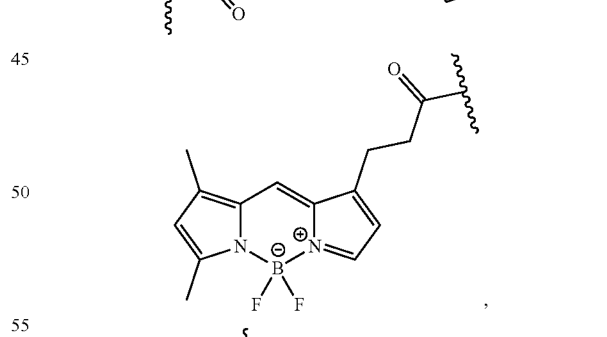
,
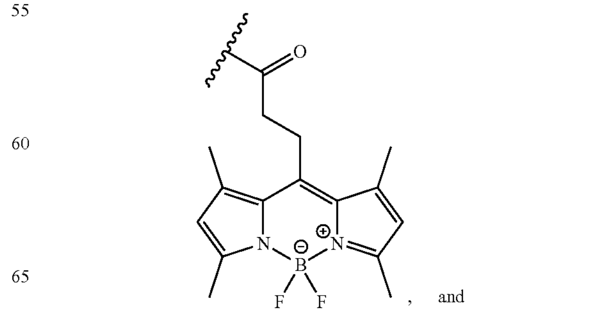
, and -continued

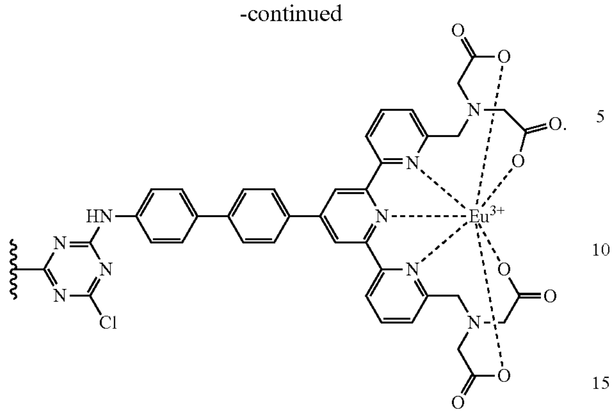

15. The kit of claim 1, wherein the first, second, third, and/or fourth specific binding member is an antibody or an antigen-binding fragment thereof.

16. The kit of claim 1, wherein the first and second specific binding members are directly attached to the first and second detectable labels, respectively.

17. The kit of claim 1, wherein the solid support is a particle, a microparticle, a bead, an electrode, or a multiwell plate.

18. The kit of claim 17, wherein the solid support comprises two or more spatially separated electrodes.

19. The kit of claim 1, wherein the first and second detectable labels are different.

20. A method of detecting a substance that interferes with detection of an analyte in a sample, which method comprises:

(a) contacting a sample suspected of comprising an analyte and a substance that interferes with detection of the analyte with the kit of claim 1 under conditions that allow:

(i) binding of the analyte to the third specific binding member, (ii) specific binding of the substance that interferes with detection of the analyte to the third specific binding member, or non-specific binding of the substance that interferes with detection of the analyte to the solid support surface, (iii) binding of the first conjugate to the analyte, (iv) binding of the second conjugate to the substance that interferes with detection of the analyte; and optionally (v) binding of a fourth specific binding member to the substance that interferes with detection of the analyte;

(b) detecting the signal intensities of the first detectable label and the second detectable label; and (c) detecting the presence of the substance that interferes with detection of the analyte in the sample by quantifying and analyzing the signal intensities of the first detectable label and the second detectable label.

21. A method of detecting a substance that interferes with detection of an analyte in a sample, which method comprises:

(a) contacting a sample suspected of comprising an analyte and a substance that interferes with detection of the analyte with the kit of claim 1 under conditions that allow:

(i) binding of the analyte to the third specific binding member and binding of the analyte to the substance that interferes with detection of the analyte to form an analyte-interferent complex, (ii) binding of the first conjugate to the analyte, and (iv) binding of the second conjugate to the substance that interferes with detection of the analyte or the analyte-interferent complex; and optionally (v) binding of a fourth specific binding member to the substance that interferes with detection of the analyte;

(b) detecting the signal intensities of the first detectable label and the second detectable label; and (c) detecting the presence of the substance that interferes with detection of the analyte in the sample by quantifying and analyzing the signal intensities of the first detectable label and the second detectable label.

22. A method of detecting a substance that interferes with detection of an analyte in a sample, which method comprises:

(a) contacting a sample suspected of comprising an analyte and a substance that interferes with detection of the analyte with the kit of claim 1 under conditions that allow:

(i) binding of the analyte to the third specific binding member, (ii) binding of the first conjugate to the analyte and binding of the first conjugate to the substance that interferes with detection of the analyte, and (iv) binding of the second conjugate to the substance that interferes with detection of the analyte; and optionally (v) binding of a fourth specific binding member to the substance that interferes with detection of the analyte;

(b) detecting the signal intensities of the first detectable label and the second detectable label; and (c) detecting the presence of the substance that interferes with detection of the analyte in the sample by quantifying and analyzing the signal intensities of the first detectable label and the second detectable label.

23. A method of detecting a substance that interferes with detection of an analyte in a sample, which method comprises:

(a) contacting a sample suspected of comprising an analyte and a substance that interferes with detection of the analyte with the kit of claim 1 under conditions that allow:

(i) binding of the analyte to the third specific binding member;

(ii) specific or non-specific binding of the substance that interferes with detection of the analyte to the solid support surface, (iii) binding of the first conjugate to the analyte and specific or non-specific binding of the substance that interferes with detection of the analyte to the first conjugate, thereby increasing the amount of first conjugate available for detection, (iv) binding of the second conjugate to the substance that interferes with detection of the analyte; and (v) binding of a fourth specific binding member to the substance that interferes with detection of the analyte;

(b) detecting the signal intensities of the first detectable label and the second detectable label; and (c) detecting the presence of the substance that interferes with detection of the analyte in the sample by quantifying and analyzing the signal intensities of the first detectable label and the second detectable label.

24. A method for detecting a biotin molecule that interferes with detection of an analyte in a sample using the kit of claim 5, which method comprises:

(a) establishing a standard signal intensity (R value) of the first detectable label binding to the streptavidin-coated solid support in the absence of an interfering biotin molecule;

(b) contacting a sample suspected of comprising both an analyte and a biotin molecule that interferes with detection of the analyte with the kit of claim 5 under conditions that allow:

(i) binding of the analyte to the first specific binding member to form a first complex;

(ii) binding of the conjugate to the analyte bound to the first specific binding member to form immunocomplexes; and (iii) binding of the streptavidin-coated solid support to the biotin molecule attached to the first specific binding member and the biotin molecule which interferes with detection of the analyte in a sample;

(c) detecting the signal intensities of the first detectable label and the second detectable label;

(d) correcting for the signal intensity of the second detectable label; and (e) detecting the presence of the biotin molecule that interferes with detection of the analyte in the sample.

25. A method of expanding the dynamic range of an immunoassay, which method comprises:

(a) contacting a test sample suspected of comprising an analyte with the kit of claim 6, wherein the analyte binds to the third specific binding member;

(b) removing analyte not bound to the third specific binding member by washing;

(c) binding the first conjugate to the analyte and the second conjugate to the analyte, wherein the first and second conjugates do not concurrently bind to the analyte;

(d) removing first and second conjugates not bound to the analyte by washing;

(b) measuring the signal intensities of the first detectable label and the second detectable label; and (c) determining the concentration of the analyte by comparing the signal intensities of the first detectable label and the second detectable label based on a flag value, whereby the dynamic range of the immunoassay is expanded.

26. A method of reducing hook effect and expanding the dynamic range of an immunoassay, which method comprises:

(a) contacting a test sample suspected of comprising an analyte with the kit of claim 8, wherein the analyte binds to the third specific binding member and the first conjugate binds to the analyte;

(b) removing any unbound analyte and unbound first conjugate by washing;

(c) binding the second conjugate to the analyte, wherein the first and second conjugates do not concurrently bind to the analyte, (d) removing any unbound second conjugate by washing;

(b) measuring the signal intensities of the first detectable label and the second detectable label; and (c) determining the concentration of the analyte based on a flag value, whereby hook effect of the immunoassay is reduced and dynamic range is expanded.

* * * * *